(12) United States Patent
Brisson

(10) Patent No.: US 8,293,522 B2
(45) Date of Patent: Oct. 23, 2012

(54) DEVICE FOR BINDING A TARGET ENTITY TO A BAIT ENTITY AND DETECTION METHODS USING THE SAME

(75) Inventor: Alain Denis Raphael Brisson, Arcachon (FR)

(73) Assignees: Centre National de la Recherche Scientifique, Paris Cedex (FR); Universite de Bordeaux 1, Talence (FR)

( * ) Notice: Subject to any disclaimer, the term of this patent is extended or adjusted under 35 U.S.C. 154(b) by 1140 days.

(21) Appl. No.: 11/596,180

(22) PCT Filed: May 12, 2005

(86) PCT No.: PCT/EP2005/005320
§ 371 (c)(1), (2), (4) Date: Feb. 4, 2008

(87) PCT Pub. No.: WO2005/114192
PCT Pub. Date: Dec. 1, 2005

(65) Prior Publication Data
US 2009/0226887 A1   Sep. 10, 2009

Related U.S. Application Data

(60) Provisional application No. 60/570,443, filed on May 13, 2004.

(51) Int. Cl.
*C12M 3/00* (2006.01)
(52) U.S. Cl. ................................... 435/287.9
(58) Field of Classification Search .................. None
See application file for complete search history.

(56) References Cited

U.S. PATENT DOCUMENTS

| | | | | |
|---|---|---|---|---|
| 5,608,060 A | * | 3/1997 | Axworthy et al. | 540/474 |
| 6,015,897 A | * | 1/2000 | Theodore et al. | 540/474 |
| 6,150,181 A | | 11/2000 | Halbreich et al. | |
| 6,511,829 B1 | * | 1/2003 | Ernst | 435/69.7 |
| 6,645,465 B2 | * | 11/2003 | Hanash et al. | 424/9.1 |
| 7,329,642 B2 | * | 2/2008 | Schroit et al. | 514/13.3 |
| 7,511,016 B2 | * | 3/2009 | Reutelingsperger | 514/1.1 |
| 2006/0052320 A1 | * | 3/2006 | Li | 514/44 |

OTHER PUBLICATIONS

Susanne Radke et al., "Specific association of annexin 1 with plasma membrane-resident and internalized EGF receptors mediated through the protein core domain," FEBS Letters, Elsevier Science Publishers, vol. 578, No. 1-2, Dec. 3, 2004, pp. 95-98.

Nicole Zobiack et al., "Complex formation and submembranous localization of annexin 2 and S100A10 in live HepG2 cells," FEBS Letters, vol. 500, Jul. 6, 2001, pp. 137-140.

Ursula Rescher et al., "Annexin 2 is a phosphatidylinositol (4,5)-bisphosphate binding protein recruited to actin assembly sites at cellular membranes," Journal of Cell Science, vol. 117, No. Pt 16, Jul. 15, 2004, pp. 3473-3480.

Harry A.M. Andree et al., "Clustering of Lipid-bound Annexin V May Explain Its Anticoagulant Effect," The Journal of Biological Chemistry, Sep. 5, 1992, vol. 267, No. 25, pp. 17907-17912.

Katja Kastl et al., "Scrutiny of Annexin A1 Mediated Membrane-Membrane Interaction by Means of a Thickness Shear Mode Resonator and Computer Simulations," Langmuir: The ACS Journal of Surfaces and Colloids, Aug. 17, 2004, vol. 20, No. 17, pp. 7246-7253.

* cited by examiner

*Primary Examiner* — Ann Lam
(74) *Attorney, Agent, or Firm* — Jacobson Holman PLLC

(57) ABSTRACT

The present invention pertains to a device for binding a target entity onto a bait entity that is immobilized on said device, comprising: a) a lipid layer having a negative net charge in an aqueous solution at a neutral pH; b) a two-dimensional matrix of anchoring complexes that are bound to said lipid layer, wherein each of said anchoring complexes comprises: (i) a fusion complex comprising an Annexin protein fused to a partner molecule; and (ii) a bait entity. It also concerns various uses of said device, including for detection and pharmaceutical purposes.

39 Claims, 15 Drawing Sheets

SEQUENCE LISTING

```
<160> NUMBER OF SEQ ID NOS: 22

<210> SEQ ID NO 1
<211> LENGTH: 319
<212> TYPE: PRT
<213> ORGANISM: Rattus norvegicus
<220> FEATURE:
<221> NAME/KEY: MISC_FEATURE
<222> LOCATION: (163)..(163)
<223> OTHER INFORMATION: Xaa can be Threonine or cysteine
<220> FEATURE:
<221> NAME/KEY: MISC_FEATURE
<222> LOCATION: (314)..(314)
<223> OTHER INFORMATION: Xaa can be Cysteine or Serine

<400> SEQUENCE: 1

Met Ala Leu Arg Gly Thr Val Thr Asp Phe Ser Gly Phe Asp Gly Arg
1               5                   10                  15

Ala Asp Ala Glu Val Leu Arg Lys Ala Met Lys Gly Leu Gly Thr Asp
            20                  25                  30

Glu Asp Ser Ile Leu Asn Leu Leu Thr Ala Arg Ser Asn Ala Gln Arg
        35                  40                  45

Gln Gln Ile Ala Glu Glu Phe Lys Thr Leu Phe Gly Arg Asp Leu Val
    50                  55                  60

Asn Asp Met Lys Ser Glu Leu Thr Gly Lys Phe Glu Lys Leu Ile Val
65                  70                  75                  80

Ala Leu Met Lys Pro Ser Arg Leu Tyr Asp Ala Tyr Glu Leu Lys His
                85                  90                  95

Ala Leu Lys Gly Ala Gly Thr Asp Glu Lys Val Leu Thr Glu Ile Ile
            100                 105                 110

Ala Ser Arg Thr Pro Glu Glu Leu Arg Ala Ile Lys Gln Ala Tyr Glu
        115                 120                 125

Glu Glu Tyr Gly Ser Asn Leu Glu Asp Asp Val Val Gly Asp Thr Ser
    130                 135                 140
```

```
Gly Tyr Tyr Gln Arg Met Leu Val Val Leu Leu Gln Ala Asn Arg Asp
145                 150                 155                 160

Pro Asp Xaa Ala Ile Asp Asp Ala Gln Val Glu Leu Asp Ala Gln Ala
            165                 170                 175

Leu Phe Gln Ala Gly Glu Leu Lys Trp Gly Thr Asp Glu Lys Phe
        180                 185                 190

Ile Thr Ile Leu Gly Thr Arg Ser Val Ser His Leu Arg Arg Val Phe
        195                 200                 205

Asp Lys Tyr Met Thr Ile Ser Gly Phe Gln Ile Glu Glu Thr Ile Asp
        210                 215                 220

Arg Glu Thr Ser Gly Asn Leu Glu Asn Leu Leu Ala Val Val Lys
225                 230                 235                 240

Ser Ile Arg Ser Ile Pro Ala Tyr Leu Ala Glu Thr Leu Tyr Tyr Ala
                245                 250                 255

Met Lys Gly Ala Gly Thr Asp Asp His Thr Leu Ile Arg Val Ile Val
            260                 265                 270

Ser Arg Ser Glu Ile Asp Leu Phe Asn Ile Arg Lys Glu Phe Arg Lys
            275                 280                 285

Asn Phe Ala Thr Ser Leu Tyr Ser Met Ile Lys Gly Asp Thr Ser Gly
290                 295                 300

Asp Tyr Lys Lys Ala Leu Leu Leu Leu Xaa Gly Gly Glu Asp Asp
305                 310                 315

<210> SEQ ID NO 2
<211> LENGTH: 320
<212> TYPE: PRT
<213> ORGANISM: Mus musculus

<400> SEQUENCE: 2

Met Met Ala Thr Arg Gly Thr Val Thr Asp Phe Pro Gly Phe Asp Gly
1               5                   10                  15

Arg Ala Asp Ala Glu Val Leu Arg Lys Ala Met Lys Gly Leu Gly Thr
            20                  25                  30

Asp Glu Asp Ser Ile Leu Asn Leu Leu Thr Ser Arg Ser Asn Ala Gln
        35                  40                  45

Arg Gln Glu Ile Ala Gln Glu Phe Lys Thr Leu Phe Gly Arg Asp Leu
50                  55                  60

Val Asp Asp Leu Lys Ser Glu Leu Thr Gly Lys Phe Glu Lys Leu Ile
65                  70                  75                  80

Val Ala Met Met Lys Pro Ser Arg Leu Tyr Asp Ala Tyr Glu Leu Lys
                85                  90                  95

His Ala Leu Lys Gly Ala Gly Thr Asp Glu Lys Val Leu Thr Glu Ile
            100                 105                 110

Ile Ala Ser Arg Thr Pro Glu Glu Leu Ser Ala Ile Lys Gln Val Tyr
        115                 120                 125

Glu Glu Glu Tyr Gly Ser Asn Leu Glu Asp Asp Val Val Gly Asp Thr
130                 135                 140

Ser Gly Tyr Tyr Gln Arg Met Leu Val Val Leu Leu Gln Ala Asn Arg
145                 150                 155                 160

Asp Pro Asp Thr Ala Ile Asp Asp Ala Gln Val Glu Leu Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Arg Val
        195                 200                 205
```

-continued

Phe Asp Lys Tyr Met Thr Ile Ser Gly Phe Gln Ile Glu Glu Thr Ile
                210                 215                 220

Asp Arg Glu Thr Ser Gly Asn Leu Glu Gln Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Val
                260                 265                 270

Val Ser Arg Ser Glu Ile Asp Leu Phe Asn Ile Arg Lys Glu Phe Arg
                275                 280                 285

Lys Asn Phe Ala Thr Ser Leu Tyr Ser Met Ile Lys Gly Asp Thr Ser
                290                 295                 300

Gly Asp Tyr Lys Lys Ala Leu Leu Leu Cys Gly Gly Glu Asp Asp
305                 310                 315                 320

<210> SEQ ID NO 3
<211> LENGTH: 320
<212> TYPE: PRT
<213> ORGANISM: Homo sapiens

<400> SEQUENCE: 3

Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
                20                  25                  30

Thr Asp Glu Glu Ser Ile Leu Thr Leu Leu Thr Ser Arg Ser Asn Ala
                35                  40                  45

Gln Arg Gln Glu Ile Ser Ala Ala Phe Lys Thr Leu Phe Gly Arg Asp
50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
                100                 105                 110

Ile Ile Ala Ser Arg Thr Pro Glu Glu Leu Arg Ala Ile Lys Gln Val
                115                 120                 125

Tyr Glu Glu Tyr Gly Ser Ser Leu Glu Asp Asp Val Val Gly Asp
                130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
                180                 185                 190

Lys Phe Ile Thr Ile Phe Gly Thr Arg Ser Val Ser His Leu Arg Lys
                195                 200                 205

Val Phe Asp Lys Tyr Met Thr Ile Ser Gly Phe Gln Ile Glu Glu Thr
                210                 215                 220

Ile Asp Arg Glu Thr Ser Gly Asn Leu Glu Gln Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
                260                 265                 270

```
Met Val Ser Arg Ser Glu Ile Asp Leu Phe Asn Ile Arg Lys Glu Phe
            275                 280                 285
Arg Lys Asn Phe Ala Thr Ser Leu Tyr Ser Met Ile Lys Gly Asp Thr
        290                 295                 300
Ser Gly Asp Tyr Lys Lys Ala Leu Leu Leu Cys Gly Glu Asp Asp
305                 310                 315                 320
```

<210> SEQ ID NO 4
<211> LENGTH: 322
<212> TYPE: PRT
<213> ORGANISM: Bos taurus

<400> SEQUENCE: 4

```
Met Met Ala Gln Val Leu Arg Gly Thr Val Ala Asp Phe Pro Gly Phe
1                   5                   10                  15
Asp Glu Arg Ala Asp Ala Glu Thr Leu Arg Lys Ala Met Lys Gly Leu
                20                  25                  30
Gly Thr Asp Glu Glu Ser Ile Leu Thr Leu Leu Thr Ser Arg Ser Asn
            35                  40                  45
Ala Gln Arg Gln Glu Ile Ala Val Ala Phe Lys Thr Leu Phe Gly Arg
        50                  55                  60
Asp Leu Leu Asp Asp Leu Lys Ser Glu Leu Thr Gly Lys Phe Glu Lys
65                  70                  75                  80
Leu Ile Val Ala Leu Met Lys Pro Ser Arg Leu Tyr Asp Ala Tyr Glu
                85                  90                  95
Leu Lys His Ala Leu Lys Gly Ala Gly Thr Asp Glu Lys Val Leu Thr
            100                 105                 110
Glu Ile Ile Ala Ser Arg Thr Pro Glu Glu Leu Arg Ala Ile Lys Gln
        115                 120                 125
Val Tyr Glu Glu Glu Tyr Gly Ser Ser Leu Glu Asp Asp Val Val Gly
130                 135                 140
Asp Thr Ser Gly Tyr Tyr Gln Arg Met Leu Val Val Leu Leu Gln Ala
145                 150                 155                 160
Asn Arg Asp Pro Asp Ala Arg Ile Asp Glu Ala Gln Val Glu Gln Asp
                165                 170                 175
Ala Gln Ala Leu Phe Gln Ala Gly Glu Leu Lys Trp Gly Thr Asp Glu
            180                 185                 190
Glu Lys Phe Ile Thr Ile Phe Gly Thr Arg Ser Val Ser His Leu Arg
        195                 200                 205
Arg Val Phe Asp Lys Tyr Met Thr Ile Ser Gly Phe Gln Ile Glu Glu
210                 215                 220
Thr Ile Asp Arg Glu Thr Ser Gly Asn Leu Glu Gln Leu Leu Leu Ala
225                 230                 235                 240
Val Val Lys Ser Ile Arg Ser Ile Pro Ala Tyr Leu Ala Glu Thr Leu
                245                 250                 255
Tyr Tyr Ala Met Lys Gly Ala Gly Thr Asp Asp His Thr Leu Ile Arg
            260                 265                 270
Val Val Val Ser Arg Ser Glu Ile Asp Leu Tyr Asn Ile Arg Lys Glu
        275                 280                 285
Phe Arg Lys Asn Phe Gly Thr Ser Leu Tyr Ser Met Ile Lys Gly Asp
290                 295                 300
Thr Ser Gly Asp Tyr Lys Lys Ala Leu Leu Leu Cys Gly Gly Glu
305                 310                 315                 320
Asp Asp
```

```
<210> SEQ ID NO 5
<211> LENGTH: 321
<212> TYPE: PRT
<213> ORGANISM: Gallus gallus

<400> SEQUENCE: 5
```

Met Ala Lys Tyr Thr Arg Gly Thr Val Thr Ala Phe Ser Pro Phe Asp
1               5                   10                  15

Ala Arg Ala Asp Ala Glu Ala Leu Arg Lys Ala Met Lys Gly Met Gly
            20                  25                  30

Thr Asp Glu Glu Thr Ile Leu Lys Ile Leu Thr Ser Arg Asn Asn Ala
        35                  40                  45

Gln Arg Gln Glu Ile Ala Ser Ala Phe Lys Thr Leu Phe Gly Arg Asp
    50                  55                  60

Leu Val Asp Asp Leu Lys Ser Glu Leu Thr Gly Lys Phe Glu Thr Leu
65                  70                  75                  80

Met Val Ser Leu Met Arg Pro Ala Arg Ile Phe Asp Ala His Ala Leu
                85                  90                  95

Lys His Ala Ile Lys Gly Ala Gly Thr Asn Glu Lys Val Leu Thr Glu
            100                 105                 110

Ile Leu Ala Ser Arg Thr Pro Ala Glu Val Gln Asn Ile Lys Gln Val
        115                 120                 125

Tyr Met Gln Glu Tyr Glu Ala Asn Leu Glu Asp Lys Ile Thr Gly Glu
    130                 135                 140

Thr Ser Gly His Phe Gln Arg Leu Leu Val Val Leu Leu Gln Ala Asn
145                 150                 155                 160

Arg Asp Pro Asp Gly Arg Val Asp Glu Ala Leu Val Glu Lys Asp Ala
                165                 170                 175

Gln Val Leu Phe Arg Ala Gly Glu Leu Lys Trp Gly Thr Asp Glu Glu
            180                 185                 190

Thr Phe Ile Thr Ile Leu Gly Thr Arg Ser Val Ser His Leu Arg Arg
        195                 200                 205

Val Phe Asp Lys Tyr Met Thr Ile Ser Gly Phe Gln Ile Glu Glu Thr
    210                 215                 220

Ile Asp Arg Glu Thr Ser Gly Asp Leu Glu Lys Leu Leu Leu Ala Val
225                 230                 235                 240

Val Lys Cys Ile Arg Ser Val Pro Ala Tyr Phe Ala Glu Thr Leu Tyr
                245                 250                 255

Tyr Ser Met Lys Gly Ala Gly Thr Asp Asp Thr Leu Ile Arg Val
            260                 265                 270

Met Val Ser Arg Ser Glu Ile Asp Leu Leu Asp Ile Arg His Glu Phe
        275                 280                 285

Arg Lys Asn Phe Ala Lys Ser Leu Tyr Gln Met Ile Gln Lys Asp Thr
    290                 295                 300

Ser Gly Asp Tyr Arg Lys Ala Leu Leu Leu Cys Gly Gly Asp Asp
305                 310                 315                 320

Glu

```
<210> SEQ ID NO 6
<211> LENGTH: 448
<212> TYPE: PRT
<213> ORGANISM: artificial sequence
<220> FEATURE:
<223> OTHER INFORMATION: fusion protein

<400> SEQUENCE: 6
```

Met Ala Leu Arg Gly Thr Val Thr Asp Phe Ser Gly Phe Asp Gly Arg

-continued

```
1               5                   10                  15
Ala Asp Ala Glu Val Leu Arg Lys Ala Met Lys Gly Leu Gly Thr Asp
                20                  25                  30
Glu Asp Ser Ile Leu Asn Leu Leu Thr Ala Arg Ser Asn Ala Gln Arg
            35                  40                  45
Gln Gln Ile Ala Glu Glu Phe Lys Thr Leu Phe Gly Arg Asp Leu Val
        50                  55                  60
Asn Asp Met Lys Ser Glu Leu Thr Gly Lys Phe Glu Lys Leu Ile Val
65                  70                  75                  80
Ala Leu Met Lys Pro Ser Arg Leu Tyr Asp Ala Tyr Glu Leu Lys His
                85                  90                  95
Ala Leu Lys Gly Ala Gly Thr Asp Glu Lys Val Leu Thr Glu Ile Ile
            100                 105                 110
Ala Ser Arg Thr Pro Glu Glu Leu Arg Ala Ile Lys Gln Ala Tyr Glu
        115                 120                 125
Glu Glu Tyr Gly Ser Asn Leu Glu Asp Asp Val Val Gly Asp Thr Ser
    130                 135                 140
Gly Tyr Tyr Gln Arg Met Leu Val Val Leu Leu Gln Ala Asn Arg Asp
145                 150                 155                 160
Pro Asp Cys Ala Ile Asp Asp Ala Gln Val Glu Leu Asp Ala Gln Ala
                165                 170                 175
Leu Phe Gln Ala Gly Glu Leu Lys Trp Gly Thr Asp Glu Glu Lys Phe
            180                 185                 190
Ile Thr Ile Leu Gly Thr Arg Ser Val Ser His Leu Arg Arg Val Phe
        195                 200                 205
Asp Lys Tyr Met Thr Ile Ser Gly Phe Gln Ile Glu Glu Thr Ile Asp
    210                 215                 220
Arg Glu Thr Ser Gly Asn Leu Glu Asn Leu Leu Leu Ala Val Val Lys
225                 230                 235                 240
Ser Ile Arg Ser Ile Pro Ala Tyr Leu Ala Glu Thr Leu Tyr Tyr Ala
                245                 250                 255
Met Lys Gly Ala Gly Thr Asp Asp His Thr Leu Ile Arg Val Ile Val
            260                 265                 270
Ser Arg Ser Glu Ile Asp Leu Phe Asn Ile Arg Lys Glu Phe Arg Lys
        275                 280                 285
Asn Phe Ala Thr Ser Leu Tyr Ser Met Ile Lys Gly Asp Thr Ser Gly
    290                 295                 300
Asp Tyr Lys Lys Ala Leu Leu Leu Leu Ser Gly Gly Glu Asp Asp Leu
305                 310                 315                 320
Ala Ser Gln Ala Val Asp Asn Lys Phe Asn Lys Glu Gln Gln Asn Ala
                325                 330                 335
Phe Tyr Glu Ile Leu His Leu Pro Asn Leu Asn Glu Glu Gln Arg Asn
            340                 345                 350
Ala Phe Ile Gln Ser Leu Lys Asp Asp Pro Ser Gln Ser Ala Asn Leu
        355                 360                 365
Leu Ala Glu Ala Lys Lys Leu Asn Asp Ala Gln Ala Pro Lys Val Asp
    370                 375                 380
Asn Lys Phe Asn Lys Glu Gln Gln Asn Ala Phe Tyr Glu Ile Leu His
385                 390                 395                 400
Leu Pro Asn Leu Asn Glu Glu Gln Arg Asn Ala Phe Ile Gln Ser Leu
                405                 410                 415
Lys Asp Asp Pro Ser Gln Ser Ala Asn Leu Leu Ala Glu Ala Lys Lys
            420                 425                 430
```

Leu Asn Asp Ala Gln Ala Pro Lys Val Asp Ala Asn Ser Ser Val
    435                 440                 445

<210> SEQ ID NO 7
<211> LENGTH: 346
<212> TYPE: PRT
<213> ORGANISM: Homo sapiens

<400> SEQUENCE: 7

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 8
<211> LENGTH: 339

<212> TYPE: PRT
<213> ORGANISM: Homo sapiens

<400> SEQUENCE: 8

```
Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
130                 135                 140

Arg Val Tyr Lys Glu Met Tyr Lys Thr Asp Leu Glu Lys Asp Ile Ile
145                 150                 155                 160

Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
            180                 185                 190

Gln Asp Ala Arg Asp Leu Tyr Asp Ala Gly Val Lys Arg Lys Gly Thr
        195                 200                 205

Asp Val Pro Lys Trp Ile Ser Ile Met Thr Glu Arg Ser Val Pro His
210                 215                 220

Leu Gln Lys Val Phe Asp Arg Tyr Lys Ser Tyr Ser Pro Tyr Asp Met
225                 230                 235                 240

Leu Glu Ser Ile Arg Lys Glu Val Lys Gly Asp Leu Glu Asn Ala Phe
                245                 250                 255

Leu Asn Leu Val Gln Cys Ile Gln Asn Lys Pro Leu Tyr Phe Ala Asp
            260                 265                 270

Arg Leu Tyr Asp Ser Met Lys Gly Lys Gly Thr Arg Asp Lys Val Leu
        275                 280                 285

Ile Arg Ile Met Val Ser Arg Ser Glu Val Asp Met Leu Lys Ile Arg
290                 295                 300

Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
                325                 330                 335

Gly Asp Asp
```

<210> SEQ ID NO 9
<211> LENGTH: 673
<212> TYPE: PRT
<213> ORGANISM: Homo sapiens

<400> SEQUENCE: 9

```
Met Ala Lys Pro Ala Gln Gly Ala Lys Tyr Arg Gly Ser Ile His Asp
1               5                   10                  15
```

Phe Pro Gly Phe Asp Pro Asn Gln Asp Ala Glu Ala Leu Tyr Thr Ala
                20                  25                  30

Met Lys Gly Phe Gly Ser Asp Lys Glu Ala Ile Leu Asp Ile Ile Thr
            35                  40                  45

Ser Arg Ser Asn Arg Gln Arg Gln Glu Val Cys Gln Ser Tyr Lys Ser
50                  55                  60

Leu Tyr Gly Lys Asp Leu Ile Ala Asp Leu Lys Tyr Glu Leu Thr Gly
65                  70                  75                  80

Lys Phe Glu Arg Leu Ile Val Gly Leu Met Arg Pro Pro Ala Tyr Cys
                85                  90                  95

Asp Ala Lys Glu Ile Lys Asp Ala Ile Ser Gly Ile Gly Thr Asp Glu
            100                 105                 110

Lys Cys Leu Ile Glu Ile Leu Ala Ser Arg Thr Asn Glu Gln Met His
        115                 120                 125

Gln Leu Val Ala Ala Tyr Lys Asp Ala Tyr Glu Arg Asp Leu Glu Ala
    130                 135                 140

Asp Ile Ile Gly Asp Thr Ser Gly His Phe Gln Lys Met Leu Val Val
145                 150                 155                 160

Leu Leu Gln Gly Thr Arg Glu Glu Asp Asp Val Val Ser Glu Asp Leu
                165                 170                 175

Val Gln Gln Asp Val Gln Asp Leu Tyr Glu Ala Gly Glu Leu Lys Trp
            180                 185                 190

Gly Thr Asp Glu Ala Gln Phe Ile Tyr Ile Leu Gly Asn Arg Ser Lys
        195                 200                 205

Gln His Leu Arg Leu Val Phe Asp Glu Tyr Leu Lys Thr Thr Gly Lys
    210                 215                 220

Pro Ile Glu Ala Ser Ile Arg Gly Glu Leu Ser Gly Asp Phe Glu Lys
225                 230                 235                 240

Leu Met Leu Ala Val Val Lys Cys Ile Arg Ser Thr Pro Glu Tyr Phe
                245                 250                 255

Ala Glu Arg Leu Phe Lys Ala Met Lys Gly Leu Gly Thr Arg Asp Asn
            260                 265                 270

Thr Leu Ile Arg Ile Met Val Ser Arg Ser Glu Leu Asp Met Leu Asp
        275                 280                 285

Ile Arg Glu Ile Phe Arg Thr Lys Tyr Glu Lys Ser Leu Tyr Ser Met
    290                 295                 300

Ile Lys Asn Asp Thr Ser Gly Glu Tyr Lys Lys Thr Leu Leu Lys Leu
305                 310                 315                 320

Ser Gly Gly Asp Asp Asp Ala Ala Gly Gln Phe Phe Pro Glu Ala Ala
                325                 330                 335

Gln Val Ala Tyr Gln Met Trp Glu Leu Ser Ala Val Ala Arg Val Glu
            340                 345                 350

Leu Lys Gly Thr Val Arg Pro Ala Asn Asp Phe Asn Pro Asp Ala Asp
        355                 360                 365

Ala Lys Ala Leu Arg Lys Ala Met Lys Gly Leu Gly Thr Asp Glu Asp
    370                 375                 380

Thr Ile Ile Asp Ile Ile Thr His Arg Ser Asn Val Gln Arg Gln Gln
385                 390                 395                 400

Ile Arg Gln Thr Phe Lys Ser His Phe Gly Arg Asp Leu Met Thr Asp
                405                 410                 415

Leu Lys Ser Glu Ile Ser Gly Asp Leu Ala Arg Leu Ile Leu Gly Leu
            420                 425                 430

Met Met Pro Pro Ala His Tyr Asp Ala Lys Gln Leu Lys Lys Ala Met

-continued

```
            435                 440                 445
Glu Gly Ala Gly Thr Asp Glu Lys Ala Leu Ile Glu Ile Leu Ala Thr
            450                 455                 460
Arg Thr Asn Ala Glu Ile Arg Ala Ile Asn Glu Ala Tyr Lys Glu Asp
465                 470                 475                 480
Tyr His Lys Ser Leu Glu Asp Ala Leu Ser Ser Asp Thr Ser Gly His
                485                 490                 495
Phe Arg Arg Ile Leu Ile Ser Leu Ala Thr Gly His Arg Glu Glu Gly
            500                 505                 510
Gly Glu Asn Leu Asp Gln Ala Arg Glu Asp Ala Gln Val Ala Ala Glu
            515                 520                 525
Ile Leu Glu Ile Ala Asp Thr Pro Ser Gly Asp Lys Thr Ser Leu Glu
            530                 535                 540
Thr Arg Phe Met Thr Ile Leu Cys Thr Arg Ser Tyr Pro His Leu Arg
545                 550                 555                 560
Arg Val Phe Gln Glu Phe Ile Lys Met Thr Asn Tyr Asp Val Glu His
                565                 570                 575
Thr Ile Lys Lys Glu Met Ser Gly Asp Val Arg Asp Ala Phe Val Ala
            580                 585                 590
Ile Val Gln Ser Val Lys Asn Lys Pro Leu Phe Phe Ala Asp Lys Leu
            595                 600                 605
Tyr Lys Ser Met Lys Gly Ala Gly Thr Asp Glu Lys Thr Leu Thr Arg
            610                 615                 620
Ile Met Val Ser Arg Ser Glu Ile Asp Leu Leu Asn Ile Arg Arg Glu
625                 630                 635                 640
Phe Ile Glu Lys Tyr Asp Lys Ser Leu His Gln Ala Ile Glu Gly Asp
                645                 650                 655
Thr Ser Gly Asp Phe Leu Lys Ala Leu Leu Ala Leu Cys Gly Gly Glu
            660                 665                 670
Asp

<210> SEQ ID NO 10
<211> LENGTH: 319
<212> TYPE: PRT
<213> ORGANISM: Homo sapiens

<400> SEQUENCE: 10

Met Ala Thr Lys Gly Gly Thr Val Lys Ala Ala Ser Gly Phe Asn Ala
1               5                   10                  15
Met Glu Asp Ala Gln Thr Leu Arg Lys Ala Met Lys Gly Leu Gly Thr
            20                  25                  30
Asp Glu Asp Ala Ile Ile Ser Val Leu Ala Tyr Arg Asn Thr Ala Gln
        35                  40                  45
Arg Gln Glu Ile Arg Thr Ala Tyr Lys Ser Thr Ile Gly Arg Asp Leu
    50                  55                  60
Ile Asp Asp Leu Lys Ser Glu Leu Ser Gly Asn Phe Glu Gln Val Ile
65                  70                  75                  80
Val Gly Met Met Thr Pro Thr Val Leu Tyr Asp Val Gln Glu Leu Arg
                85                  90                  95
Arg Ala Met Lys Gly Ala Gly Thr Asp Glu Gly Cys Leu Ile Glu Ile
            100                 105                 110
Leu Ala Ser Arg Thr Pro Glu Glu Ile Arg Arg Ile Ser Gln Thr Tyr
            115                 120                 125
Gln Gln Gln Tyr Gly Arg Ser Leu Glu Asp Asp Ile Arg Ser Asp Thr
            130                 135                 140
```

```
Ser Phe Met Phe Gln Arg Val Leu Val Ser Leu Ser Ala Gly Gly Arg
145                 150                 155                 160

Asp Glu Gly Asn Tyr Leu Asp Asp Ala Leu Val Arg Gln Asp Ala Gln
            165                 170                 175

Asp Leu Tyr Glu Ala Gly Glu Lys Lys Trp Gly Thr Asp Glu Val Lys
        180                 185                 190

Phe Leu Thr Val Leu Cys Ser Arg Asn Arg Asn His Leu Leu His Val
    195                 200                 205

Phe Asp Glu Tyr Lys Arg Ile Ser Gln Lys Asp Ile Glu Gln Ser Ile
210                 215                 220

Lys Ser Glu Thr Ser Gly Ser Phe Glu Asp Ala Leu Leu Ala Ile Val
225                 230                 235                 240

Lys Cys Met Arg Asn Lys Ser Ala Tyr Phe Ala Glu Lys Leu Tyr Lys
                245                 250                 255

Ser Met Lys Gly Leu Gly Thr Asp Asp Asn Thr Leu Ile Arg Val Met
            260                 265                 270

Val Ser Arg Ala Glu Ile Asp Met Leu Asp Ile Arg Ala His Phe Lys
        275                 280                 285

Arg Leu Tyr Gly Lys Ser Leu Tyr Ser Phe Ile Lys Gly Asp Thr Ser
    290                 295                 300

Gly Asp Tyr Arg Lys Val Leu Leu Val Leu Cys Gly Gly Asp Asp
305                 310                 315

<210> SEQ ID NO 11
<211> LENGTH: 327
<212> TYPE: PRT
<213> ORGANISM: Homo sapiens

<400> SEQUENCE: 11

Met Ala Trp Trp Lys Ala Trp Ile Glu Gln Glu Gly Val Thr Val Lys
1               5                   10                  15

Ser Ser Ser His Phe Asn Pro Asp Pro Asp Ala Glu Thr Leu Tyr Lys
            20                  25                  30

Ala Met Lys Gly Ile Gly Thr Asn Glu Gln Ala Ile Ile Asp Val Leu
        35                  40                  45

Thr Lys Arg Ser Asn Thr Gln Arg Gln Gln Ile Ala Lys Ser Phe Lys
    50                  55                  60

Ala Gln Phe Gly Lys Asp Leu Thr Glu Thr Leu Lys Ser Glu Leu Ser
65                  70                  75                  80

Gly Lys Phe Glu Arg Leu Ile Val Ala Leu Met Tyr Pro Pro Tyr Arg
                85                  90                  95

Tyr Glu Ala Lys Glu Leu His Asp Ala Met Lys Gly Leu Gly Thr Lys
            100                 105                 110

Glu Gly Val Ile Ile Glu Ile Leu Ala Ser Arg Thr Lys Asn Gln Leu
        115                 120                 125

Arg Glu Ile Met Lys Ala Tyr Glu Glu Asp Tyr Gly Ser Ser Leu Glu
    130                 135                 140

Glu Asp Ile Gln Ala Asp Thr Ser Gly Tyr Leu Glu Arg Ile Leu Val
145                 150                 155                 160

Cys Leu Leu Gln Gly Ser Arg Asp Asp Val Ser Ser Phe Val Asp Pro
                165                 170                 175

Ala Leu Ala Leu Gln Asp Ala Gln Asp Leu Tyr Ala Ala Gly Glu Lys
            180                 185                 190

Ile Arg Gly Thr Asp Glu Met Lys Phe Ile Thr Ile Leu Cys Thr Arg
        195                 200                 205
```

```
Ser Ala Thr His Leu Leu Arg Val Phe Glu Glu Tyr Glu Lys Ile Ala
    210                 215                 220

Asn Lys Ser Ile Glu Asp Ser Ile Lys Ser Glu Thr His Gly Ser Leu
225                 230                 235                 240

Glu Glu Ala Met Leu Thr Val Val Lys Cys Thr Gln Asn Leu His Ser
                245                 250                 255

Tyr Phe Ala Glu Arg Leu Tyr Tyr Ala Met Lys Gly Ala Gly Thr Arg
            260                 265                 270

Asp Gly Thr Leu Ile Arg Asn Ile Val Ser Arg Ser Glu Ile Asp Leu
        275                 280                 285

Asn Leu Ile Lys Cys His Phe Lys Lys Met Tyr Gly Lys Thr Leu Ser
290                 295                 300

Ser Met Ile Met Glu Asp Thr Ser Gly Asp Tyr Lys Asn Ala Leu Leu
305                 310                 315                 320

Ser Leu Val Gly Ser Asp Pro
                325

<210> SEQ ID NO 12
<211> LENGTH: 466
<212> TYPE: PRT
<213> ORGANISM: Homo sapiens

<400> SEQUENCE: 12

Met Ser Tyr Pro Gly Tyr Pro Pro Thr Gly Tyr Pro Pro Phe Pro Gly
1               5                   10                  15

Tyr Pro Pro Ala Gly Gln Glu Ser Ser Phe Pro Pro Ser Gly Gln Tyr
            20                  25                  30

Pro Tyr Pro Ser Gly Phe Pro Pro Met Gly Gly Gly Ala Tyr Pro Gln
        35                  40                  45

Val Pro Ser Ser Gly Tyr Pro Gly Ala Gly Gly Tyr Pro Ala Pro Gly
    50                  55                  60

Gly Tyr Pro Ala Pro Gly Gly Tyr Pro Gly Ala Pro Gln Pro Gly Gly
65                  70                  75                  80

Ala Pro Ser Tyr Pro Gly Val Pro Pro Gly Gln Gly Phe Gly Val Pro
                85                  90                  95

Pro Gly Gly Ala Gly Phe Ser Gly Tyr Pro Gln Pro Pro Ser Gln Ser
            100                 105                 110

Tyr Gly Gly Gly Pro Ala Gln Val Pro Leu Pro Gly Gly Phe Pro Gly
        115                 120                 125

Gly Gln Met Pro Ser Gln Tyr Pro Gly Gly Gln Pro Thr Tyr Pro Ser
    130                 135                 140

Gln Pro Ala Thr Val Thr Gln Val Thr Gln Gly Thr Ile Arg Pro Ala
145                 150                 155                 160

Ala Asn Phe Asp Ala Ile Arg Asp Ala Glu Ile Leu Arg Lys Ala Met
                165                 170                 175

Lys Gly Phe Gly Thr Asp Glu Gln Ala Ile Val Asp Val Val Ala Asn
            180                 185                 190

Arg Ser Asn Asp Gln Arg Gln Lys Ile Lys Ala Ala Phe Lys Thr Ser
        195                 200                 205

Tyr Gly Lys Asp Leu Ile Lys Asp Leu Lys Ser Glu Leu Ser Gly Asn
    210                 215                 220

Met Glu Glu Leu Ile Leu Ala Leu Phe Met Pro Thr Tyr Tyr Asp
225                 230                 235                 240

Ala Trp Ser Leu Arg Lys Ala Met Gln Gly Ala Gly Thr Gln Glu Arg
                245                 250                 255
```

```
Val Leu Ile Glu Ile Leu Cys Thr Arg Thr Asn Gln Glu Ile Arg Glu
            260                 265                 270

Ile Val Arg Cys Tyr Gln Ser Glu Phe Gly Arg Asp Leu Glu Lys Asp
        275                 280                 285

Ile Arg Ser Asp Thr Ser Gly His Phe Glu Arg Leu Leu Val Ser Met
    290                 295                 300

Cys Gln Gly Asn Arg Asp Glu Asn Gln Ser Ile Asn His Gln Met Ala
305                 310                 315                 320

Gln Glu Asp Ala Gln Arg Leu Tyr Gln Ala Gly Glu Gly Arg Leu Gly
                325                 330                 335

Thr Asp Glu Ser Cys Phe Asn Met Ile Leu Ala Thr Arg Ser Phe Pro
            340                 345                 350

Gln Leu Arg Ala Thr Met Glu Ala Tyr Ser Arg Met Ala Asn Arg Asp
        355                 360                 365

Leu Leu Ser Ser Val Ser Arg Glu Phe Ser Gly Tyr Val Glu Ser Gly
    370                 375                 380

Leu Lys Thr Ile Leu Gln Cys Ala Leu Asn Arg Pro Ala Phe Phe Ala
385                 390                 395                 400

Glu Arg Leu Tyr Tyr Ala Met Lys Gly Ala Gly Thr Asp Asp Ser Thr
                405                 410                 415

Leu Val Arg Ile Val Val Thr Arg Ser Glu Ile Asp Leu Val Gln Ile
            420                 425                 430

Lys Gln Met Phe Ala Gln Met Tyr Gln Lys Thr Leu Gly Thr Met Ile
        435                 440                 445

Ala Gly Asp Thr Ser Gly Asp Tyr Arg Arg Leu Leu Leu Ala Ile Val
    450                 455                 460

Gly Gln
465

<210> SEQ ID NO 13
<211> LENGTH: 316
<212> TYPE: PRT
<213> ORGANISM: hydra attenuata

<400> SEQUENCE: 13

Met Val Val Gln Gly Thr Val Lys Pro His Ala Ser Phe Asn Ser Arg
1               5                   10                  15

Glu Asp Ala Glu Thr Leu Arg Lys Ala Met Lys Gly Ile Gly Thr Asp
            20                  25                  30

Glu Lys Ser Ile Thr His Ile Leu Ala Thr Arg Ser Asn Ala Gln Arg
        35                  40                  45

Gln Gln Ile Lys Thr Asp Tyr Thr Thr Leu Phe Gly Lys His Leu Glu
    50                  55                  60

Asp Glu Leu Lys Ser Glu Leu Ser Gly Asn Tyr Glu Ala Ala Ala Leu
65                  70                  75                  80

Ala Leu Leu Arg Lys Pro Asp Glu Phe Leu Ala Glu Gln Leu His Ala
                85                  90                  95

Ala Met Lys Gly Leu Gly Thr Asp Glu Asn Ala Leu Ile Asp Ile Leu
            100                 105                 110

Cys Thr Gln Ser Asn Ala Gln Ile His Ala Ile Lys Ala Ala Phe Lys
        115                 120                 125

Leu Leu Tyr Lys Glu Asp Leu Glu Lys Glu Ile Ile Ser Glu Thr Ser
    130                 135                 140

Gly Asn Phe Gln Arg Leu Leu Val Ser Met Leu Gln Gly Gly Arg Lys
145                 150                 155                 160
```

```
Glu Asp Glu Pro Val Asn Ala Ala His Ala Ala Glu Asp Ala Ala Ala
                165                 170                 175

Ile Tyr Gln Ala Gly Glu Gly Gln Ile Gly Thr Asp Glu Ser Arg Phe
            180                 185                 190

Asn Ala Val Leu Ala Thr Arg Ser Tyr Pro Gln Leu His Gln Ile Phe
            195                 200                 205

His Glu Tyr Ser Lys Ile Ser Asn Lys Thr Ile Leu Gln Ala Ile Glu
        210                 215                 220

Asn Glu Phe Ser Gly Asp Ile Lys Asn Gly Leu Leu Ala Ile Val Lys
225                 230                 235                 240

Ser Val Glu Asn Arg Phe Ala Tyr Phe Ala Glu Arg Leu His His Ala
                245                 250                 255

Met Lys Gly Leu Gly Thr Ser Asp Lys Thr Leu Ile Arg Ile Leu Val
            260                 265                 270

Ser Arg Ser Glu Ile Asp Leu Ala Asn Ile Lys Glu Thr Phe Gln Ala
            275                 280                 285

Met Tyr Gly Lys Ser Leu Tyr Glu Phe Ile Ala Asp Asp Cys Ser Gly
        290                 295                 300

Asp Tyr Lys Asp Leu Leu Leu Gln Ile Thr Gly His
305                 310                 315

<210> SEQ ID NO 14
<211> LENGTH: 316
<212> TYPE: PRT
<213> ORGANISM: Homo sapiens

<400> SEQUENCE: 14

Met Gly Asn Arg His Ala Lys Ala Ser Ser Pro Gln Gly Phe Asp Val
1               5                   10                  15

Asp Arg Asp Ala Lys Lys Leu Asn Lys Ala Cys Lys Gly Met Gly Thr
            20                  25                  30

Asn Glu Ala Ala Ile Ile Glu Ile Leu Ser Gly Arg Thr Ser Asp Glu
        35                  40                  45

Arg Gln Gln Ile Lys Gln Lys Tyr Lys Ala Thr Tyr Gly Lys Glu Leu
    50                  55                  60

Glu Glu Val Leu Lys Ser Glu Leu Ser Gly Asn Phe Glu Lys Thr Ala
65                  70                  75                  80

Leu Ala Leu Leu Asp Arg Pro Ser Glu Tyr Ala Ala Arg Gln Leu Gln
                85                  90                  95

Lys Ala Met Lys Gly Leu Gly Thr Asp Glu Ser Val Leu Ile Glu Phe
            100                 105                 110

Leu Cys Thr Arg Thr Asn Lys Glu Ile Ile Ala Ile Lys Glu Ala Tyr
        115                 120                 125

Gln Arg Leu Phe Asp Arg Ser Leu Glu Ser Asp Val Lys Gly Asp Thr
    130                 135                 140

Ser Gly Asn Leu Lys Lys Ile Leu Val Ser Leu Leu Gln Ala Asn Arg
145                 150                 155                 160

Asn Glu Gly Asp Asp Val Asp Lys Asp Leu Ala Gly Gln Asp Ala Lys
                165                 170                 175

Asp Leu Tyr Asp Ala Gly Glu Gly Arg Trp Gly Thr Asp Glu Leu Ala
            180                 185                 190

Phe Asn Glu Val Leu Ala Lys Arg Ser Tyr Lys Gln Leu Arg Ala Thr
        195                 200                 205

Phe Gln Ala Tyr Gln Ile Leu Ile Gly Lys Asp Ile Glu Glu Ala Ile
    210                 215                 220
```

```
Glu Glu Glu Thr Ser Gly Asp Leu Gln Lys Ala Tyr Leu Thr Leu Val
225                 230                 235                 240

Arg Cys Ala Gln Asp Cys Glu Asp Tyr Phe Ala Glu Arg Leu Tyr Lys
            245                 250                 255

Ser Met Lys Gly Ala Gly Thr Asp Glu Glu Thr Leu Ile Arg Ile Val
            260                 265                 270

Val Thr Arg Ala Glu Val Asp Leu Gln Gly Ile Lys Ala Lys Phe Gln
        275                 280                 285

Glu Lys Tyr Gln Lys Ser Leu Ser Asp Met Val Arg Ser Asp Thr Ser
    290                 295                 300

Gly Asp Phe Arg Lys Leu Leu Val Ala Leu Leu His
305                 310                 315

<210> SEQ ID NO 15
<211> LENGTH: 505
<212> TYPE: PRT
<213> ORGANISM: Homo sapiens

<400> SEQUENCE: 15

Met Ser Tyr Pro Gly Tyr Pro Pro Pro Gly Gly Tyr Pro Pro Ala
1               5                   10                  15

Ala Pro Gly Gly Gly Pro Trp Gly Gly Ala Ala Tyr Pro Pro Pro
            20                  25                  30

Ser Met Pro Pro Ile Gly Leu Asp Asn Val Ala Thr Tyr Ala Gly Gln
            35                  40                  45

Phe Asn Gln Asp Tyr Leu Ser Gly Met Ala Ala Asn Met Ser Gly Thr
50                  55                  60

Phe Gly Gly Ala Asn Met Pro Asn Leu Tyr Pro Gly Ala Pro Gly Ala
65                  70                  75                  80

Gly Tyr Pro Pro Val Pro Pro Gly Gly Phe Gly Gln Pro Pro Ser Ala
                85                  90                  95

Gln Gln Pro Val Pro Pro Tyr Gly Met Tyr Pro Pro Gly Gly Asn
            100                 105                 110

Pro Pro Ser Arg Met Pro Ser Tyr Pro Pro Tyr Pro Gly Ala Pro Val
            115                 120                 125

Pro Gly Gln Pro Met Pro Pro Gly Gln Gln Pro Pro Gly Ala Tyr
130                 135                 140

Pro Gly Gln Pro Pro Val Thr Tyr Pro Gly Gln Pro Pro Val Pro Leu
145                 150                 155                 160

Pro Gly Gln Gln Gln Pro Val Pro Ser Tyr Pro Gly Tyr Pro Gly Ser
                165                 170                 175

Gly Thr Val Thr Pro Ala Val Pro Pro Thr Gln Phe Gly Ser Arg Gly
            180                 185                 190

Thr Ile Thr Asp Ala Pro Gly Phe Asp Pro Leu Arg Asp Ala Glu Val
            195                 200                 205

Leu Arg Lys Ala Met Lys Gly Phe Gly Thr Asp Glu Gln Ala Ile Ile
    210                 215                 220

Asp Cys Leu Gly Ser Arg Ser Asn Lys Gln Arg Gln Gln Ile Leu Leu
225                 230                 235                 240

Ser Phe Lys Thr Ala Tyr Gly Lys Asp Leu Ile Lys Asp Leu Lys Ser
                245                 250                 255

Glu Leu Ser Gly Asn Phe Glu Lys Thr Ile Leu Ala Leu Met Lys Thr
            260                 265                 270

Pro Val Leu Phe Asp Ile Tyr Glu Ile Lys Glu Ala Ile Lys Gly Val
            275                 280                 285
```

```
Gly Thr Asp Glu Ala Cys Leu Ile Glu Ile Leu Ala Ser Arg Ser Asn
        290                 295                 300

Glu His Ile Arg Glu Leu Asn Arg Ala Tyr Lys Ala Glu Phe Lys Lys
305                 310                 315                 320

Thr Leu Glu Glu Ala Ile Arg Ser Asp Thr Ser Gly His Phe Gln Arg
                325                 330                 335

Leu Leu Ile Ser Leu Ser Gln Gly Asn Arg Asp Glu Ser Thr Asn Val
            340                 345                 350

Asp Met Ser Leu Ala Gln Arg Asp Ala Gln Glu Leu Tyr Ala Ala Gly
        355                 360                 365

Glu Asn Arg Leu Gly Thr Asp Glu Ser Lys Phe Asn Ala Val Leu Cys
370                 375                 380

Ser Arg Ser Arg Ala His Leu Val Ala Val Phe Asn Glu Tyr Gln Arg
385                 390                 395                 400

Met Thr Gly Arg Asp Ile Glu Lys Ser Ile Cys Arg Glu Met Ser Gly
                405                 410                 415

Asp Leu Glu Glu Gly Met Leu Ala Val Val Lys Cys Leu Lys Asn Thr
            420                 425                 430

Pro Ala Phe Phe Ala Glu Arg Leu Asn Lys Ala Met Arg Gly Ala Gly
        435                 440                 445

Thr Lys Asp Arg Thr Leu Ile Arg Ile Met Val Ser Arg Ser Glu Thr
450                 455                 460

Asp Leu Leu Asp Ile Arg Ser Glu Tyr Lys Arg Met Tyr Gly Lys Ser
465                 470                 475                 480

Leu Tyr His Asp Ile Ser Gly Asp Thr Ser Gly Asp Tyr Arg Lys Ile
                485                 490                 495

Leu Leu Lys Ile Cys Gly Gly Asn Asp
            500                 505

<210> SEQ ID NO 16
<211> LENGTH: 323
<212> TYPE: PRT
<213> ORGANISM: Homo sapiens

<400> SEQUENCE: 16

Met Ala Ser Ile Trp Val Gly His Arg Gly Thr Val Arg Asp Tyr Pro
1               5                   10                  15

Asp Phe Ser Pro Ser Val Asp Ala Glu Ala Ile Gln Lys Ala Ile Arg
                20                  25                  30

Gly Ile Gly Thr Asp Glu Lys Met Leu Ile Ser Ile Leu Thr Glu Arg
            35                  40                  45

Ser Asn Ala Gln Arg Gln Leu Ile Val Lys Glu Tyr Gln Ala Ala Tyr
        50                  55                  60

Gly Lys Glu Leu Lys Asp Asp Leu Lys Gly Asp Leu Ser Gly His Phe
65                  70                  75                  80

Glu His Leu Met Val Ala Leu Val Thr Pro Pro Ala Val Phe Asp Ala
                85                  90                  95

Lys Gln Leu Lys Lys Ser Met Lys Gly Ala Gly Thr Asn Glu Asp Ala
                100                 105                 110

Leu Ile Glu Ile Leu Thr Thr Arg Thr Ser Arg Gln Met Lys Asp Ile
            115                 120                 125

Ser Gln Ala Tyr Tyr Thr Val Tyr Lys Lys Ser Leu Gly Asp Asp Ile
        130                 135                 140

Ser Ser Glu Thr Ser Gly Asp Phe Arg Lys Ala Leu Leu Thr Leu Ala
145                 150                 155                 160
```

Asp Gly Arg Arg Asp Glu Ser Leu Lys Val Asp Glu His Leu Ala Lys
            165                 170                 175

Gln Asp Ala Gln Ile Leu Tyr Lys Ala Gly Glu Asn Arg Trp Gly Thr
        180                 185                 190

Asp Glu Asp Lys Phe Thr Glu Ile Leu Cys Leu Arg Ser Phe Pro Gln
        195                 200                 205

Leu Lys Leu Thr Phe Asp Glu Tyr Arg Asn Ile Ser Gln Lys Asp Ile
210                 215                 220

Val Asp Ser Ile Lys Gly Glu Leu Ser Gly His Phe Glu Asp Leu Leu
225                 230                 235                 240

Leu Ala Ile Val Asn Cys Val Arg Asn Thr Pro Ala Phe Leu Ala Glu
                245                 250                 255

Arg Leu His Arg Ala Leu Lys Gly Ile Gly Thr Asp Gly Phe Thr Leu
                260                 265                 270

Asn Arg Ile Met Val Ser Arg Ser Glu Ile Asp Leu Leu Asp Ile Arg
            275                 280                 285

Thr Glu Phe Lys Lys His Tyr Gly Tyr Ser Leu Tyr Ser Ala Ile Lys
        290                 295                 300

Ser Asp Thr Ser Gly Asp Tyr Glu Ile Thr Leu Leu Lys Ile Cys Gly
305                 310                 315                 320

Gly Asp Asp

<210> SEQ ID NO 17
<211> LENGTH: 324
<212> TYPE: PRT
<213> ORGANISM: Homo sapiens

<400> SEQUENCE: 17

Met Phe Cys Gly Asp Tyr Val Gln Gly Thr Ile Phe Pro Ala Pro Asn
1               5                   10                  15

Phe Asn Pro Ile Met Asp Ala Gln Met Leu Gly Gly Ala Leu Gln Gly
            20                  25                  30

Phe Asp Cys Asp Lys Asp Met Leu Ile Asn Ile Leu Thr Gln Arg Cys
        35                  40                  45

Asn Ala Gln Arg Met Met Ile Ala Glu Ala Tyr Gln Ser Met Tyr Gly
    50                  55                  60

Arg Asp Leu Ile Gly Asp Leu Arg Glu Gln Leu Ser Asp His Phe Lys
65                  70                  75                  80

Asp Val Met Ala Gly Leu Met Tyr Pro Pro Leu Tyr Asp Ala His
                85                  90                  95

Glu Leu Trp His Ala Met Lys Gly Val Gly Thr Asp Glu Asn Cys Leu
            100                 105                 110

Ile Glu Ile Leu Ala Ser Arg Thr Asn Gly Glu Ile Phe Gln Met Arg
        115                 120                 125

Glu Ala Tyr Cys Leu Gln Tyr Ser Asn Asn Leu Gln Glu Asp Ile Tyr
    130                 135                 140

Ser Glu Thr Ser Gly His Phe Arg Asp Thr Leu Met Asn Leu Val Gln
145                 150                 155                 160

Gly Thr Arg Glu Glu Gly Tyr Thr Asp Pro Ala Met Ala Ala Gln Asp
                165                 170                 175

Ala Met Val Leu Trp Glu Ala Cys Gln Gln Lys Thr Gly Glu His Lys
            180                 185                 190

Thr Met Leu Gln Met Ile Leu Cys Asn Lys Ser Tyr Gln Gln Leu Arg
        195                 200                 205

```
Leu Val Phe Gln Glu Phe Gln Asn Ile Ser Gly Gln Asp Met Val Asp
        210                 215                 220

Ala Ile Asn Glu Cys Tyr Asp Gly Tyr Phe Gln Leu Leu Val Ala
225                 230                 235                 240

Ile Val Leu Cys Val Arg Asp Lys Pro Ala Tyr Phe Ala Tyr Arg Leu
                245                 250                 255

Tyr Ser Ala Ile His Asp Phe Gly Phe His Asn Lys Thr Val Ile Arg
                260                 265                 270

Ile Leu Ile Ala Arg Ser Glu Ile Asp Leu Leu Thr Ile Arg Lys Arg
                275                 280                 285

Tyr Lys Glu Arg Tyr Gly Lys Ser Leu Phe His Asp Ile Arg Asn Phe
                290                 295                 300

Ala Ser Gly His Tyr Lys Lys Ala Leu Leu Ala Ile Cys Ala Gly Asp
305                 310                 315                 320

Ala Glu Asp Tyr

<210> SEQ ID NO 18
<211> LENGTH: 338
<212> TYPE: PRT
<213> ORGANISM: Homo sapiens

<400> SEQUENCE: 18

Met Ala Pro Ser Leu Thr Gln Glu Ile Leu Ser His Leu Gly Leu Ala
1               5                   10                  15

Ser Lys Thr Ala Ala Trp Gly Thr Leu Gly Thr Leu Arg Thr Phe Leu
                20                  25                  30

Asn Phe Ser Val Asp Lys Asp Ala Gln Arg Leu Leu Arg Ala Ile Thr
                35                  40                  45

Gly Gln Gly Val Asp Arg Ser Ala Ile Val Asp Val Leu Thr Asn Arg
        50                  55                  60

Ser Arg Glu Gln Arg Gln Leu Ile Ser Arg Asn Phe Gln Glu Arg Thr
65                  70                  75                  80

Gln Gln Asp Leu Met Lys Ser Leu Gln Ala Ala Leu Ser Gly Asn Leu
                85                  90                  95

Glu Arg Ile Val Met Ala Leu Leu Gln Pro Thr Ala Gln Phe Asp Ala
                100                 105                 110

Gln Glu Leu Arg Thr Ala Leu Lys Ala Ser Asp Ser Ala Val Asp Val
                115                 120                 125

Ala Ile Glu Ile Leu Ala Thr Arg Thr Pro Gln Leu Gln Glu Cys
130                 135                 140

Leu Ala Val Tyr Lys His Asn Phe Gln Val Glu Ala Val Asp Gly Ile
145                 150                 155                 160

Thr Ser Glu Thr Ser Gly Ile Leu Gln Asp Leu Leu Ala Leu Ala
                165                 170                 175

Lys Gly Gly Arg Asp Ser Tyr Ser Gly Ile Ile Asp Tyr Asn Leu Ala
                180                 185                 190

Glu Gln Asp Val Gln Ala Leu Gln Arg Ala Glu Gly Pro Ser Arg Glu
                195                 200                 205

Glu Thr Trp Val Pro Val Phe Thr Gln Arg Asn Pro Glu His Leu Ile
        210                 215                 220

Arg Val Phe Asp Gln Tyr Gln Arg Ser Thr Gly Gln Glu Leu Glu Glu
225                 230                 235                 240

Ala Val Gln Asn Arg Phe His Gly Asp Ala Gln Val Ala Leu Leu Gly
                245                 250                 255

Leu Ala Ser Val Ile Lys Asn Thr Pro Leu Tyr Phe Ala Asp Lys Leu
```

```
                    260                 265                 270
His Gln Ala Leu Gln Glu Thr Glu Pro Asn Tyr Gln Val Leu Ile Arg
        275                 280                 285

Ile Leu Ile Ser Arg Cys Glu Thr Asp Leu Leu Ser Ile Arg Ala Glu
        290                 295                 300

Phe Arg Lys Lys Phe Gly Lys Ser Leu Tyr Ser Ser Leu Gln Asp Ala
305                 310                 315                 320

Val Lys Gly Asp Cys Gln Ser Ala Leu Leu Ala Leu Cys Arg Ala Glu
                325                 330                 335

Asp Met

<210> SEQ ID NO 19
<211> LENGTH: 25
<212> TYPE: DNA
<213> ORGANISM: artificial sequence
<220> FEATURE:
<223> OTHER INFORMATION: primer

<400> SEQUENCE: 19
gaagagctca gggccataaa acaag                                           25

<210> SEQ ID NO 20
<211> LENGTH: 32
<212> TYPE: DNA
<213> ORGANISM: artificial sequence
<220> FEATURE:
<223> OTHER INFORMATION: primer

<400> SEQUENCE: 20
catgctagct aagtcatcct cgcctccaca ga                                   32

<210> SEQ ID NO 21
<211> LENGTH: 30
<212> TYPE: DNA
<213> ORGANISM: artificial sequence
<220> FEATURE:
<223> OTHER INFORMATION: primer

<400> SEQUENCE: 21
tgtgctagcc aagccgtaaa caaattcaac                                      30

<210> SEQ ID NO 22
<211> LENGTH: 36
<212> TYPE: DNA
<213> ORGANISM: artificial sequence
<220> FEATURE:
<223> OTHER INFORMATION: primer

<400> SEQUENCE: 22
gcaggatccc tataccgagc tcgaattcgc gtctac                               36
```

DEVICE FOR BINDING A TARGET ENTITY TO A BAIT ENTITY AND DETECTION METHODS USING THE SAME

This is a nationalization of PCT/EP05/005320 filed May 12, 2005 and published in English, claiming benefit of U.S. provisional application No. 60/570,443 filed May 13, 2004.

FIELD OF THE INVENTION

The present invention relates generally to methods and devices for binding a target entity to a bait entity, as well as to the corresponding detection methods.

The methods and the devices of the invention are used in the industrial field for various purposes, such as i) in biomedical analysis, proteomics, genomics, biosensor and microarray technologies for assaying for the presence of a target entity (e.g. antigens, antibodies, cell proteins, cell membranes, ligand molecules, peptides, drugs, nucleic acids, sugar residues, lipids etc.), or ii) in pharmaceutical analysis for screening for target entities of interest, such as pharmaceutical candidate target molecules of interest that bind to a cell receptor of therapeutical interest, or iii) in biomedical and therapeutical applications for delivering therapeutical molecules of interest to target receptors, target cells or target organs of interest, in patients in need thereof.

BACKGROUND OF THE INVENTION

There is a need in the art for novel devices and novel methods that may allow improved detection of the binding of target entities, notably target molecules, onto bait entities, notably bait molecules, of interest, particularly bait proteins of interest, such as bait antibodies and various other bait receptor proteins or bait peptides, notably those of biologically relevance, including those of diagnostic and pharmacological relevance.

Notably, there is a need in the art to easy, low cost and high throughput methods for screening target candidate drug molecules that bind to, or are active against, therapeutically relevant bait molecules, notably bait proteins.

Current assays for the presence of an analyte in a solution, such as those commonly used for diagnostics, for instance, involve the use of a bait receptor molecule, notably an antibody, which has been raised against the target molecule, notably an antigen. Multianalyte assays known in the art involve the use of multiple bait receptor molecules, notably antibodies, and are directed towards assaying for multiple target analytes.

Automation and/or miniaturisation of binding assays are required if large numbers of target molecules are to be assayed simultaneously. Materials, surface coatings, and detection methods used for biomolecule assays are thus highly needed in the art.

There is also a need in the art for novel methods that may allow delivering therapeutically useful ingredients, notably drugs and pharmaceutically active molecules of interest, notably those of pharmacological and therapeutical relevance, to target entities, notably target cells and receptor molecules of interest. Current assays for delivering a drug of interest to target receptors of interest or target cells of interest involve the use of vectors, principally viral vectors and non-viral vectors, notably synthetic liposomes and polymers.

Delivering the therapeutical molecules of interest to target cells and receptors is problematic and requires controlled immobilization of specific bait entities to the targeting vectors, so that the immobilized bait entities are enabled to bind to target entities of interest.

Also, a recurrent technical problem that is encountered while manufacturing miniaturised biomolecule assay devices, notably protein assay devices, relates to a suitable binding of the "bait-receptor" molecule, notably a "bait-receptor" protein, so as to ensure a maximum availability of said "bait-receptor" molecule to the corresponding target molecules(s) of interest.

Available methods for linking the bait receptor molecule to the assay substrate make use of either 1) direct physical adsorption of the bait molecule or of molecules acting as receptors for the bait molecule to said substrate surface (e.g. Enzyme Linked ImmunoSorbent Assays, ELISA), or alternatively 2) chemical modification of the surface material of the substrate with linker molecules to which the bait molecule is bound, either covalently or non-covalently.

However, the above linking methods possess various technical drawbacks. Adsorbing the bait proteins directly onto the surface area of the substrate often causes an alteration of the structural conformation of said bait protein, which bait protein no more remains optimally available to its corresponding target molecules. In addition, direct adsorption of the bait protein or of molecules acting as receptors for the bait protein result in a random, uncontrolled, orientation of the bait protein, as well as in an uncontrolled surface density of the bait protein.

In addition, the use of covalent linkers between the surface area of the substrate and the bait receptor protein or molecules acting as receptors for the bait protein is complex and costly and results in an uncontrolled density of properly-oriented bait molecules for subsequent reactions. These drawbacks lead to a low ratio of correct binding of the bait proteins onto the selected substrate, in view of the initial amount of the bait protein material which is used.

There is thus a need in the art for improved biomolecule assay methods, notably protein assay methods, as well as corresponding devices.

Further, there is a need in the art for novel devices that are useful for the delivery of pharmaceutical molecules of interest to a target receptor, a target cell, a target tissue or a target organ in patients in need thereof.

SUMMARY OF THE INVENTION

A first object of the invention consists of a device for binding a target entity onto a bait entity that is immobilized on said device, said device comprising:
  a) a lipid layer which comprises one or more lipids, said lipid layer having a negative net charge in an aqueous solution at a neutral pH;
  b) a two-dimensional matrix of anchoring complexes that are bound to said lipid layer, wherein each of said anchoring complexes comprises:
    (i) a fusion complex comprising an Annexin protein fused to a partner molecule, wherein:
      said Annexin protein is bound to said lipid layer, and
      said partner molecule consists of an organic or a mineral compound;
    (ii) a bait molecule selected from the group consisting of:
      said partner molecule that is fused to said Annexin protein;
      a molecule that is covalently or non-covalently bound to said partner molecule;

a molecule that is indirectly bound to said partner molecule through one or more intermediate molecules that are covalently or non-covalently bound to said partner molecule.

In a device according to the present invention, said lipid layer may be selected from the group consisting of:
ai) a lipid bi-layer, including a lipid bi-layer coating a solid substrate;
aii) a lipid mono-layer, including a lipid mono-layer formed at the interface between air and an aqueous solution;
aiii) a liposome in an aqueous solution, including a liposome consisting of a vesicle with one or more lipid bi-layers enclosing an aqueous core.

By "fusion complex", it is intended herein a hybrid molecule that comprises, or consists of, an Annexin protein moiety that is covalently linked to a partner molecule, notably a protein, a peptide, or a nucleic acid. When said second molecule is a protein or a peptide, covalent linking with said Annexin moiety is performed either through a normal peptide bond via recombinant DNA technology methods or through a chemical bond, said chemical bond being either a normal peptide bond or any other chemical bond, via protein chemistry methods. Further, in said fusion complex, the Annexin protein may be either directly linked to said second molecule or may be separated from said second molecule by a spacer chain, notably an amino acid spacer chain having an amino acid length that may vary from 1 to 20 amino acid residues, most preferably hydrophilic amino acid residues.

In the device according to the invention, said two-dimensional matrix of anchoring complexes consists of a two-dimensional (2D) protein matrix that contains a fusion complex between an Annexin protein and a partner molecule, said partner molecule being preferably selected from the group consisting of a protein, a peptide, or a nucleic acid. Said 2D protein matrix results from the assembly of said Annexin moiety of said fusion complex on said lipid layer by specific and non-covalent binding. Said fusion complex is oriented and stably bound to said lipid layer.

In a device according to the invention, said bait molecule, is part of said anchoring complex, said anchoring complex consisting of
i) either the fusion complex as defined above, wherein the bait molecule is the partner molecule that is fused to said Annexin moiety of said fusion complex,
ii) or a complex between the fusion complex defined above and said bait molecule, wherein said bait molecule is bound, covalently or non-covalently, to the partner molecule of said fusion complex,
iii) or a complex between the fusion complex defined above, the bait molecule and intermediate molecules, said intermediate molecules binding both to said bait molecule and to the partner molecule of said fusion complex, when said bait molecule is linked to the partner molecule of said fusion complex via intermediate molecules.

When said lipid layer is:
ai) a lipid bi-layer coating a solid substrate;
aii) a lipid mono-layer formed at the interface between air and an aqueous solution,
another object of the invention consists of a system for detecting the binding of a target entity molecule onto a bait entity, wherein said system comprises a plurality of detection devices as defined above. This invention also relates to a method for detecting the binding of a target entity molecule onto a bait entity molecule, wherein said method comprises the steps of:
a) providing a sample to be tested;
b) bringing into contact the sample to be tested with a detection device or with a detection system as defined above; and
c) detecting the complexes eventually formed between (i) the bait entity (ies) contained in said detection device or in said detection system and (ii) the target entities eventually present within said tested sample.

When said lipid layer is:
ai) a lipid bi-layer coating a solid substrate;
aii) a lipid mono-layer formed at the interface between air and an aqueous solution,
this invention also pertains to a method for assaying for the presence of a target entity in a sample comprising the steps of:
a) providing an anchoring complex between an Annexin protein and a bait entity, which binds to said target entity
b) mixing the sample with said anchoring complex, whereby complexes between the bait moiety of said anchoring complex and the target molecule are allowed to be formed;
c) immobilizing the anchoring complexes obtained at step b), eventually under the form of complexes with said target entity, at the surface of a lipid layer, said lipid layer comprising a combination of (i) one or more lipids with (ii) one or more phospholipids, said one or more phospholipids having a negative net charge in an aqueous solution at a neutral pH;
d) detecting the complexes that are formed between the bait moiety of said anchoring complex and the target entity when said target entity is present in said sample.

When said lipid layer is a liposome in an aqueous solution, another object of the invention consists of a device for delivering entities notably drug and molecules, of pharmacological and therapeutical interest, to target entities, notably target cells and receptor molecules, of interest. Said device comprising:
a) liposomes comprising one or more lipid layers and an inner core containing one or more pharmaceutically active ingredients dissolved or suspended in an aqueous solution, wherein said lipid layer(s) comprise(s) one or more lipids and has a negative net charge in an aqueous solution at a neutral pH;
b) a two-dimensional matrix of anchoring complexes that are bound to the outer lipid layer, wherein each of said anchoring complexes comprises:
(i) a fusion complex comprising an Annexin protein fused to a partner molecule, wherein:
said Annexin protein is bound to said lipid layer, and
said partner molecule consists of an organic or a mineral compound;
(ii) a bait entity selected from the group consisting of:
said partner molecule that is fused to said Annexin protein;
a molecule that is covalently or non-covalently bound to said partner molecule;
a molecule that is indirectly bound to said partner molecule through one or more intermediate molecules that are covalently or non-covalently bound to said partner molecule.

Throughout the present description, it is disclosed the binding of a target entity, notably a target molecule, to a bait entity, notably a bait molecule, said bait entity being part of an anchoring complex containing an Annexin moiety, said anchoring complex being assembled as a 2D protein matrix stably bound, in an oriented manner, to a lipid layer surface via the specific interaction between the Annexin protein and negatively charged molecules, e.g. negatively charged phospholipids, contained in said lipid layer. The present invention is based on the intrinsic property of Annexin proteins, notably Annexin-A5, to form 2D protein matrices of high and well-defined density, including 2D crystalline assemblies (Mosser et al., 1991; Voges et al. 1994; Brisson et al., 1999; Oling et al., 2001; Reviakine et al., 1998), on lipid surfaces containing negatively charged phospholipids in the presence of calcium ions, said 2D protein matrices being stable, almost irreversibly bound, upon rinsing in calcium-containing buffer solutions (Govorukhina et al., 2002; Oling et al., 2001; Richter et al., submitted).

Three types of lipid layers are represented, respectively:

FIG. 1A: a lipid bi-layer coating a solid substrate;
FIG. 1B: a lipid mono-layer at the air-water interface;
FIG. 1C: a liposome in aqueous solution FIG. 2 illustrates a scheme of a specific embodiment of an assay device, also herein termed detection device, according to the invention, wherein the lipid layer consists of a lipid bi-layer coating a solid substrate, and wherein the Annexin protein consists of the Annexin-A5 protein.

Figure 1:
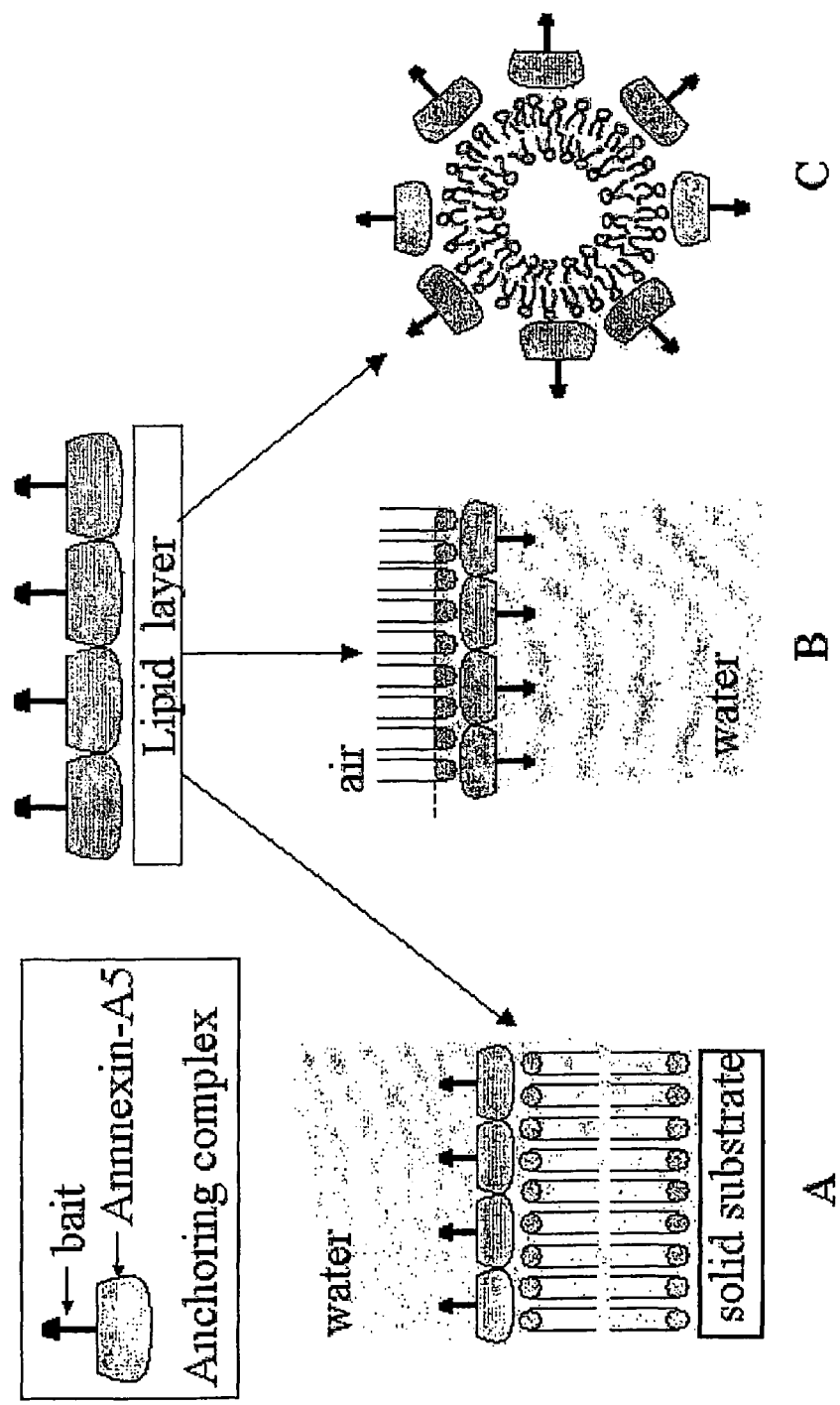
FIG. 1 illustrates a scheme of 2D assemblies of bait-anchoring complexes on lipid layers In the specific embodiment shown in FIG. 1, the anchoring complex consists of the bait molecule linked directly to an Annexin moiety, and said Annexin moiety consists of the Annexin-A5 protein.
Figure 2:
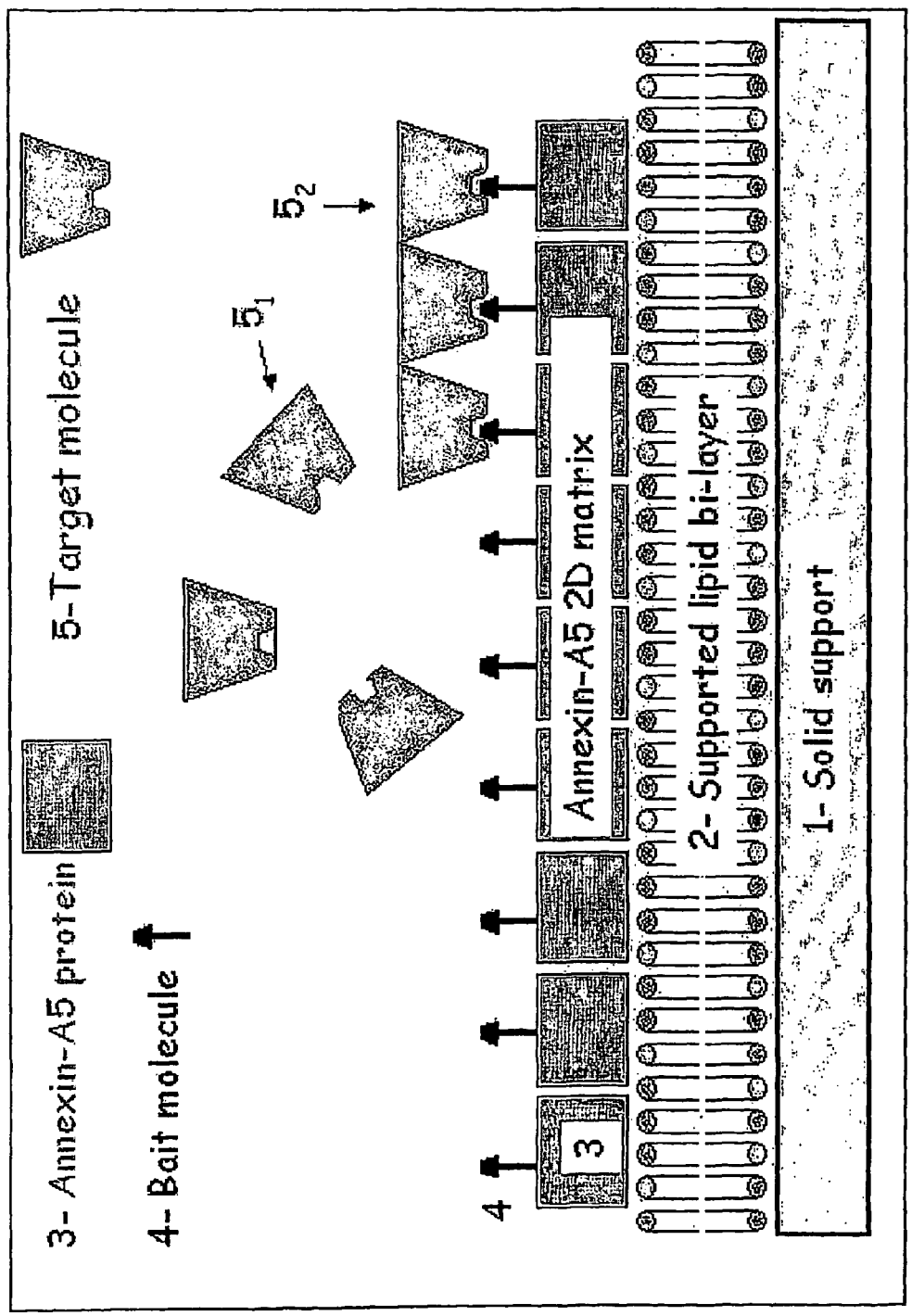

At the bottom of FIG. 1, there is represented the solid substrate (1) which is coated with a lipid bi-layer (2).

The Annexin-A5 moiety of the fusion complex (3) is bound to the external surface of the lipid bi-layer, forming a 2D self-assembled protein matrix. The bait molecule (4) is directly linked to said Annexin moiety of said fusion complex. There is also represented molecules of the target entity (5) which is tested, either as free target molecules in the liquid solvent ($5_1$), or as target molecules which are bound to bait molecules ($5_2$).

Figure 3:
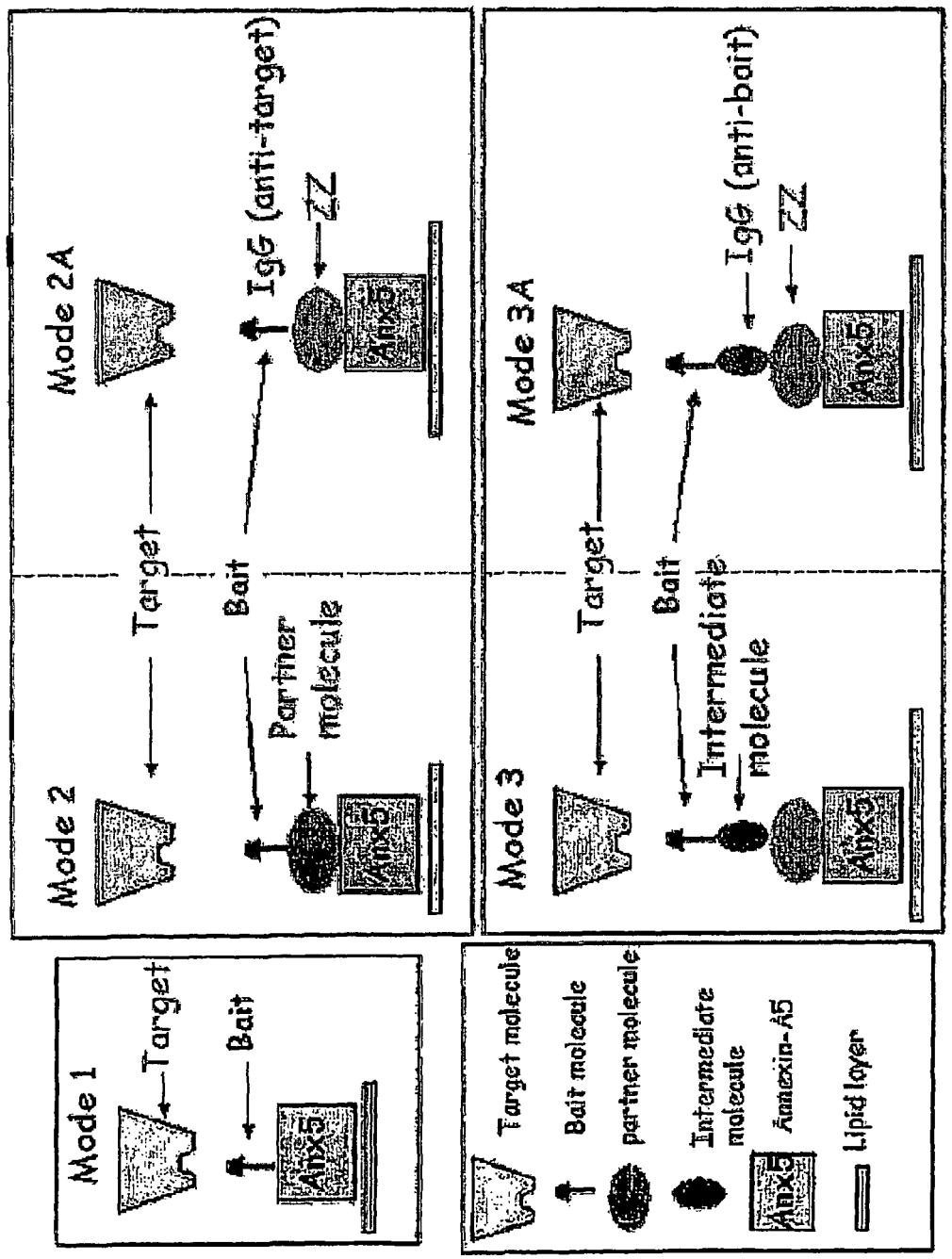

FIG. 3 illustrates a scheme of various modes of binding of a target molecule to a bait molecule that is part of an anchoring complex containing an Annexin-A5 protein moiety bound to a lipid layer.

Mode 1. The fusion complex consists of Annexin-A5 fused to the bait molecule.

Mode 2. The anchoring complex comprises:
a fusion complex consisting of an Annexin A5 protein fused to a partner molecule, and
the bait molecule which is bound to the partner molecule of said fusion complex.

Mode 3. The anchoring complex comprises:
a fusion complex consisting of an Annexin A5 protein fused to a partner molecule,
an intermediate molecule (i) that is bound by one side to the partner molecule of said fusion complex, and (ii) that is bound by another side to the bait molecule; and
the bait molecule that is bound to the intermediate molecule.

In Mode 2A and Mode 3A, an example of a preferred embodiment is shown, in which the fusion complex comprises the Annexin-A5 protein fused to the ZZ domain of protein A from *Staphylococcus aureus* (Loewenadler et al., 1987; Nilsson et al., 1987), by recombinant DNA technology:

In Mode 2A, the ZZ domain of protein A binds an IgG molecule, said IgG molecule being the bait molecule;
In Mode 3A, the ZZ domain of protein A binds an IgG molecule that is directed against the bait molecule. In this embodiment, the IgG molecule is an intermediate molecule between the fusion complex and the bait molecule.

Figure 4:
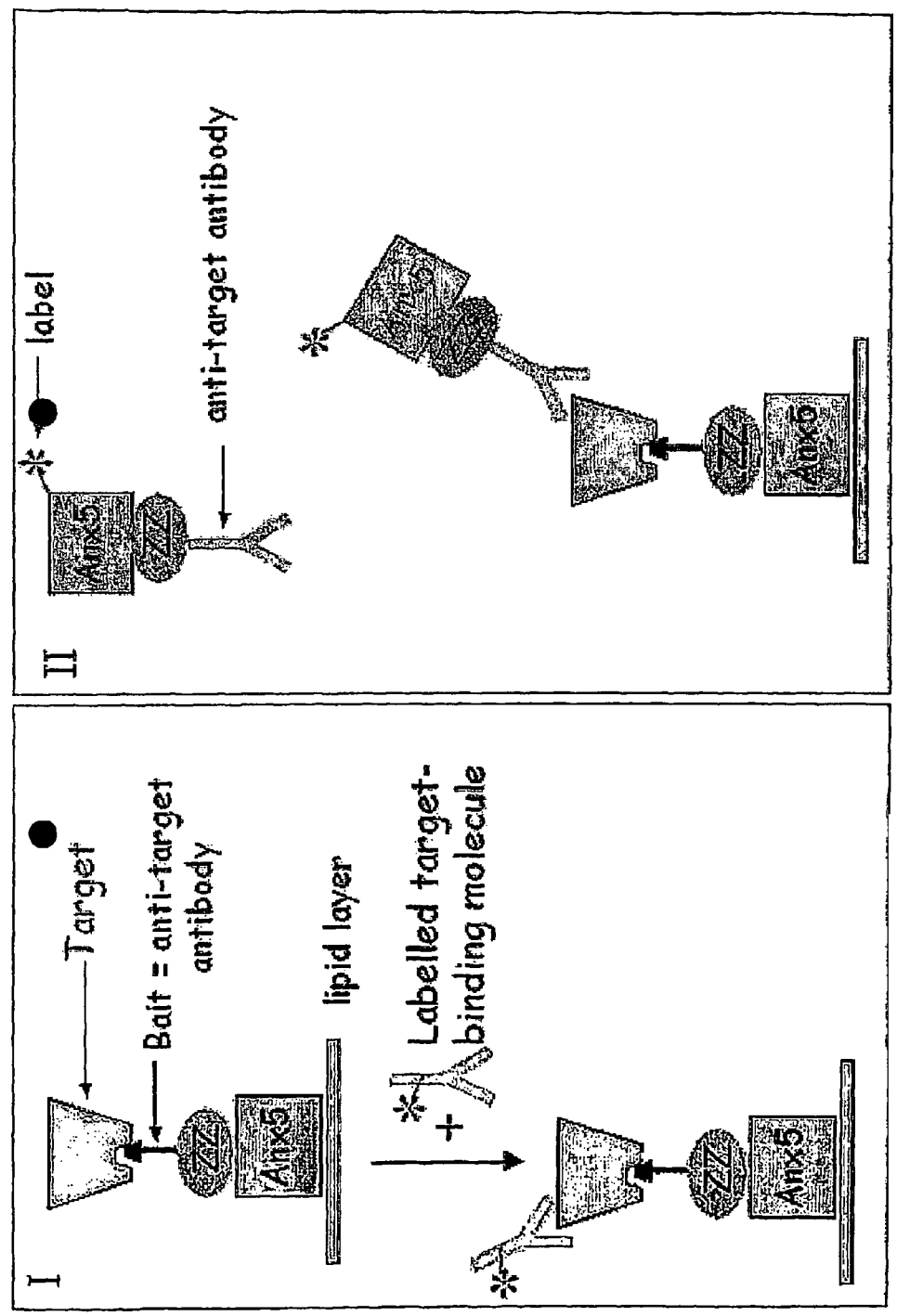

FIG. 4 illustrates a scheme of a specific embodiment of the detection of target molecules bound to bait molecules contained in a 2D matrix of anchoring complexes containing an Annexin-A5 moiety I—Scheme representing the use of a labelled target-binding molecule to detect target molecules bound to bait molecules that are part of an 2D matrix of Annexin-A5-containing anchoring complexes on a lipid layer, said lipid layer being: i) either a lipid bi-layer coating a solid substrate; or ii) a lipid mono-layer at the air-water interface. Annexin.

II—In a preferred embodiment, the target-binding molecule consists of a complex between an Annexin-A5-ZZ fusion protein and an anti-target antibody, said complex being labelled, notably fluorescently labelled, preferably at the level of the Annexin-A5-ZZ fusion protein moiety.

Figure 5:
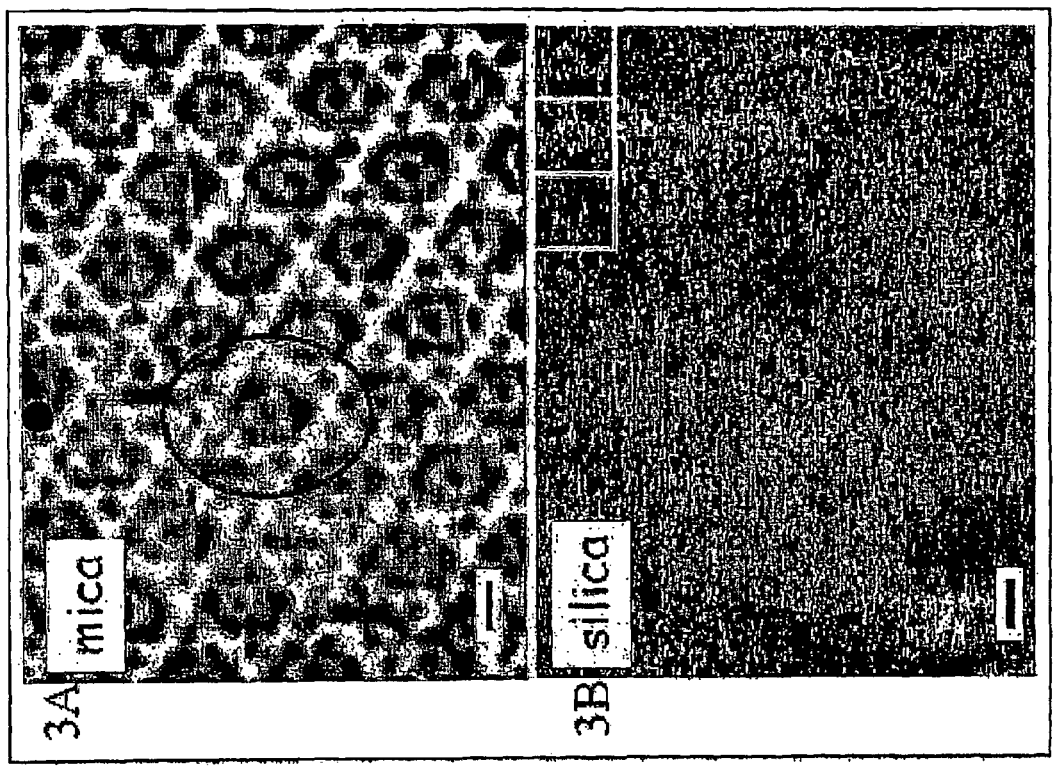
Figure 5:
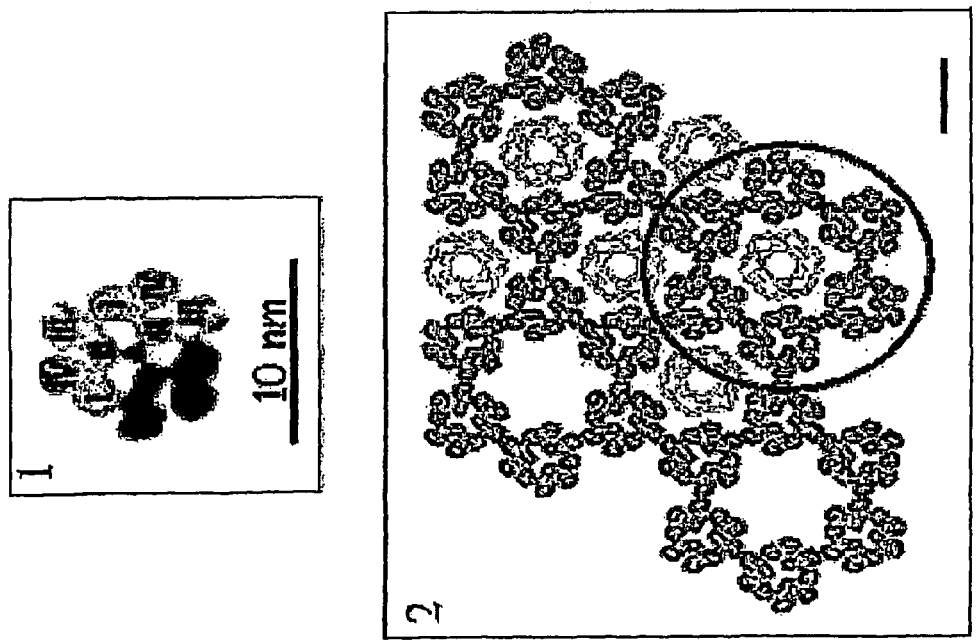

FIG. 5 illustrates the two-dimensional projected structure of the 2-D self-assemblies formed by Annexin-A5 on phospholipid surfaces.

1) Trimer of Annexin-A5 formed upon binding to a lipid surface containing negatively charged phospholipids, in the presence of calcium ions. An Annexin-A5 monomer is coloured in red. The four Annexin domains are numbered I to IV. Trimers of Annexin-A5 are found in 2D crystals with p6 symmetry (FIGS. 5-2,3A), in 2D crystals with p3 symmetry (not shown) and in high-density close-packed arrangements (FIG. 5-3B) (Mosser et al., 1991; Voges et al., 1994; Oling et al., 2001; Reviakine et al., 1998; Govorukhina et al., 2002; Richter and Brisson, 2003; Richter and Brisson, submitted).

2) On lipid mono-layers (here composed of the mixture DOPC:DOPS, 4:1, w:w) at the air-water interface, Annexin-A5 trimers form 2D crystals with p6 symmetry. The figure presents a 2D projection map of a p6 2D crystal of Annexin-A5, obtained by analysis of electron microscopy images (Oling et al., 2001). The blue circle surrounds six Annexin-A5 trimers located at the vertices of a hexagon, plus a central Annexin-A5 trimer.

3A) On a (DOPC:DOPS, 4:1, w:w) lipid bi-layer formed on a mica support, 2D crystalline assemblies with p6 symmetry are also observed by Atomic Force Microscopy (Reviakine et al., 1998).

3B) On a (DOPC:DOPS, 4:1, w:w) phospholipid bi-layer formed on a silica support, Annexin-A5 trimers form 2D high-density close-packed arrangements, as shown by Atomic Force Microscopy (Richter and Brisson, 2003).

Scale bars: 10 nm.

Figure 6:
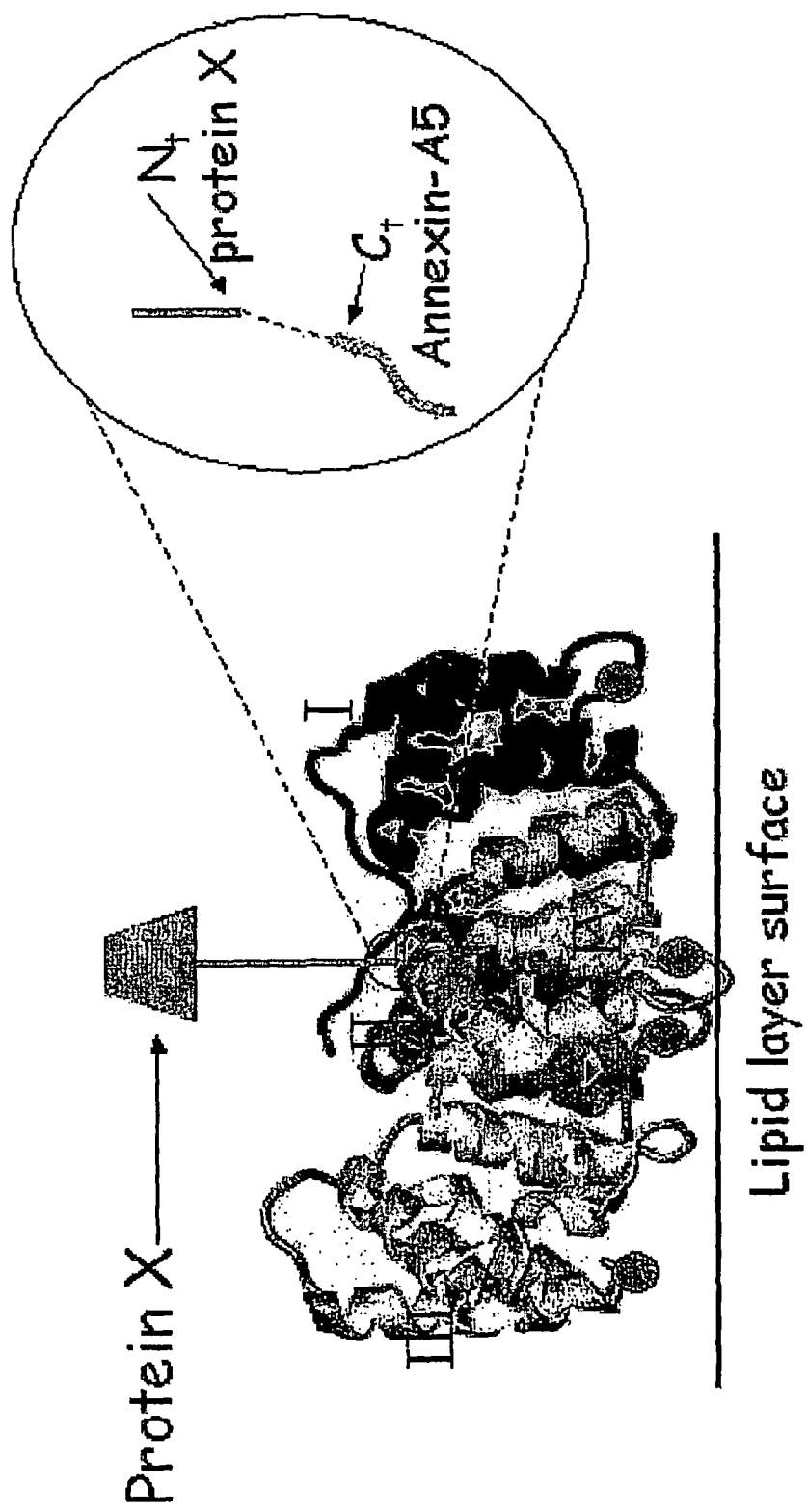

FIG. 6—Model of a fusion complex between Annexin-A5 and a second protein, named Protein X, obtained by recombinant DNA technology methods In the example shown here, the fusion complex is formed of Annexin-A5 fused at its C-terminal end to the N-terminal end of protein X, with a short linker sequence separating the 2 proteins (dashed segment).

Figure 7:
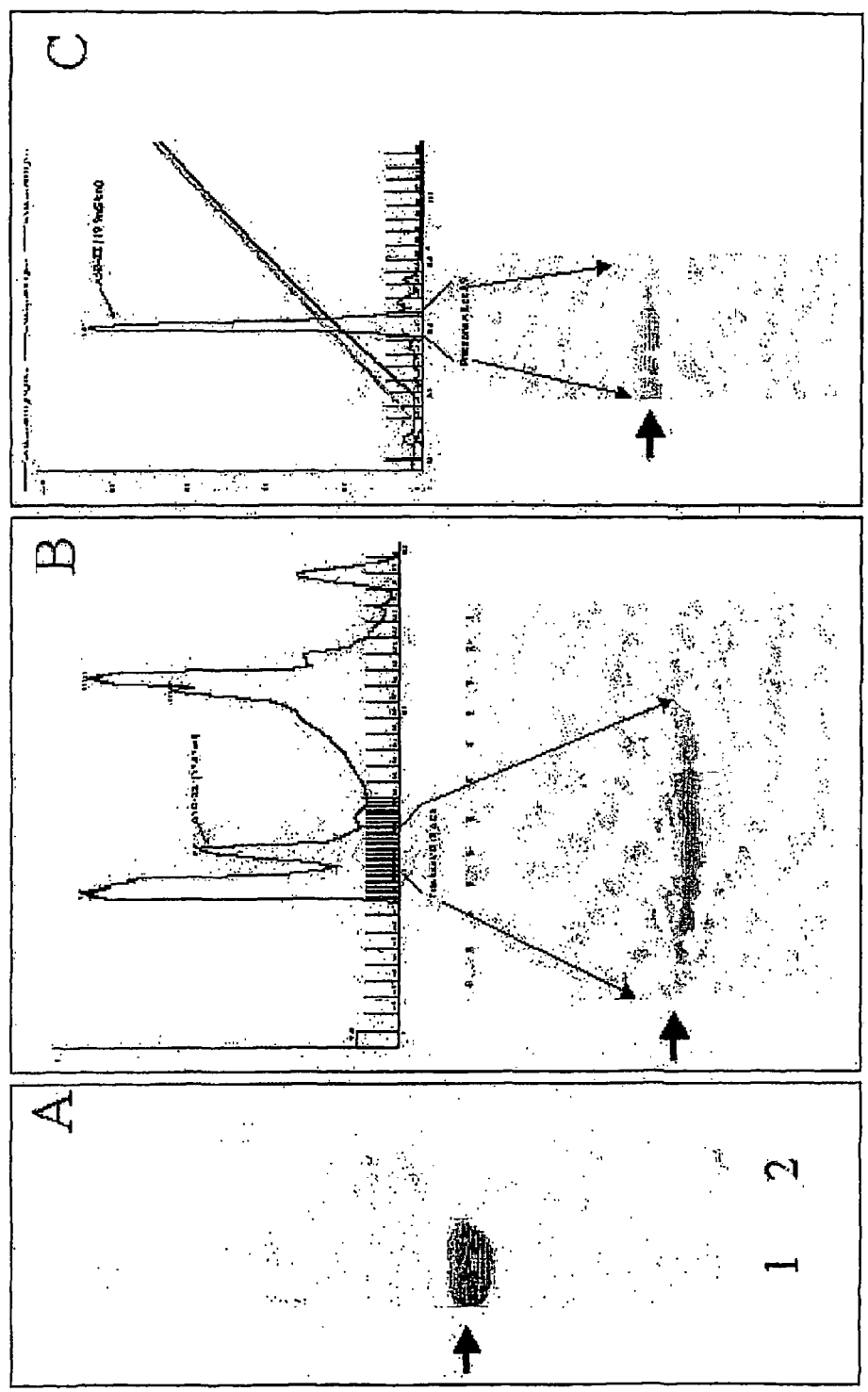

FIG. 7—Expression and purification of the fusion complex Annexin-A5-ZZ, by SDS-PAGE analysis A—Lane 1: Cell Soluble Extract (2 μL). The Annexin-A5-ZZ fusion protein, indicated by the arrow, migrates at an apparent MW of 42 kDa (theoretical MW: 50,074 Da). Lane 2: molecular weight markers.

B—Purification of Annexin-A5-ZZ fusion protein by gel filtration with a Superdex 75 column (Amersham Biosciences). The Annexin-A5-ZZ fusion protein (arrow) elutes in a sharp peak.

C—Purification of Annexin-A5-ZZ fusion protein by Mono-Q anion exchange chromatography. Pure fractions of the Annexin-A5-ZZ fusion protein (arrow) elute at ~270 mM NaCl.

Figure 8:
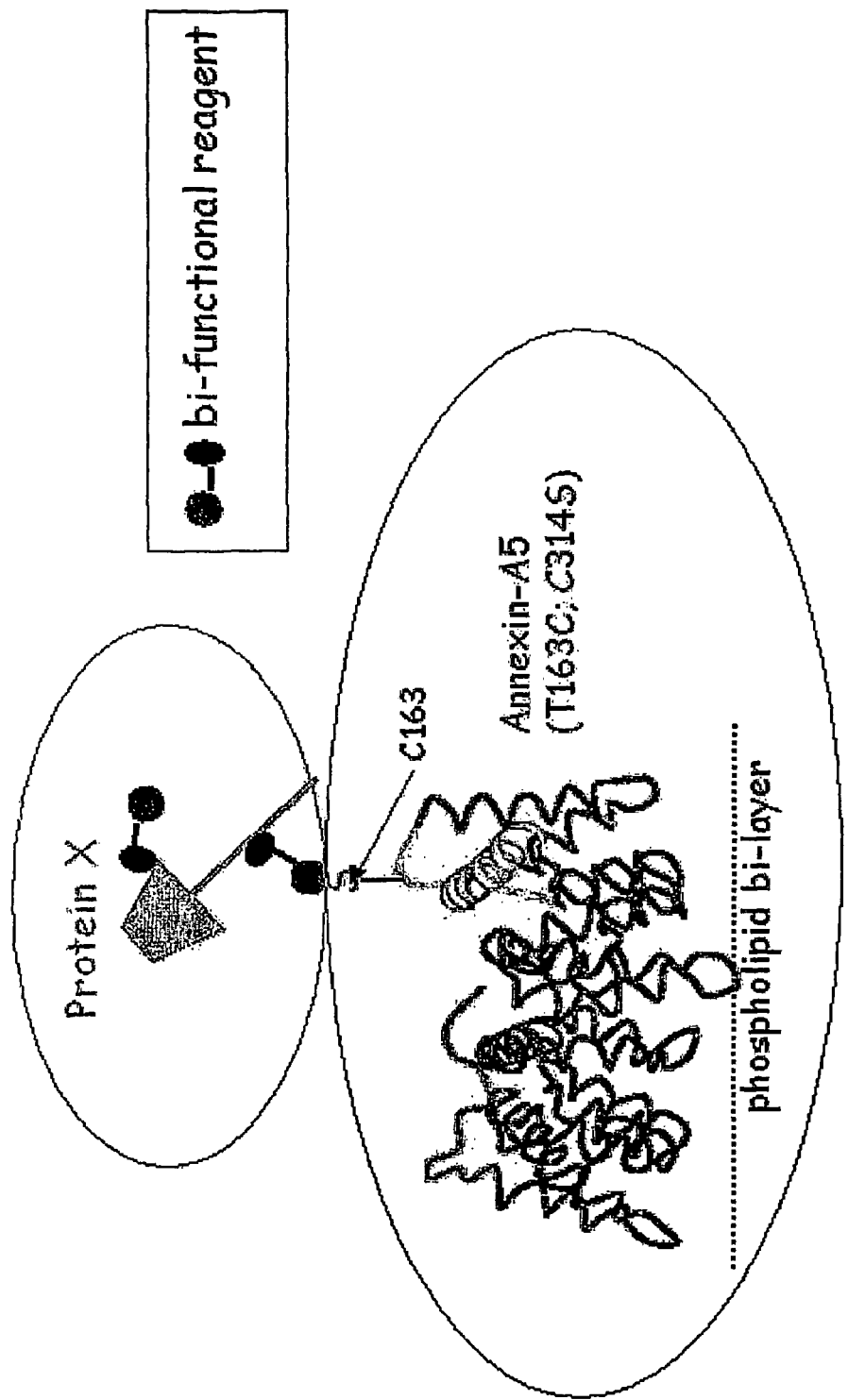

FIG. 8—Model of a fusion complex between Annexin-A5 and Protein X, by chemical cross-linking.

In the example shown here, the fusion protein is formed by covalent cross-linking between a mutated form of Annexin-A5 (T163C; C314S), which presents a single sulfhydryl group located at amino-acid position 163, and protein X, said protein X being previously activated by the hetero-bi-functional cross-linker N-succinimidyl 3-(2-pyridyldithio)propionate (SPDP) (Pierce).

The double mutant (T163C; C314S) Annexin-A5 presents all known lipid-binding properties characteristic of Annexin-A5 and in consequence the double-mutant (T163C; C314S) Annexin-A5 is called hereafter Annexin-A5.

As it is known, the N-succinimidyl group reacts with primary amines at alkaline pH (Wong, 1991). Upon mixing Annexin-A5-SH with 2-pyridyl-disulfide-activated protein X, a disulfide-bonded complex consisting of [Annexin-A5-S-S-Protein X] is formed.

Due to the non-specific nature of the reaction between SPDP and any protein, various types of [Annexin-A5-S-S-Protein X] complexes can be formed.

Other hetero-bi-functional cross-linkers, reacting with both primary amines and sulfhydryl groups, may be used instead of SPDP, such as SMTP, SULFO-LC-SMTP, LC-SPDP, SMCC, SULFO-SMCC, MBS, SULFO-MBS, SMPB, SULFO-SMPB (Pierce Biotechnology, USA).

Figure 9A:
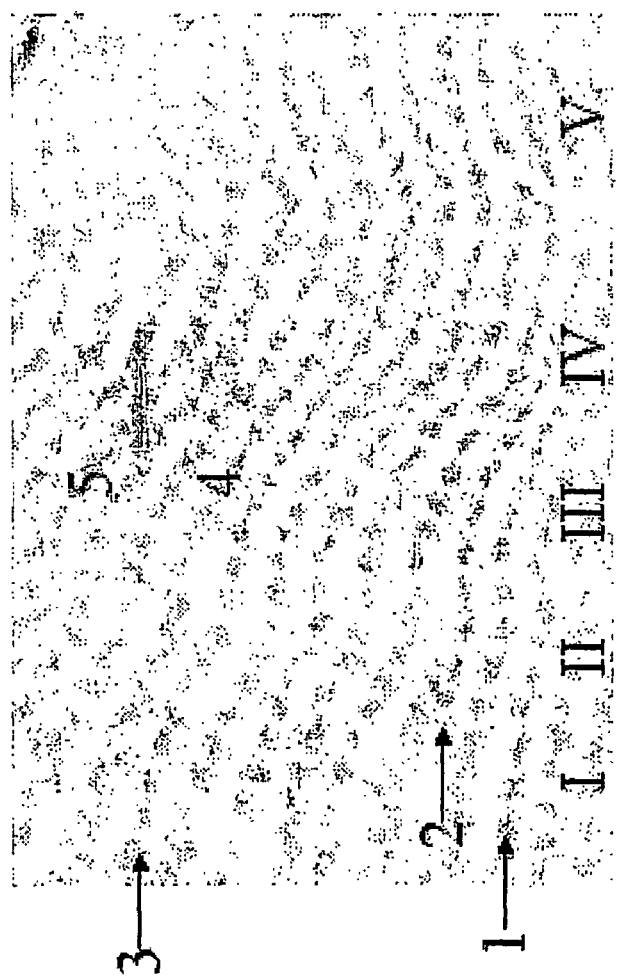
Figure 9B:
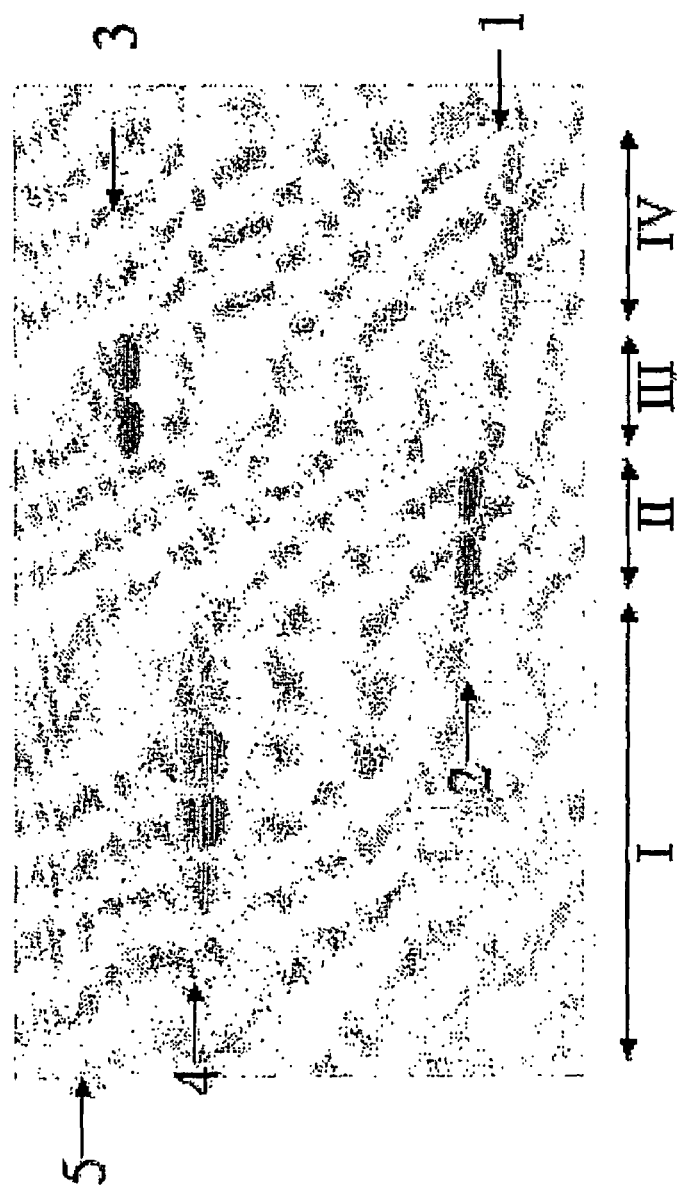

FIGS. 9A and 9B illustrate the production and the purification of a chemically cross-linked fusion complex between Annexin-A5 and protein G from *Streptococcus* sp.

FIG. 9A illustrates the production of fusion complexes between the double mutant Annexin A5 (T163C; C314S) and SPDP-modified protein G, by chemical cross-linking.

I: Annexin-A5B; II: Protein G; III: Protein G-SPDP; IV: Annexin-A5$_B$+ProteinG-SPDP; V: Annexin-A5$_B$+ProteinG-SPDP+β-mercapto-ethanol;

1: Annexin-A5$_B$; 2: Protein G; 3: Annexin-A5$_B$ dimer; 4: Fusion complex Annexin-A5$_B$-ProteinG; 5: Multimer Annexin-A5$_B$-Protein G.

It is to be noticed that Annexin-A5B means the double mutant of Annexin A5 (T163C; C314S).

FIG. 9B illustrates the purification of the [Annexin-A5$_B$-Protein G] fusion complexes, by gel filtration.

I: Fractions from $1^{st}$ peak; II: fractions from $2^{nd}$ peak; III: fractions from $3^{rd}$ peak; IV: fractions from $4^{th}$ peak.

1: Annexin-A5B; 2: Protein G; 3: (Annexin-A5B)$_2$=disulfide bonded dimer; 4: fusion complexes [Annexin-A5$_B$-Protein G]; 5 Multimer [Annexin-A5$_B$-Protein G].

FIGS. 10,11,12,13,14 illustrate detection assays using a detection device according to the invention. The detection method used here is the quartz crystal microbalance with dissipation monitoring (QCM-D) (Rodhal et al., 1995).

Figure 10:
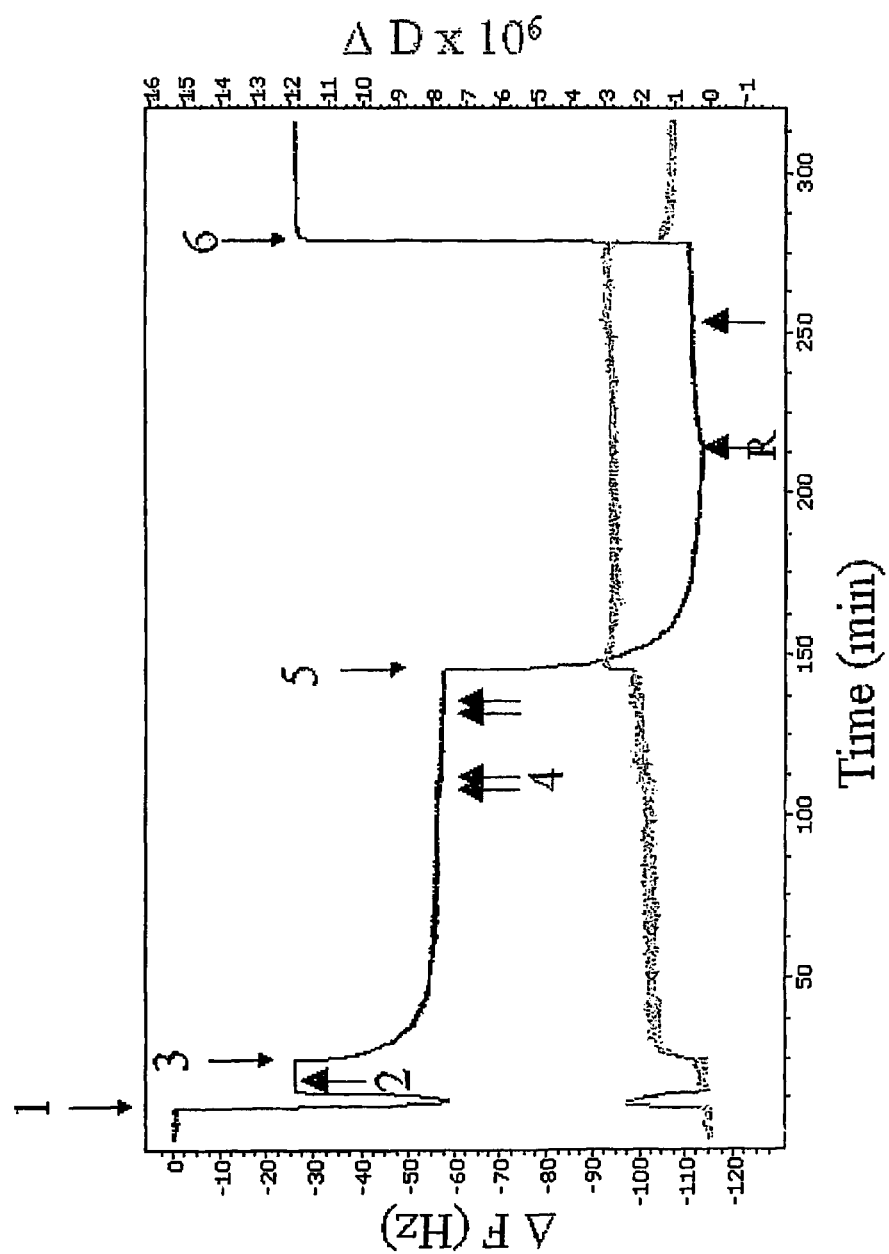

FIG. 10 illustrates the detection of the binding of IgG to a pre-formed 2D self-assembled matrix of Annexin A5-ZZ on [PC:PS (4:1)] SLB, by QCM-D.

Figure 11:
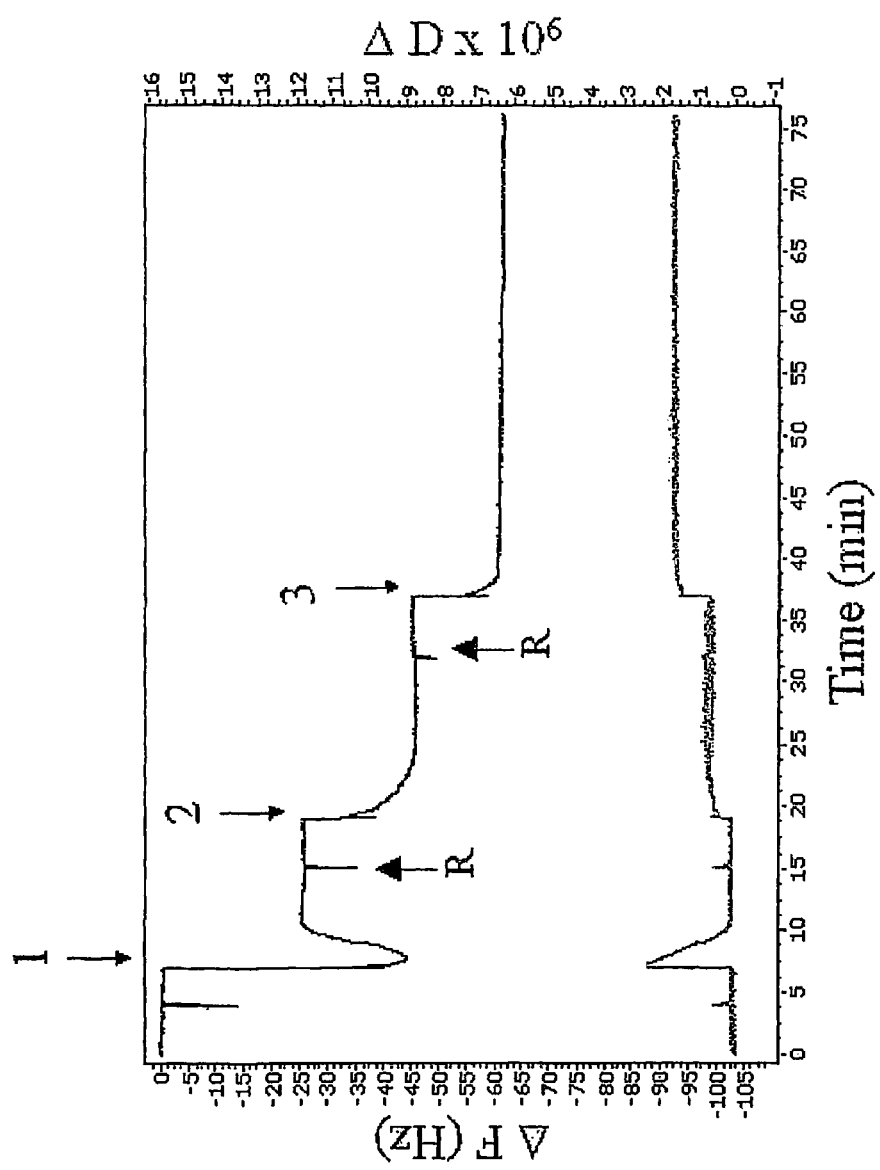

FIG. 11 illustrates the detection of the binding of IgG to a 2D self-assembled matrix of [Annexin A5/Annexin A-ZZ] on a [PC:PS (4:1)] SLB, by QCMD.

Figure 12:
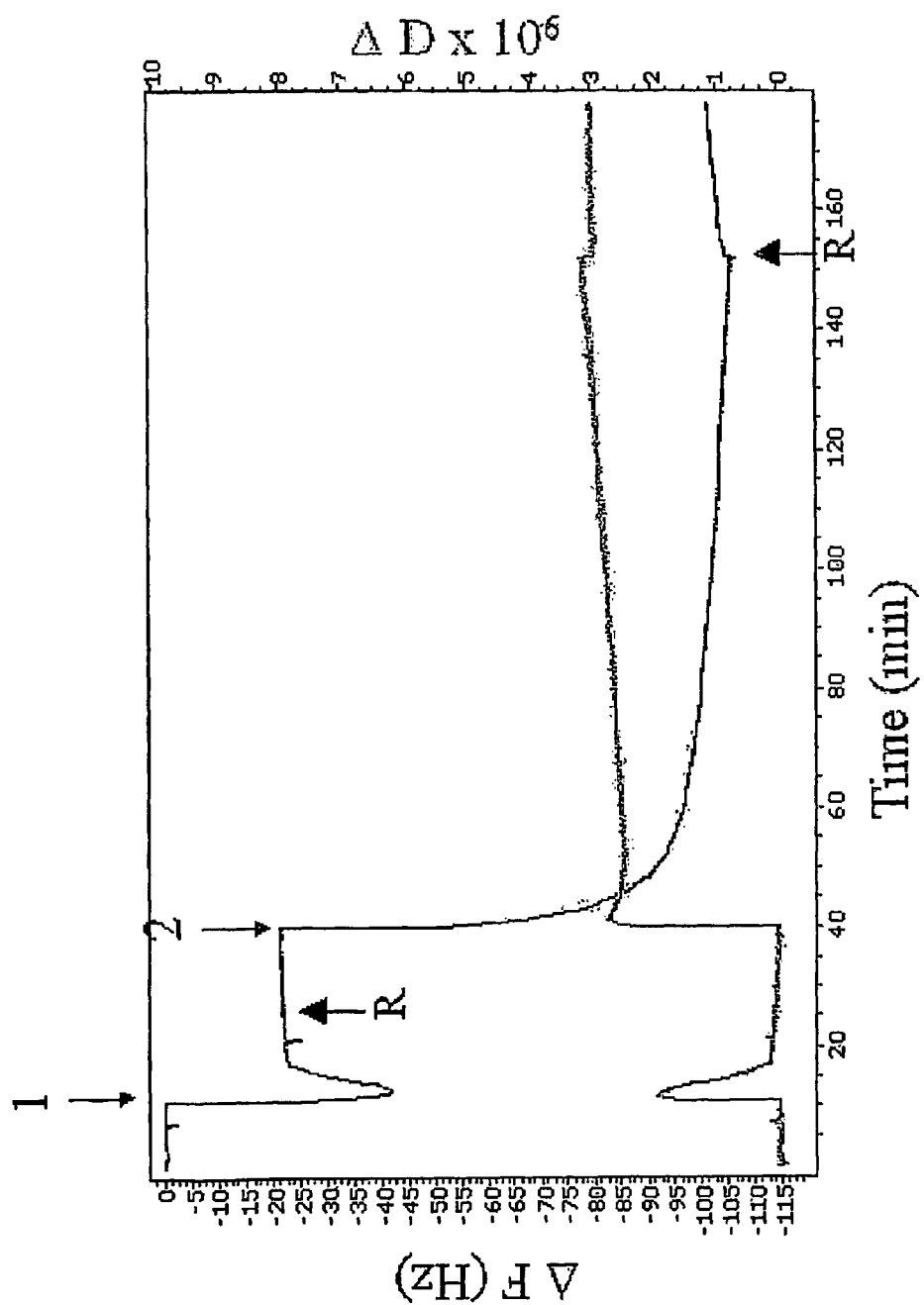

FIG. 12 illustrates the detection of the binding of complexes of [Annexin A5-ZZ/IgG), preformed in solution, on a [PC:PS (4:1)] SLB, by QCM-D.

Figure 13:
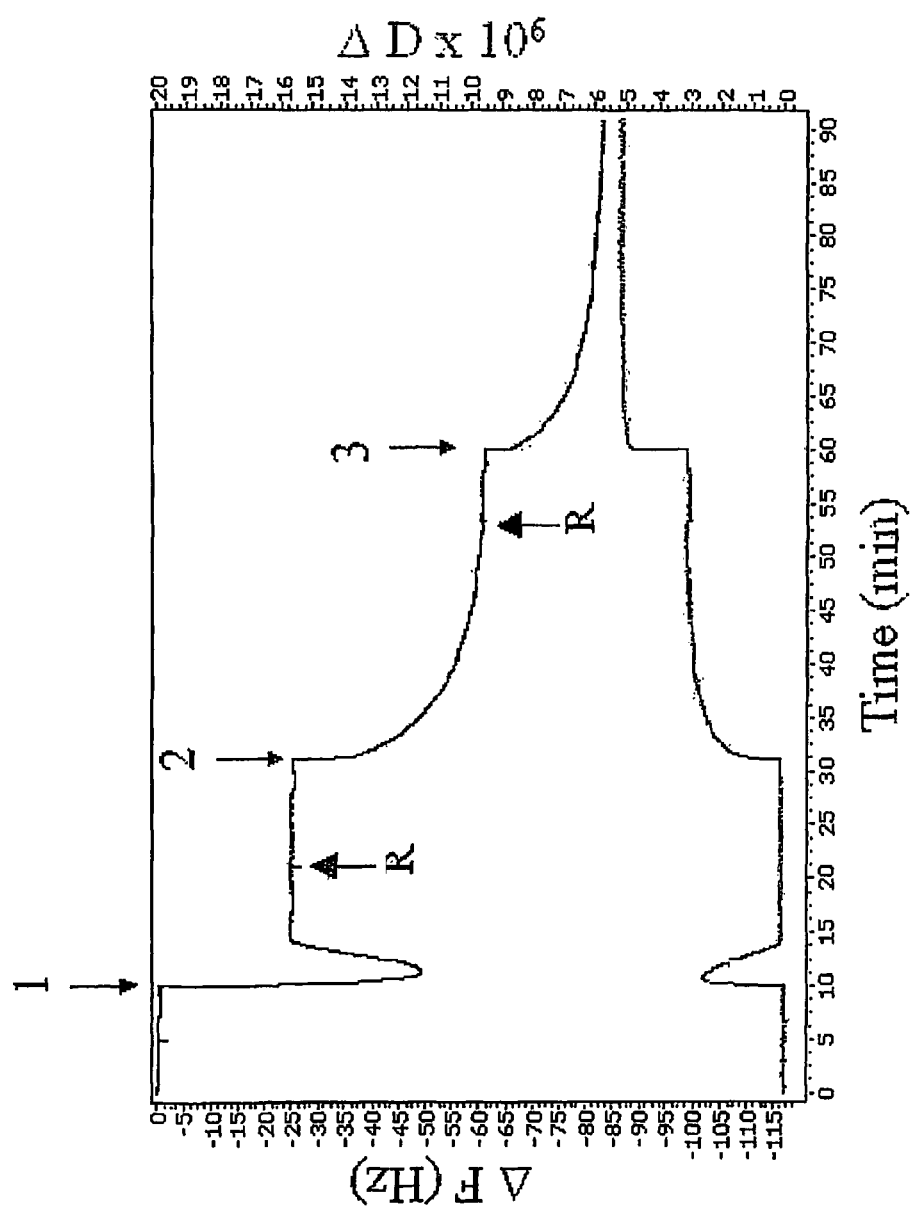

FIG. 13 illustrates the detection of the binding of IgGs to a 2D matrix of [Annexin A5$_B$-Protein G] cross-linked complexes on a [PC:PS (4:1)] SLB, by QCM-D.

Figure 14:
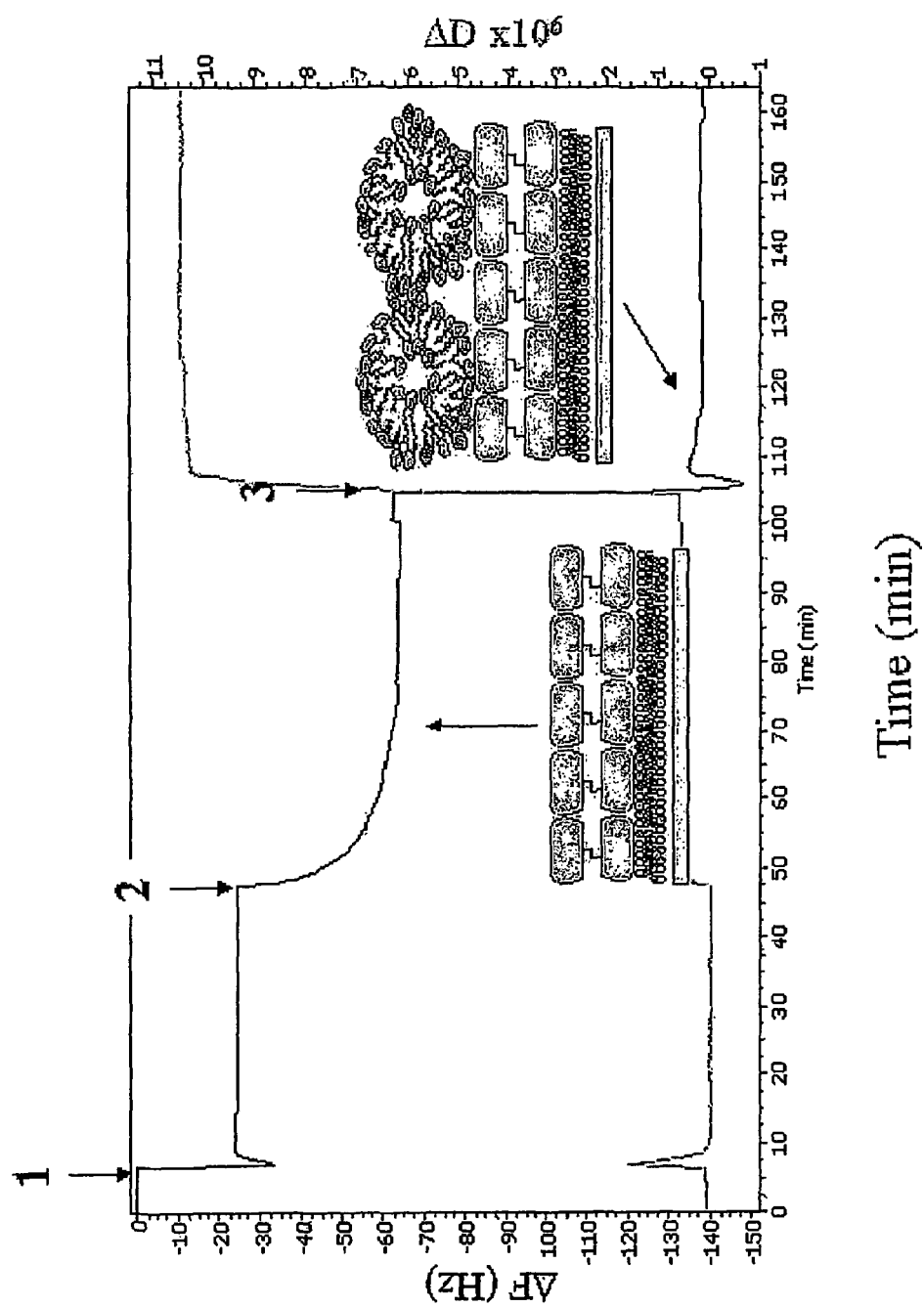

FIG. 14 illustrates the use of an anchoring complex [Annexin-A5-S-S-Annexin A5] for anchoring liposomes.

DETAILED DESCRIPTION OF THE INVENTION

The inventors have now designed new devices comprising a bait molecule that efficiently bind specifically to a target molecule.

More precisely, the inventors have designed new devices wherein target molecules specifically bind to bait molecules that are immobilized on said devices and wherein said bait molecules are comprised in anchoring complexes that are stably bound to a lipid layer.

Thus, the new devices of the invention may be used in various methods wherein the specific binding of a bait molecule to a target molecule is sought.

In certain embodiments, the new devices of the invention are used in methods wherein the detection of a specific binding event between a bait molecule and a target molecule is sought. Such embodiments include the use of a device according to the invention in methods for the screening of candidate target molecules that specifically bind to the bait molecules included in said devices.

In certain other embodiments, the new devices of the invention are used in methods wherein the specific binding of a bait molecule included in said device to a target molecule that is expressed at the cell membrane of a target cell is sought. Such embodiments include the use of a device according to the invention for performing the binding of said device on the cell membrane of a target cell in view of delivering one or more therapeutically useful molecules to said target cell.

An object of the invention consists of a device for binding a target entity onto a bait entity that is immobilized on said device, comprising:
a) a lipid layer which comprises one or more lipids, said lipid layer having a negative net charge in an aqueous solution at a neutral pH;
b) a two-dimensional matrix of anchoring complexes that are bound to said lipid layer, wherein each of said anchoring complexes comprises:
 (i) a fusion complex comprising an Annexin protein fused to a partner molecule, wherein:
  said Annexin protein is bound to said phospholipid layer, and
  said partner molecule consists of an organic or a mineral compound;
 (ii) a bait entity selected from the group consisting of:
  said partner molecule that is fused to said Annexin protein;
  a molecule that is covalently or non-covalently bound to said partner molecule;
  a molecule that is indirectly bound to said partner molecule through one or more intermediate molecules that are covalently or non-covalently bound to said partner molecule.

Thus, the inventors have now found that it can be performed improved binding and detection methods of target entities, notably target molecules, which make use of a device consisting of:
a) a lipid layer which comprises one or more lipids, said lipid layer having a negative net charge in an aqueous saline solution at a neutral pH;
said lipid layer, being:
 ai) a lipid bi-layer, e.g. a lipid bi-layer coating a solid substrate;
 aii) a lipid mono-layer, e.g. a lipid mono-layer formed at the interface between air and an aqueous solution;

aiii) a liposome in an aqueous solution, e.g. a liposome consisting of a vesicle with one or more lipid bi-layers enclosing an aqueous core;

b) a two-dimensional (2D) protein matrix that contains a fusion complex between an Annexin protein and a partner molecule, notably a protein, a peptide, or an nucleic acid.

Said 2D protein matrix resulting from the assembly of said Annexin moiety of said fusion complex on said lipid layer by specific and non-covalent binding.

Said fusion complex being oriented and stably bound to said lipid layer.

c) a bait molecule, is part of said anchoring complex, said anchoring complex consisting of:
i) either the fusion complex as defined above, wherein the bait molecule is the partner molecule that is fused to said Annexin moiety of said fusion complex,
ii) or a complex between the fusion complex defined above and said bait molecule, wherein said bait molecule is bound, covalently or non-covalently, to the partner molecule of said fusion complex,
iii) or a complex between the fusion complex defined above, the bait molecule and intermediate molecules that bind both to said bait molecule and to the partner molecule of said fusion complex, when said bait molecule is linked to the partner molecule of said fusion complex via intermediate molecules.

In certain embodiments, said anchoring complexes are non-covalently bound to said lipid layer.

In certain other embodiments, said anchoring complexes may be covalently bound to said lipid layer. Illustratively, covalent bounds may be generated between said anchoring complexes and lipid molecules comprised in said lipid layer subsequently to the formation of said two-dimensional matrix of anchoring complexes on said lipid layer. The one skilled in the art may use well-known techniques for generating covalent bonds between a protein and a lipid molecule. Illustratively, covalent bonds may be generated between alpha- or epsilon-groups of one or more lysine residues contained in the anchoring complexes, more specifically of the Annexin moiety of the anchoring complexes, and carboxyl groups comprised in the lipid molecules of said lipid layer.

The term "entity" is intended herein to encompass small molecules, biological molecules as well as supra-molecular assemblies, including notably cells, membrane vesicles and fragments derived from cells, natural or artificial liposomes, and inorganic particles.

According to the invention, generally, a bait entity consists of a bait protein, a peptide or an nucleic acid.

According to the invention, said Annexin protein comprised in said fusion complex preferably consists of an Annexin-A5 protein or a modified form of Annexin-A5.

The inventors have found that, using a fusion complex between (i) an Annexin protein and (ii) a partner molecule, the Annexin fusion complex presents the known properties of the Annexin-A5 protein per se to self-assemble into a stable, high-density 2D matrix, on a lipid layer.

Generally, in a device according to the invention, said partner molecule consists of a partner protein. Throughout the present specification, said partner protein may also be termed "second protein".

More specifically, the inventors have found that, using a fusion complex between (i) an Annexin-A5 protein and (ii) a second protein, the Annexin fusion complex presents the known properties of the Annexin-A5 protein per se to self-assemble into a stable, high-density 2D matrix, on a lipid layer.

In said fusion complexes, said partner molecule generally consists of an organic compound, and advantageously a polypeptide, i.e. a peptide or a protein.

In other embodiments of a fusion complex, said partner molecule may consist of a mineral molecule.

In certain embodiments, said lipid layer consists of a lipid bi-layer. These embodiments encompass a lipid bi-layer coating a solid substrate.

In certain other embodiments, said lipid layer consists of a lipid mono-layer. These embodiments encompass a lipid monolayer formed at the interface between air and an aqueous solution.

In still certain other embodiments, said lipid layer consists of the external lipid layer of a liposome in an aqueous solution. These embodiments encompass a lipid layer consisting of a liposome, said liposome consisting of a vesicle comprising one or more lipid bi-layers enclosing an aqueous core.

Further, the inventors have found that the fusion complexes made of either the Annexin-A5 protein fused to the ZZ domain of protein A from *Staphylococcus aureus* (Loewenadler et al., 1987; Nilsson et al., 1987) by recombinant DNA technology or the Annexin-A5 protein fused to a peptide containing the Arg-Gly-Asp (RGD) cell-adhesion sequence (Ruoslahti and Pierschbacher (1987), form 2D crystals on lipid mono-layers at the air-water interface and on solid-supported lipid bi-layers, said 2D crystals exhibiting p6 symmetry and geometrical characteristics similar to the 2D crystals formed by Annexin-A5 and described in Oling et al. (2001), Reviakine et al. (1998). In consequence, the self-assembly properties of Annexin-A5 which are responsible for the formation of trimers and of 2D crystals of trimers are conserved in the Annexin-A5-ZZ fusion complex.

Still further, the inventors have shown that the surface density of fusion complexes on the lipid layer can be adjusted by using mixtures of (i) fusion complexes and (ii) Annexin-molecules in a defined ratio of fusion complex molecules to Annexin molecules. Notably, the surface density of fusion complex molecules on the lipid layer may be adjusted by using mixtures of (i) fusion complex molecules and (ii) Annexin A5 molecules in a defined ratio of fusion complex molecules to Annexin A5 molecules.

The molecular ratio of fusion complex molecules to Annexin-A5 molecules in a lipid-bound 2D assembly of anchoring complexes is the same as the molecular ratio between these molecules in the aqueous mixture that serves as the starting material that is added to a pre-formed lipid layer. Consequently, the surface density of fusion complexes on said lipid layer is predetermined and controllable. The maximal surface density of Annexin-A5 is ~$3.3 \times 10^{12}$ molecules/cm$^2$ or ~200 ng/cm$^2$.

In a device according to the invention, the molecular ratio of (i) fusion complexes to (ii) non-fused Annexin molecules in the lipid-bound 2D assemblies of anchoring complexes can range from 1:0 to 0:1. However, preferably, said ratio ranges from 0.5:0.5 to 0.01:0.99, more preferably from 0.4:0.6 to 0.1:0.99 and most preferably from 0.3:0.7 to 0.1:0.9

Still further, the inventors have shown that the property of an Annexin protein, including an Annexin-A5 protein, to bind to lipid layers in the presence of calcium ions in a quasi-irreversible manner upon extensive rinsing with calcium-containing solutions is preserved for both fusion complexes and anchoring complexes.

Still further, the inventors have found that when an anchoring complex is included in said 2D protein matrix bound on the lipid layer, the bait molecule of said anchoring complex exhibits a high exposure to the solvent phase, and thus to any molecule contained in the solvent phase, that has the property to bind to said bait molecule.

Still further, the inventors have found that the 2D matrices of anchoring complexes consisting of Annexin-A5 linked to an RGD-containing peptide on a lipid bi-layer facilitate cell adhesion.

Still further, the inventors have found that the 2D matrices of anchoring complexes comprising disulfide-linked Annexin-A5 (T163C; C314S) dimers on lipid layers are able to anchor liposomes containing negatively charged phospholipids in the presence of calcium ions.

Thus, according to the invention, it has been manufactured a novel binding and detection device comprising a bait protein, said detection device taking benefit from the technical advantages of the Annexin-A5-based anchoring complex forming a 2D matrix on a lipid layer that are described above.

More precisely, the invention discloses a device for detecting the binding of a target molecule onto a bait molecule, wherein said bait molecule is immobilized on said device as part of an anchoring complex which comprises said fusion complex between an Annexin-A5 protein and a partner molecule, said fusion complex being bound on the lipid layer, said lipid layer consisting either i) of a lipid bi-layer coating a solid substrate; or ii) of a lipid mono-layer formed at the air-water interface.

As already mentioned, the inventors have found that there was a high availability of the partner molecule of the fusion complex as well as of the bait molecule of the anchoring complex to their corresponding ligand(s), due to the oriented binding of the fusion complex which is used, because the Annexin moiety is bound to the lipid layer through its convex side surface, whereas the partner molecule and the bait molecule are exposed to the solvent on the side of the Annexin moiety which is opposite to the side in contact with the lipid layer.

Further, a high surface density of the fusion complexes is allowed by the 2D self-assembly properties of the Annexin protein, when said protein is bound to the lipid layer.

Another object of the invention consists of a system for detecting the binding of a target entity molecule onto a bait entity, wherein said system comprises a plurality of detection devices as defined above.

Most preferably, according to the invention, the Annexin protein consists of an Annexin-A5 protein or a modified form of Annexin-A5.

In a first preferred embodiment, the lipid layer is a lipid bilayer coating a solid substrate, said solid substrate of the invention device may be of various types, provided it suitably allows the formation of a homogeneous lipid bi-layer coating. In said first embodiment of a device according to the invention, said solid substrate is part of the device.

Preferably, said solid substrate is selected from the group of substrates consisting of mica, silica, silicon, mineral glass and gold.

As a mica substrate, muscovite mica is preferred, such as that marketed by Company JBG-Metafix (Montdidier, France) under the reference) muscovite rubis mica, quality Clear-Scratch-Less CLSS As a silica substrate, silica-coated quartz crystals such as those marketed by Company Q-Sense (Gothenburg, Sweden) are preferred.

As a silicon substrate, a silicon wafer such as that marketed by the CEA (Grenoble, France) is preferred.

As mineral glass, microscope cover glass such as that marketed by the Company Fisher scientific (Pittsburgh, Pa., USA) is preferred.

A "lipid layer" according to the invention consists of a layer comprising lipid molecules and wherein said layer has a negative net charge in an aqueous solution at a neutral pH. Thus, said lipid layer comprises one or more kinds of compounds that impart to said lipid layer a negative net charge in an aqueous solution at a neutral pH. Compound(s) that impart a negative net charge in an aqueous solution at a neutral pH may consist of any compound having a negative net charge in an aqueous solution at a neutral pH. In certain embodiments of the lipid layer, the compounds that impart a negative net charge in an aqueous solution at a neutral pH consist of phospholipids having a negative net charge in an aqueous solution at a neutral pH. In certain embodiments, the compounds that impart a negative net charge in an aqueous solution at a neutral pH consist of polymers having a negative net charge in an aqueous solution at a neutral pH, such as polyphosphate-containing molecules, polysulfate-containing molecules, like heparin molecules or any polysulfate-containing derivativative of heparin.

By a "lipid mono-layer" according to the invention, it is intended a single lipid layer as defined above. In certain embodiments, said lipid monolayer is located at the interface between a liquid medium and air, said liquid medium preferably consisting of an aqueous or an hydrophilic liquid medium, such as water or any other aqueous solution included a saline water solution or any buffer aqueous solution.

By a "lipid bi-layer" according to the invention, it is intended a bi-layer comprising two lipid layers as defined above, said two lipid layers being associated, one with the other, through non-covalent interaction.

In certain embodiments, said lipid bi-layer comprises two lipid layers that consist respectively of:
  (i) a first molecular layer consisting of a lipid layer comprising a combination of (i) one or more amphiphilic molecules, most preferably one or more lipids, with (ii) one or more phospholipids, said one or more phospholipids having a negative net charge in an aqueous solution at a neutral pH, and wherein said lipid layer is bound, non-covalently, on one side to the solid substrate of the invention's device and on the opposite side to the second molecular layer of the bi-layer; and
  (ii) a second molecular layer consisting of a lipid layer comprising a combination of (i) one or more lipids with (ii) one or more phospholipids, said one or more phospholipids having a negative net charge in an aqueous solution at a neutral pH, and wherein said lipid layer is non-covalently bound on one side to the first molecular layer and wherein the opposite side of said lipid layer is exposed to the solvent and is bound by affinity to the Annexin moiety of the fusion complexes.

In a first preferred embodiment of a lipid layer, said lipid layer comprises, or even consists of, a lipid layer comprising a combination of (i) one or more lipids with (ii) one or more phospholipids, said one or more phospholipids having a negative net charge in an aqueous solution at a neutral pH. Preferred phospholipids having a negative net charge in an aqueous solution at a neutral pH are 1,2-dioleoyl-sn-glycero-3-phosphoserine (DOPS), 1-palmitoyl-2-oleoyl-sn-glycero-3-phosphoserine (POPS), 1,2-dioleoyl-sn-glycero-3-phosphatidic acid (DOPA), 1,2-dioleoyl-sn-glycero-3-phosphoglycerol (DOPG), cardiolipins.

In this first preferred embodiment of a lipid layer, said lipid layer comprises, or even consists of amphiphilic molecules with $C_{14}$ or longer alkyl or alkenyl chains, such as $C_{16}$, $C_{18}$, $C_{20}$. Preferred amphiphilic molecules are lipid molecules such as 1,2-dimyristoyl-sn-glycero-3-phosphocholine (DMPC), 1,2-dioleoyl-sn-glycero-3-phosphocholine (DOPC), 1-palmitoyl-2-oleoyl-sn-glycero-3-phosphocholine (POPC), egg lecithin, 1,2-dioleoyl-sn-glycero-3-phosphoserine (DOPS), 1-palmitoyl-2-oleoyl-sn-glycero-3-phosphoserine (POPS), 1,2-dioleoyl-sn-glycero-3-phosphatidic acid (DOPA), 1,2-dioleoyl-sn-glycero-3-phosphoglycerol (DOPG), cardiolipins, N-[1-(2,3-Dioleoxyloxy]propyl]-N,N,N-trimethylammonium methyl sulfate (DOTAP).

When a lipid bi-layer comprising two molecular layers as defined previously is used, then said first molecular layer is oriented with the hydrophilic part of the lipids interacting with the solid substrate and the extremity of the hydrophobic chains of the lipids being associated with the extremity of the hydrophobic chains of the second molecular layer. Said first embodiment of the lipid bi-layer is particularly suitable when the solid substrate which is used consists of mica, silica, silicon or mineral glass.

By a "phospholipid having a negative net charge", it is intended natural or synthetic phospholipids, such as 1,2-dioleoyl-sn-glycero-3-phosphoserine (DOPS), 1-palmitoyl-2-oleoyl-sn-glycero-3-phosphoserine (POPS), 1,2-dioleoyl-sn-glycero-3-phosphatidic acid (DOPA), 1-palmitoyl-2-oleoyl-sn-glycero-3-phosphatidic acid (POPA), 1,2-dioleoyl-sn-glycero-3-phosphoglycerol (DOPG), 1-palmitoyl-2-oleoyl-sn-glycero-3-phosphoglycerol (POPG), cardiolipins or a mixture of them such as brain lipid extracts.

Alternatively, negatively charged lipids like sulfatides may be used instead of phospholipids having a negative net charge.

The one or more phospholipids having a negative net charge in an aqueous solution at a neutral pH impart to the lipid layer the property of binding the Annexin moiety of the fusion complex. Notably, Annexin, particularly Annexin-A5, binds with a high affinity to such lipids that contain a phosphoserine group in the presence of calcium ions.

Most preferably, the phospholipids having a negative net charge in an aqueous solution at a neutral pH are selected from the group consisting of 1,2-di-myristoyl-sn-glycero-3-phosphoserine (DMPS), 1-palmitoyl-2-oleoyl-sn-glycero-3-phosphoserine (POPS), 1,2-dioleoyl-sn-glycero-3-phosphoserine (DOPS), 1,2-dioleoyl-sn-glycero-3-phosphoglycerol (DOPG) and cardiolipin. Most preferably, DOPS is used.

In the lipid layer, the content of said one or more phospholipids having a negative net charge in an aqueous solution at a neutral pH varies from 2% to 100% by weight, advantageously from 20% to 40% by weight, based on the total weight of said lipid layer.

The one skilled in the art may adapt the content of the lipid layer in said negatively charged phospholipids, depending on which solid substrate is used. For instance, the content in said negatively charged phospholipids varies preferably from 20% to 100% by weight, based on the total weight of the lipid layer, when mica is used as the solid substrate. In another illustrative example, the content in said negatively charged lipids varies preferably from 20% to 30% by weight, based on the total weight of the lipid layer, when silica is used as the solid substrate.

When the content in negatively charged phospholipids within the lipid layer is smaller than the lower limit range above, a 2D matrix of the fusion complexes of lower density is obtained, which may prohibit the manufacture of a detection device allowing a high detection sensitivity.

The other lipids that are comprised in the lipid layer may be phospholipids of various suitable types. These other phospholipids are preferably selected from the group consisting of lecithins including 1,2-dimyristoyl-sn-glycero-3-phosphocholine (DMPC), 1,2-dioleoyl-sn-glycero-3-phosphocholine (DOPC), 1-palmitoyl-2-oleoyl-sn-glycero-3-phosphocholine (POPC), egg lecithin.

In a most preferred embodiment, particularly when mica, silica, silicon or mineral glass is used as the solid substrate, the lipid layer consists of a mixture of 1,2-dioleoyl-sn-glycero-3-phosphoserine (DOPS) and 1,2-dioleoylsn-glycero-3-phosphocholine (DOPC).

According to said first preferred embodiment, a lipid bi-layer is formed by depositing lipid vesicles formed with lipids described above over a solid substrate, said lipid vesicles being prepared notably by sonication, as described under Example 5-1. Generally, the one skilled in the art will find suitable technical protocols for forming the lipid bi-layer from pre-formed phospholipid vesicles in the articles of Keller and Kasemo (1998); Richter et al. (2003), Richter and Brisson (2003) and Richter and Brisson (2005).

As already specified above, in certain embodiments of a device according to the invention, said lipid layer consists of a layer of phospholipid vesicles either adsorbed on the solid substrate, or bound to a 2D matrix of fusion complex made of a disulfide-linked complex of Annexin-A5 (T163C; C314S) bound to a phospholipid bi-layer.

In an alternative embodiment, the lipid bi-layer is replaced by negatively-charged polymers, polyphosphate-containing molecules, poly-sulfate-containing molecules, such as heparin molecules.

In yet another alternative embodiment, the lipid bi-layer is separated from the solid substrate by a cushion or a layer of polymer molecules (Sackmann and Tanaka, 2000).

As previously specified, certain embodiments of a lipid layer consist of a lipid mono-layer at the interface between air and an aqueous solution, In a specific embodiment of lipid mono-layer according to the invention, said lipid mono-layer consists of a mono-molecular layer consisting of a lipid layer comprising a combination of (i) one or more amphiphilic molecules, most preferably one or more lipids, with (ii) one or more phospholipids, said one or more phospholipids having a negative net charge in ad aqueous solution at a neutral pH, and wherein said lipid mono-layer is formed at the interface between air and an aqueous solution and is exposed to the solvent and is bound to the Annexin moiety of the fusion complexes.

In a first preferred embodiment of the lipid mono-layer, said mono-layer comprises, or even consists of a combination of (i) one or more lipids with (ii) one or more phospholipids, said one or more phospholipids having a negative net charge in an aqueous solution at a neutral pH. Preferred phospholipids having a negative net charge in an aqueous solution at a neutral pH are 1,2-dioleoyl-sn-glycero-3-phosphoserine (DOPS), 1-palmitoyl-2-oleoyl-sn-glycero-3-phosphoserine (POPS), 1,2-dioleoyl-sn-glycero-3-phosphatidic acid (DOPA), 1,2-dioleoyl-sn-glycero-3-phosphoglycerol (DOPG), cardiolipins.

In this first preferred embodiment of the lipid mono-layer, said mono-layer comprises, or even consists of amphiphilic molecules with $C_{14}$ or longer alkyl or alkenyl chains, such as $C_{16}$, $C_{18}$, $C_{20}$. Preferred amphiphilic molecules are lipid molecules such as 1,2-dimyristoyl-sn-glycero-3-phosphocholine (DMPC), 1,2-dioleoyl-sn-glycero-3-phosphocholine (DOPC), 1-palmitoyl-2-oleoyl-sn-glycero-3-phosphocholine (POPC), egg lecithin, 1,2-dioleoyl-sn-glycero-3-phosphoserine (DOPS), 1-palmitoyl-2-oleoyl-sn-glycero-3-phosphoserine (POPS), 1,2-dioleoyl-sn-glycero-3-phosphatidic acid (DOPA), 1,2-dioleoyl-sn-glycero-3-phosphoglycerol (DOPG), cardiolipins, N-[1-(2,3-Dioleoxyloxy]propyl]-N,N,N-trimethylammonium methyl sulfate (DOTAP).

According to said first preferred embodiment, said lipid mono-layer is oriented with the hydrophilic part of the lipids exposed to the aqueous solution with the hydrophobic chains of the lipids being exposed to air.

By a "phospholipid having a negative net charge", it is intended natural or synthetic phospholipids, such as 1,2-dioleoyl-sn-glycero-3-phosphoserine (DOPS), 1-palmitoyl-2-oleoyl-sn-glycero-3-phosphoserine (POPS), 1,2-dioleoyl-sn-glycero-3-phosphatidic acid (DOPA), 1-palmitoyl-2-oleoyl-sn-glycero-3-phosphatidic acid (POPA), 1,2-dioleoyl-sn-glycero-3-phosphoglycerol (DOPG), 1-palmitoyl-2-oleoyl-sn-glycero-3-phosphoglycerol (POPG), cardiolipins or a mixture of them such as brain lipid extracts.

Alternatively, negatively charged lipids like sulfatides may be used instead of phospholipids having a negative net charge.

The one or more phospholipids having a negative net charge in an aqueous solution at a neutral pH impart to the lipid mono-layer the property of binding the Annexin moiety of the fusion complex. Notably, Annexin, particularly Annexin-A5, binds with a high affinity to such lipids that contain a phosphoserine group in the presence of calcium ions.

Most preferably, the phospholipids having a negative net charge in an aqueous solution at a neutral pH are selected from the group consisting of 1,2-di-myristoyl-sn-glycero-3-phosphoserine (DMPS), 1-palmitoyl-2-oleoyl-sn-glycero-3-phosphoserine (POPS), 1,2-dioleoyl-sn-glycero-3-phosphoserine (DOPS), 1,2-dioleoyl-sn-glycero-3-phosphoglycerol (DOPG) and cardiolipin. Most preferably, DOPS is used.

In the lipid mono-layer, the content of said one or more phospholipids having a negative net charge in an aqueous solution at a neutral pH varies from 2% to 100% by weight, advantageously from 20% to 40% by weight, based on the total weight of said lipid mono-layer.

The one skilled in the art may adapt the content of the lipid mono-layer in said negatively charged phospholipids. For instance, the content in said negatively charged phospholipids varies preferably from 20% to 100% by weight, based on the total weight of the lipid mono-layer.

When the content in negatively charged phospholipids within the lipid mono-layer is smaller than the lower limit range above, a 2D matrix of the fusion complexes of lower density is obtained, which may prohibit the manufacture of a detection device allowing a high detection sensitivity.

The other lipids that are comprised in the lipid mono-layer may be phospholipids of various suitable types. These other phospholipids are preferably selected from the group consisting of lecithins including 1,2-dimyristoyl-sn-glycero-3-phosphocholine (DMPC), 1,2-dioleoyl-sn-glycero-3-phosphocholine (DOPC), 1-palmitoyl-2-oleoyl-sn-glycero-3-phosphocholine (POPC), egg lecithin.

In a most preferred embodiment, the lipid mono-layer consists of a mixture of 1,2-dioleoyl-sn-glycero-3-phosphoserine (DOPS) and 1,2-dioleoylsn-glycero-3-phosphocholine (DOPC).

According to the invention, the main advantageous properties of the Annexin moiety of the fusion complex are the capacity of forming high-density 2D protein matrices on phospholipid surfaces and the fact that said 2D protein matrices are stably bound to said phospholipid surfaces. In addition, the property of self-assembling into trimers and 2D crystalline assemblies based on trimers, as exhibited by Annexin-A5 and several other Annexins, including Annexin-A4 and Annexin-A12, provides additional advantages, like providing knowledge and control of the surface density of anchoring complexes. Annexin-A5 is preferred.

As it is widely known in the art, Annexin-A5 comprises four Annexin repetitive homology domains (Huber et al., 1990; Concha et al., 1993). It is also known that Annexins bind with high affinity to lipid surfaces containing negatively charged phospholipids in the presence of calcium ions (Tait et al., 1989; Blackwood and Ernst, 1990; Pigault et al., 1994; Meers, 1996). Annexin-A5 self-assembles spontaneously into Annexin-A5 trimers and into 2D crystalline arrangements, made of Annexin-A5 trimers, at the level of lipid mono-layers at the air-water interface (Mosser et al., 1991; Voges et al. 1994; Brisson et al., 1999), as well as at the level of solid-supported phospholipid bi-layers formed on mica (Reviakine et al., 1998; Richter and Brisson, 2005) (FIG. 5-2, 5-3A). It is also known that Annexin-A5 forms close-packed 2D self-assemblies of trimers on solid-supported phospholipid bi-layers formed on silica-coated silicon substrates (Richter and Brisson, 2003; Richter et al., 2005) (FIG. 5-3B).

By an "Annexin" protein it is intended herein a protein selected from the group consisting of Annexin-A1, Annexin-A2, Annexin-A3, Annexin-A4, Annexin-A5, Annexin-A6, Annexin-A7, Annexin-A8, Annexin-A9, Annexin-A12, Annexin-A, Annexin-B, Annexin-C and Annexin-D, as well as anyone of their "functionally active" protein derivatives.

By an "Annexin-A5" protein, it is intended herein a protein of the Annexin-A5 family, including Annexin-A5 from a species selected from the group consisting of *Rattus, Homo sapiens, Mus, Gallus* and *Bos*, as well as any one of their "functionally active" protein derivatives.

A "functionally active" derivative of an Annexin protein according to the invention encompasses any protein which is derived from any one the naturally occurring Annexin proteins, and which allows the formation of high-density 2D close packed assemblies of Annexin moieties which are stably bound to a phospholipid layer, especially to a phospholipid bi-layer.

The functionally active derivative of an Annexin protein also encompasses proteins having one or more amino-acid residue differences with regard to the amino acid sequence of the naturally occurring corresponding Annexin which is taken as the reference protein. A functionally active derivative of an Annexin protein also encompasses proteins that comprise one or more addition(s), substitution(s) or deletion(s) of one amino acid residue, compared to the reference Annexin-A5 protein, and wherein the modification(s) does not alter the formation of a 2D close packed arrangement of Annexin moieties which are stably bound to a phospholipid bi-layer.

A specific embodiment of a functionally active derivative of an Annexin-A5 protein is illustrated in the examples, said functionally active derivative being the mutated [T163C; C314S] Annexin-A5 protein, that derives from the naturally occurring Annexin-A5 from *Rattus norvegicus*.

The least homologous Annexin-A5 proteins among the group of those from *Rattus, Homo sapiens, Mus, Gallus* and *Bos* share 77% amino acid identity.

Preferably, an Annexin protein moiety which is part of one fusion complex according to the invention has at least 50% amino acid identity as regards the corresponding naturally occurring Annexin protein. More preferably, said Annexin protein moiety has at least 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% amino acid identity as regards the corresponding naturally occurring Annexin protein. As an illustrative example, generally, an Annexin functionally active derivative wherein the sole modifications consist of the deletion of the N-terminal sequence preceding the first repetitive region and of the C-terminal sequence following the fourth repetitive region has about 90% amino acid sequence identity as regards to the corresponding naturally occurring Annexin protein.

To determine the percentage of identity between two amino acid sequences, the sequence are aligned for optimal comparison purposes. For example, gaps can be introduced in one or both of a first and a second amino acid sequence for optimal alignment and non-homologous sequences can be disregarded for comparison purposes.

For optimal comparison purposes, the percent of identity of two amino acid sequences can be determined with CLUSTAL W (version 1.82) with the following parameters: (1) CPU MODE=ClustalW mp; (2) ALIGNMENT=<<full >>; (3) OUTPUT FORMAT=<<aln w/numbers>>; (4) OUTPUT ORDER <<aligned>>; (5) COLOR ALIGNMENT=<<no>>; (6) KTUP (word size)=<<default>>; (7) WINDOW LENGTH=<<default>>; (8) SCORE TYPE=<<percent>>; (9) TOPDIAG=<<default>>; (10) PAIRGAP=<<default>>; (11) PHYLOGENETIC TREE/TREE TYPE=<<none >>; (12) MATRIX=<<default>>; (13) GAP OPEN=<<default>>; (14) END GAPS=<<default>>; (15) GAP EXTENSION=<<default>>; (16) GAP DISTANCES=<<default >>; (17) TREE TYPE=<<cladogram>> et (18) TREE GRAP DISTANCES=<<hide>>.

Particularly preferred Annexin-A5 moieties that may be comprised in a fusion complex of the invention consist of the Annexin-A5 proteins selected from the group consisting of the amino acid sequences of SEQ ID No 1 to SEQ ID No 5 as well as their functionally active derivatives.

For illustratively defining the family of proteins which is encompassed by the functionally active derivatives of the Annexin-A5 proteins of SEQ ID No 1 to SEQ ID No 5, it is to be noted the following characteristics of the sequences below.

For the rat Annexin-A5 protein of SEQ ID No 1, the four repetitive regions are located, respectively, in the following defined regions: (i) 20-80, (ii) 92-152, (iii) 176-236 and (iv) 251-311.

For mouse the Annexin-A5 protein of SEQ ID No 2, the four repetitive regions are located, respectively, in the following defined regions (i) 21-81, (ii) 93-153, (iii) 177-237 and (iv) 252-312.

For the human Annexin-A5 protein of SEQ ID No 3, the four repetitive regions are located, respectively, in the following defined regions (i) 22-82, (ii) 94-154, (iii) 178-238 and (iv) 253-313.

For the bovine Annexin-A5 protein of SEQ ID No 4, the four repetitive regions are located, respectively, in the following defined regions (i) 22-82, (ii) 94-154, (iii) 178-238 and (iv) 253-313.

For the chicken Annexin-A5 protein of SEQ ID No 5, the four repetitive regions are located, respectively, in the following defined regions (i) 23-83, (ii) 95-155, (iii) 179-239 and (iv) 254-314.

An illustrative embodiment of an Annexin-A5 moiety as defined above consists of the rat-derived mutated [T163C; C314S] Annexin-A5 protein which is comprised in one fusion complex according to the invention, namely the fusion complex of SEQ ID No 6 herein, consisting of rat Annexin-A5 fused to the ZZ domain of protein A from *Staphylococcus aureus*).

As already mentioned in the present specification, an Annexin protein which is included in a fusion complex of the invention encompasses other Annexins than Annexin-A5 and may be selected among the group consisting of Annexin-1 (SEQ ID No 7), Annexin-2 (SEQ ID No 8), Annexin-3 (SEQ ID No 16), Annexin-4 (SEQ ID No 10), Annexin-6 (SEQ ID No 9), Annexin-7 (SEQ ID No 12), Annexin-8 (SEQ ID No 11), Annexin-9 (SEQ ID No 18), Annexin-A (SEQ ID No 17), Annexin-B (SEQ ID No 15), Annexin C (SEQ ID No 13), Annexin-D (SEQ ID No 14) as well as any one of their functionally active derivatives.

By "fusion complex", it is intended herein a hybrid molecule that comprises, or consists of, an Annexin protein moiety that is covalently linked to a second moiety, that is herein also termed "partner molecule", notably a protein, a peptide, or an oligonucleotide, When said partner molecule is a protein or a peptide, covalent linking with said Annexin moiety is effected either through a normal peptide bond via recombinant DNA technology methods or through a chemical bond, said chemical bond being either a normal peptide bond or any other chemical bond, via protein chemistry methods, as illustrated in FIGS. 6 and 7. Further, in said fusion complex, the Annexin protein may be either directly linked to said second molecule or may be separated from said second molecule by a spacer chain, notably an amino acid spacer chain having an amino acid length that may vary from 1 to 20 amino acid residues, most preferably hydrophilic amino acid residues.

In a fusion protein formed by recombinant DNA technology methods as defined in the present specification, the Annexin moiety is located either at the N-terminal end or in contrast at the C-terminal end of its amino acid sequence.

In one preferred embodiment, the Annexin moiety is located at the N-terminal end of said fusion protein, in which case the second protein is located at the C-terminal end of said fusion protein.

An illustrative example of a fusion complex produced by protein chemistry between the Annexin protein and the second protein is obtained through the cross-linking agent SPDP (N-succinimidyl 3-(2-pyridylthio)propionate).

As already mentioned in the present specification, in a device according to the invention, the bait molecule that is used has affinity for one or more target molecules, the presence of which is sought in the sample to be tested.

As already mentioned, said bait molecule is immobilized on the device as part of an anchoring complex comprising, or consisting of, the fusion protein between an Annexin protein and a partner molecule, notably a second protein.

In one embodiment, said anchoring complex consists exclusively of said fusion complex, in which embodiment the partner molecule which is fused with the Annexin-A5 protein consists of the bait molecule itself, in which case said bait molecule consists of a bait protein (FIG. 2-M*ode* 1).

In another embodiment, said anchoring complex comprises said fusion complex, wherein the partner molecule, e.g. the partner protein, contained in said fusion complex is, directly or indirectly, non-covalently bound to the said bait molecule. The partner molecule contained in the fusion complex is directly non-covalently bound to the said bait molecule when said bait molecule is simply non-covalently bound with said second protein (FIG. 2-M*ode* 2).

In still another embodiment, the partner molecule, e.g. the partner protein, contained in the fusion complex is indirectly non-covalently bound to the said bait molecule when said bait molecule is bound to an intermediate protein, said intermediate protein being itself directly or indirectly non-covalently bound to the second protein comprised in said fusion complex (FIG. 2-M*ode* 3).

In the embodiments above also, the bait molecule may consist of a bait protein.

In a preferred embodiment of the device according to the invention, in the fusion complex between the Annexin protein and a second protein, said second protein consists of a protein having affinity for the Fc moiety of an antibody.

Preferably, said protein having affinity for the Fc moiety of an antibody consists of the ZZ domain analogous to part of the protein A from *Staphylococcus aureus*, such as that described by Uhlen et al. (1990). Still preferably, said protein having affinity with the Fc moiety of an antibody consists of the G protein from *Streptococcus* sp., or of part of the G protein from *Streptococcus* sp, such as that described by Elliasson et al. (1988).

According to this preferred embodiment, the protein having affinity for the Fc moiety of an antibody may be the bait molecule, in which case the detection device allows the detection of the presence of antibodies in a sample to be tested.

Still according to this preferred embodiment, the second protein, consisting of a protein having affinity for the Fc moiety of an antibody, does not consist of the bait molecule, in which case the bait molecule may be either (i) an antibody which is directly bound on said second protein (FIG. 3-M*ode* 2A), or (ii) a bait molecule of interest which is bound to a bait-binding intermediate molecule (FIG. 3-M*ode* 3), notably a bait-specific antibody (FIG. 3-M*ode* 3A), said bait-binding intermediate molecule directly binds to said second protein (FIG. 3-M*ode* 3A).

In another preferred embodiment of the device according to the invention, in the fusion complex between the Annexin protein and a second protein, said second protein consists of an antibody fragment comprising the Complementary Determining Regions (CDRs) of an antibody.

According to this preferred embodiment, said antibody fragment may consist of the bait molecule itself, in which case the detection device allows detecting target molecules that have affinity with said antibody fragment.

Still according to this preferred embodiment, said antibody fragment consists of a bait-specific antibody fragment, to which the bait molecule is directly non-covalently bound.

In a preferred aspect of this preferred embodiment, said antibody fragment is selected from the group consisting of an Fab or a single-chain variable fragment (scFv) derived from a parent antibody.

In still another preferred embodiment of the detection device according to the invention, in the fusion complex between the Annexin protein and a second protein, said second protein consists of said bait molecule, which thus consists of a bait protein.

In another preferred embodiment of the detection device according to the invention, said anchoring complex consists of:
 (i) a fusion complex between an Annexin-A5 protein and an antibody fragment comprising the CDR domain of a bait-specific antibody; and
 (ii) the bait molecule which is non covalently bound to the bait-specific antibody fragment of said fusion complex. Said bait molecule may consist of a bait protein.

In still a further embodiment of the detection device according to the invention, said anchoring complex consists of:
 (i) a fusion complex between an Annexin protein and a protein having affinity for the Fc portion of an antibody; and
 (ii) an antibody which is non-covalently bound by its Fc domain onto said fusion complex, said antibody being said bait molecule.

In yet a further embodiment of the detection device according to the invention, said anchoring complex consists of:
 (i) a fusion complex between an Annexin protein and a protein having affinity for the Fc portion of an antibody;
 (ii) a bait-specific antibody which is non-covalently bound by its Fc domain onto said fusion complex; and
 (iii) the bait molecule which is non-covalently bound onto said bait-specific antibody. Said bait molecule may consist of a bait protein.

In yet a further embodiment of the detection device according to the invention, said anchoring complex consists of:
 (i) a fusion complex between an Annexin protein and a protein which is the bait protein In yet a further embodiment of the detection device according to the invention, said anchoring complex consists of:
 (i) a fusion complex between an Annexin protein and a second protein having affinity for the bait molecule
 (ii) the bait molecule which is bound to said second protein. Said bait molecule may consist of a bait protein Preferably, in a detection device according to the invention, said bait molecule is selected from the group consisting of biological molecules, their derivatives, and their assemblies as well as from the group of organic molecules as well as from the group of polymers as well as from the group of inorganic molecules and their aggregates.

Most preferably, in a detection device according to the invention, said bait molecule is selected from the group consisting of antigen-specific antibodies, pathogen-specific antibodies, tumor cell specific antibodies, growth factor receptors, hormone receptors, lipid-binding proteins, neurotransmitter receptors, catecholamine receptors, amino acid derivative receptors, cytokine receptors, extracellular matrix receptors, lectins, cytokines, serpins, proteases, kinases, phosphatases, ras-like GTPases, hydrolases, steroid hormone receptors, transcription factors, heat-shock transcription factors, DNA-binding proteins, zinc-finger proteins, leucine-zipper proteins, homeodomain proteins, intracellular signal transduction modulators and effectors, apoptosis-related factors, DNA synthesis factors, DNA repair factors, DNA recombination factors, cell-surface antigens, hepatitis C virus (HCV) proteases or HIV proteases and antibodies, growth factors, hormones, drugs, oligonucleotides, nucleic acids, sugar residues, lipids, small molecules, polymers, inorganic molecules and their aggregates The one skilled in the art may manufacture a fusion complex according to the invention quite easily, notably through the well-known recombinant DNA technology methods for manufacturing expression vectors that encode fusion proteins.

For general methods disclosing recombinant genetic engineering production of proteins, the one skilled in the art may notably refer to the book of Sambrook et al. (1989). The one skilled in the art may also refer to the book of Ausubel et al. (1989).

An illustrative embodiment of the production of a fusion complex which can be used for manufacturing a device according to the invention is given in the examples herein, i.e. the production of the fusion protein comprising the Annexin-A5 protein of SEQ ID No 1 with the ZZ domain of protein A from the *Staphylococcus aureus*.

In the specific embodiment of a fusion complex that is illustrated in Example 1, the Annexin-A5 moiety of SEQ ID No 1 with the double mutation [T 163C; C 314S] and the second protein moiety (the ZZ domain) are covalently linked together through a peptide bond in the final recombinant fusion protein.

Thus, in one preferred embodiment of the invention device, in said fusion complex, the Annexin moiety and the partner molecule, e.g. the second protein moiety, are covalently linked together through a normal peptide bond.

In one specific embodiment of said fusion complex, this fusion complex consists of a recombinant protein.

In another embodiment of the invention device, said fusion complex consists of an Annexin protein that is chemically covalently bound to a partner molecule, e.g. a second protein moiety, through a covalent bond other than a peptide bond, as illustrated in Example 2.

This further embodiment above is notably illustrated by the chemical cross-linking between the Annexin-A5 [T163C; C314S] moiety and the second protein through a cysteine residue incorporated in the Annexin-A5 moiety and a cysteine-reactive group grafted to the second protein. In such a specific embodiment, it may be used a functionally active derivative of the Annexin-A5 protein of SEQ ID No 1, wherein the cysteine residue located in the amino acid position 314 is replaced by a serine residue and wherein the threonine residue located in the amino acid position 163 is replaced by a cysteine residue. Grafting of a cysteine-reactive group to any protein is performed according to well known methods for the one skilled in the art by means of hetero-bifunctional cross-linking reagents. For general methods disclosing chemical modification of proteins by protein chemistry, the one skilled in the art may notably refer to the book of Wong (1991).

Thus in a specific embodiment of the detection device according to the invention, the Annexin-A5 protein and the second protein are covalently linked together through a chemical bond between a cysteine residue of the Annexin-A5 protein and a cysteine-reactive group grafted on the second protein.

In certain preferred embodiments of a device according to the invention, said device also comprises a substrate and said lipid layer is coated on said substrate.

According to these preferred embodiments, said substrate may consists of a solid substrate.

A solid substrate may be preferably selected from the group consisting of mica, silicon, mineral glass and gold.

In other preferred embodiments, said substrate consists of the air-liquid interface of a liquid medium.

As it is readily understood, following the above general description of the device according to the invention, said device allows a high level of miniaturization of target molecules screening means and is preferably used as a biochip for screening simultaneously for the presence either of multiple target molecules in an assay sample or of one target molecule using multiple bait molecules.

Therefore, the present invention also concerns a system that comprises more than one type of bait molecules included in anchoring complexes, namely a collection of bait molecules included in anchoring complexes.

Thus, the present invention also pertains to a system for detecting the binding of a target molecule onto a bait molecule, wherein said system comprises a plurality of detection devices as defined above.

Preferably, in said detection system, each detection device of said plurality of detection devices comprises a unique bait molecule, notably a unique bait protein. It must be noticed than one given bait molecule may specifically bind to more than one target molecule that is present in an assay sample to be tested.

Preferably, in said detection system, two distinct detection devices that are included therein comprise distinct bait molecules, notably distinct bait proteins. The detection devices that are the subject-matter of the present invention, and particularly those that are included in a detection system as defined hereabove, may comprise the solid substrate under the form of particles that are made of this solid substrate or alternatively under the form of particles that are coated with this solid substrate.

In another embodiment of a device according to the invention, the solid substrate is under the form of a collection of solid particles. In this specific embodiment of the invention's device, said particles, preferably silica particles, silica-coated particles or glass beads, are coated with a lipid bi-layer of the kind already defined above (Mornet et al., 2005), onto which are bound anchoring complexes of the invention.

Preferably, according to this specific embodiment, each particle or bead which is part of the device contains, bound thereto, a large number of molecules of one given type of bait protein.

An illustrative example of a detection system according to the invention that is manufactured under the form of a biochip, consists of a system comprising a serial of anchoring complexes comprising a serial of bait molecules, which serial of bait molecules consists of a serial of distinct target-specific antibodies, each target-specific antibody being directed against a distinct specific antigen, and/or against distinct epitopes of a given antigen, so as to screen an assay sample for the presence of one or more target molecules consisting of one or more antigens recognized by the corresponding target-specific antibody.

The device or the detection system according to the invention is used for performing methods for assaying the binding of a target molecule contained in an assay sample, including any screening method of target molecules of biological interest, including target molecules of therapeutical interest.

Thus, a further object of the invention consists of a method for detecting the binding of a target molecule onto a bait molecule, wherein said method comprises the steps of:
 a) providing a sample to be tested;
 b) bringing into contact the sample to be tested with a detection device or with a detection system as defined above; and
 c) detecting the complexes eventually formed between (i) the bait molecule(s) contained in said detection device or in said detection system and (ii) the target molecule(s) eventually present within said tested sample.

This invention also relates to a method for assaying for the presence of a target molecule in a sample comprising the steps of:
 a) providing a fusion complex between an Annexin protein and a bait molecule which binds to said target molecule;
 b) mixing the sample with said fusion complex, whereby complexes between the bait moiety of said fusion complex and the target molecule are allowed to be formed;
 c) immobilizing the fusion complexes obtained at step b), eventually under the form of complexes with said target molecule, at the surface of a phospholipid bi-layer coating a solid substrate, said phospholipid bi-layer comprising a combination of (i) one or more lipids with (ii) one or more phospholipids, said one or more phospholipids having a negative net charge in an aqueous solution at a neutral pH;
 c) detecting the complexes that are formed between the bait moiety of said fusion complex and the target molecule when said target molecule is present in said sample.

This invention also relates to a method for assaying for the presence of a target molecule in a sample comprising the steps of:
 a) providing a bait molecule which binds to said target molecule; said bait molecule may be i) part of a fusion complex with an Annexin protein; ii) a molecule that binds to a second molecule that is part of an Annexin-A5 fusion complex; iii) a molecule that binds to an intermediate molecule that itself binds to a second molecule that is part of an Annexin-A5 fusion complex;

b) mixing the sample with said bait molecule, whereby complexes between the bait molecule and the target molecule are allowed to be formed;

c) immobilizing the complexes obtained at step b), eventually under the form of complexes with said target molecule, at the surface of a lipid layer, said lipid layer being i) either a lipid bi-layer coating a solid substrate; ii) or a lipid mono-layer formed at the interface between air and an aqueous solution; said lipid layer comprising a combination of (i) one or more lipids with (ii) one or more phospholipids, said one or more phospholipids having a negative net charge in an aqueous solution at a neutral pH;

d) detecting the complexes that are formed between the bait moiety of said anchoring complex and the target molecule when said target molecule is present in said sample.

In a preferred embodiment of the method above, the fusion complex comprises a protein having affinity for the Fc moiety of an antibody, said antibody being either the bait protein, or a bait-specific antibody, or directed against a molecule that binds to the bait molecule.

In a further preferred embodiment of the method above, the fusion complex comprises a protein consisting of the ZZ domain of protein A from *Staphylococcus aureus*.

In a further preferred embodiment of the method above, the fusion complex comprises a protein consisting of the G protein from *Streptococcus* sp.

In a further preferred embodiment of the method above, the fusion complex comprises a bait protein consisting of an antibody fragment comprising the CDR domains of a target-specific antibody.

In a further preferred embodiment of the method above, the fusion complex comprises an antibody fragment comprising the CDR domains of a bait-specific antibody.

In a further preferred embodiment of the method above, the fusion complex comprises a bait protein selected from the group consisting of growth factor receptors, hormone receptors, neurotransmitter receptors, catecholamine receptors, amino acid derivative receptors, cytokine receptors, extracellular matrix receptors, lectins, cytokines, serpins, proteases, kinases, phosphatases, ras-like GTPases, hydrolases, steroid hormone receptors, transcription factors, heat-shock transcription factors, DNA-binding proteins, zinc-finger proteins, leucine-zipper proteins, homeodomain proteins, intracellular signal transduction modulators and effectors, apoptosis-related factors, DNA synthesis factors, DNA repair factors, DNA recombination factors, cell-surface antigens, hepatitis C virus (HCV) proteases or HIV proteases and antibodies, oligonucleotides, nucleic acids, sugar residues, lipids, small molecules, polymers, inorganic molecules and their aggregates.

In an illustrative embodiment, the detection, the quantification or the characterization of the target molecules is performed by mass-spectrometry or alternatively by one of known surface-sensitive methods, like fluorescence, ellipsometry, QCM-D, surface plasmon resonance.

In another illustrate embodiment, the detection, the quantification or the characterization of the target molecules is performed by using target-specific antibodies, said target-specific antibodies being labeled prior to performing the assay method.

In such a specific embodiment, the detection, quantification or characterization of the complexes formed between the bait molecule (s) and the target molecule (s) of the invention's device is carried out through the detection of the detectable molecule that will be finally bound to said device.

The detectable molecule may be a radioactive isotope such as $^3[H]$, $^{14}[C]$, $^{125}[I]$ or $^{32}[P]$. The detectable molecule may also be a fluorescent molecule such as a small fluorescent dye molecule or a protein of the green fluorescent protein (GFP) family. The detectable molecule may be an enzyme, such as the well-known β-galactosidase, luciferase, peroxydase, alkaline phosphatase, acetylcholinesterase, or catalase. Any other conventional detectable molecule widely used in the art is herein encompassed by a detectable molecule usable according to the assay method of the invention.

As another embodiment of the detection step, the detection, quantification or characterization of the complexes formed between the bait molecule(s) and the target molecule(s) can be carried out using is antibodies directed against a specific target molecule of interest, the presence of which in the assay sample is sought.

In a further embodiment of the detection step, the detection, the quantification or the characterization, of the complexes formed between the bait molecule(s) and the target molecule(s) is carried out using the method of the Quartz Crystal Microbalance with Dissipation Monitoring (QCM-D) as illustrated in Example 5 and in FIGS. 10 to 14.

As it appears clearly from the specification above, the assay device and methods of the invention gather numerous technical advantages that cannot be found in such an advantageous combination in the prior art devices and methods.

Firstly, the assay device of the invention, once conceived by the inventors, can be easily and reproducibly manufactured. As an illustration, the manufacture of either the lipid bi-layer on the solid substrate or of the mono-layer at an air-water interface, and the further formation of a high-density matrix of the fusion complexes thereto may be performed in less than a one-hour period of time.

Secondly, as it has been already mentioned in the above description, the controlled orientation of the Annexin-A5 moieties on the lipid layer allows an appropriate exposure of the bait proteins of interest to the solvent, ensuring maximal efficiency of capture of the target molecules that are eventually contained in the assay sample to be analyzed.

Thirdly, the lipid-layer covers the entire surface of either the air-water interface or the solid substrate, and the lipid layer is covered by a continuous 2D assembly of Annexin-A5 or Annexin-A5 derivatives, both of them preventing non-specific adsorption of molecules.

Fourthly, the quasi-irreversible immobilization of the bait proteins at the surface of the lipid layer is obtained through the properties of the Annexin-A5 protein moieties, including the functionally active derivatives of the Annexin-A5 proteins.

Fifthly, the complete coverage of the lipid layer by the 2D matrix of anchoring complexes is obtained through the 2D self-assembly properties of the Annexin-A5 moiety.

Further, in a device according to the invention, the bait proteins, as well as the complexes between the bait proteins and their corresponding target molecules, are separated from the solid substrate by the phospholipid bi-layer, which avoids the problems of the bait protein denaturation which are generally encountered with prior art methods and devices.

This strategy may be extended to other molecules, notably proteins, that present the basic property of forming 2D molecular matrices of high-density, and stable, on lipid layers. The strategy may be extended notably to proteins that present the property of forming 2D crystals on lipid layers, as this is the case for Annexins, notably Annexin-A5 on lipid mono-layers (Mosser et al., 1991; Voges et al. 1994; Brisson et al., 1999a; Brisson et al., 1999b) and phospholipid bi-layers (Reviakine et al., 1998). Examples of proteins that form 2D crystals by specific interaction with lipids incorporated into lipid mono-layers at the air-water interface can be found in Brisson et al., 1999a and in Ellis and Hebert (2001). An example of a protein that presents the basic property of forming stable high-density 2D arrangements on lipid surfaces is streptavidin, which forms 2D crystals on lipid mono-layers containing biotinylated lipids (Darst et al., 1991; Brisson et al., 1999b; Farah et al., 2001; Ratanabanangkoon and Gast, 2003), as well as on lipid bi-layers containing biotinylated lipids coating solid-supports (Reviakine and Brisson, 2001; Richter and Brisson, 2003). The binding and the detection of target molecules could be realized by use of bait molecules that will be linked either directly or indirectly to the 2D matrix of anchoring complexes containing streptavidin. Linking between the bait molecule and streptavidin may involve: 1) a fusion complex obtained by recombinant DNA technology, ii) the chemical cross-linking with a biotinylated bi-functional reagent of either the bait molecule, the second molecule of the fusion complex, or an intermediate molecule of the anchoring complex located between the bait molecule and the second molecule. Another example of a protein that forms stable high-density 2D matrix on lipid surfaces is the $B_5$ moiety of cholera toxin from *Vibrio cholerae* which binds to GM1 ganglioside-containing lipid surfaces (Ludwig et al., 1986; Mosser et al., 1992; Brisson et al., 1999b). Other examples are proteins engineered with a polyhistidine extension which form high-density 2D matriceson lipid surfaces containing lipid molecules covalently modified with a N",N"-bis[carboxymethyl]-L-lysine-(nitriloacetic acid)-nickel-chelating group (Kubalek et al., 1994; Brisson et al., 1999a). Examples of such proteins are the protein HupR from *Rhodobacter capsulatus* (Venien-Bryan et al., 1997) and the extracellular fragment of the vascular endothelium cadherin VE-EC$_{1-4}$ (Al-Kurdi et al., 2004). Yet another example of proteins that self-assemble as 2D protein matrices on various types of lipid surfaces consists of the S-layer family of proteins (Schuster and Sleytr, 2000; Moll et al., 2002).

As previously specified, certain embodiments of a device according to the invention provide useful vectors for targeting the delivery therapeutical molecules of interest towards specific cell types, specific tissue types or specific organs, in patients in need thereof.

According to these embodiments, a device of the invention is under the form of lipid vesicles, i.e. liposomes, wherein at least the outer lipid layer which is exposed to the solvent has a negative net charge in an aqueous solution at a neutral pH and is coated with the two-dimensional matrix of anchoring complexes comprising bait molecules that may specifically bind to target molecules that are present in a biological fluid, at the membrane surface or in the intracellular content of the targeted cell(s), of the targeted tissue(s) or of the targeted organ(s). According to these embodiments, the inner part of said lipid vesicles comprises a liquid medium in which one or more therapeutically useful compounds are dissolved or suspended. The inner part of the lipid vesicles or liposomes may herein also be termed "core" or "inner core" and consists of the inner central part of said lipid vesicles or liposomes that contains a liquid medium, preferably an aqueous liquid medium wherein one or more pharmaceutically active ingredients are dissolved or suspended.

According to these embodiments, devices according to the invention may be administered to a patient, either by a systemic or a local route. Then, said devices that comprise bait molecules specifically bind to cells, tissues or organs that express the corresponding target molecules at their surface. Then, the devices that are bound to the target cells, tissues or organs through specific binding of the bait molecules onto the target molecules are internalized within the cells and deliver the therapeutically useful molecules that were initially contained in the inner part of the lipid vesicles of the devices according to the invention.

Illustratively, the bait molecules that are part of the anchoring complexes comprised in such embodiments of a device according to the invention may consist of bait molecules that specifically bind to antigens that are specifically expressed or present at the cell surface of cancer cells. According to these embodiments, the therapeutically useful molecules that are contained in the inner part of the lipid vesicles of said devices are selected from the group consisting of the pharmaceutical ingredients that are active against cancer, such as well known cytotoxic ingredients that are currently used for treating cancer patients.

Thus, the present invention further relates to a vector for targeting therapeutical molecules comprising a device according to claim 1, wherein said device consists of lipid vesicles having:

a) an outer lipid layer comprising one or more lipids, said lipid layer having a negative net charge in an aqueous solution at a neutral pH;

b) a two-dimensional matrix of anchoring complexes that are bound to said lipid layer, wherein each of said anchoring complexes comprises:

(i) a fusion complex comprising an Annexin protein fused to a partner molecule, wherein:

said Annexin protein is bound to said phospholipid layer, and said partner molecule consists of an organic or a mineral compound;

(ii) a bait entity selected from the group consisting of:

said partner molecule that is fused to said Annexin protein;

a molecule that is covalently or non-covalently bound to said partner molecule;

a molecule that is indirectly bound to said partner molecule through one or more intermediate molecules that are covalently or non-covalently bound to said partner molecule; and c) in the inner part of said lipid vesicles, a liquid medium comprising one or more pharmaceutically active molecules that are dissolved or that are suspended therein.

As mentioned above, in a vector for targeting therapeutical molecules according to the invention, the bait molecule specifically binds to a target molecule that is expressed at the surface of the targeted cell, of the targeted tissue or of the targeted organ of interest.

Preferably, in a vector above, the anchoring complexes consist of an Annexin protein fused to the bait molecule, thus a fusion complex between said Annexin molecule and said bait molecule.

The bait molecule may be of any kind of a bait molecule disclosed in the present specification.

The present invention is further illustrated, without in any way being limited to, the examples below.

EXAMPLES

Example 1

Production of a Fusion Complex Between Annexin-A5 [T163C; C314S] and a Second Protein by Recombinant DNA Technology Methods, Wherein Said Second Protein Consists of the ZZ Domain of Protein A from *Staphylococcus aureus*

Example 1-1

Construction of Annexin-A5 [T163C: C314S]-ZZ Expression Vector

The expression vector containing the coding sequence of rat Annexin-A5 linked to the coding sequence of the ZZ domain analogous to protein A from *Staphylococcus aureus* was constructed by standard methods of molecular biology.

The rat Annexin-A5 coding sequence was excised by NcoI digestion from a pKK233-2-Annexin-A5 expression vector (Pepinsky et al., 1988) and cloned into the expression vector pGELAF+ (Schanstra et al., 1993) between two NcoI restriction sites, resulting in the pGEF-A5 expression vector.

Site-directed mutagenesis was performed by standard procedures (Kunkel, 1985) to insert the double mutation [T163C; C314S], resulting in the pGEF-A5B expression vector. All the assays available to us were performed to verify that the (T163C; C314S) double-mutant Annexin-A5protein presents all the known properties of wild type Annexin-A5, particularly in what concerns its binding to lipid membranes, and the formation of 2D crystalline arrays of trimers on lipid monolayers (Oling et al., 2001; Govorukhina et al., 2002), and on mica-supported lipid bi-layers (Reviakine et al., 1998). For this reason, the term Annexin-A5 used here refers to the double-mutant (T163C; C314S) Annexin-A5.

In order to fuse the ZZ coding sequence at the 3' end of the Annexin-A5 gene, the stop codon of Annexin-A5 in pGEF-A5B was removed and replaced by TAA. The PCR fragment produced with the primers: 5'-GAA GAGCTCAGGGCCATAAAACAAG-3' [SEQ ID No 19] (SacI site underlined) and 5'-CAT GCTAGCTAAGTCATCCTCGCCTCCACAGA-3' [SEQ ID No 20] (NheI site underlined) was digested with SacI and NheI and ligated into SacI/NheI digested pGEF-A5B, resulting in pGEF-A5B'.

A ZZ fragment lacking the signal sequence and containing a NheI and a BamHI restriction sites was produced by PCR from the pEZZ18 vector (Amersham BioSciences). The primers used were 5'-TGT GCTAGCCAAGCCGTAAACAAATTCAAC-3' [SEQ ID No 21] (NheI site underlined) and 5'-GCA GGATCCCTATACCGAGCTCGAATTCGCGTCTAC-3' [SEQ ID No 22] (BamHI site underlined). The PCR product was digested with NheI and BamHI and introduced by ligation into NheI/BamHI digested pGEF-A5B', resulting in pGEF-A5BZZ. The sequence coding for the Annexin-A5-ZZ protein was excised by XbaI/BamHI and cloned into the pET-11b expression vector (Novagen), resulting into the pET-A5BZZ expression vector.

The nucleotidic sequence corresponding to the Annexin-A5-ZZ fusion protein was verified by standard methods and assessed to code for the amino acid sequence of SEQ ID No 6.

Example 1-2

Expression of the Annexin-A5-ZZ Fusion Protein

*Escherichia coli* BL21 (DE3) cells were transformed by heat shock with plasmid pET-A5BZZ. Cells were plated on LB plates containing ampicillin (100 µg/mL), and incubated overnight at 37° C.

One clone was collected and incubated in 25 ml LB-ampicillin medium at 37° C. for ~20 hr, ending up with an $OD_{600}$~3. The necessary volume was taken and diluted to an OD of 0.1 in 400 mL LB-ampicillin medium.

The culture was then incubated at 30° C. until OD reaches 0.6-0.7, after which induction was started with 0.4 mM IPTG and incubation was carried out for another 16 hr at 30° C. The final $OD_f$ was measured.

The cells were harvested by centrifugation (10 min, 6,700 g) and the pellet was resuspended in a volume of buffer containing 10 mM Tris, 1 mM EDTA, 0.01% $NaN_3$, 10% glycerol, pH 7.5, equal to $6.7 \times OD_f$.

The cell suspension was sonicated at 4° C. with a Branson sonicator operated in a pulse mode with five steps of sonication at 13 W for 1 min with 15 sec intervals. Membrane fragments and large debris were separated by centrifugation at 48,000 g for 1 hour at 4° C. The supernatant, referred to as cell soluble extract (CSE) was collected and stored until use at 4° C.

The Annexin-A5-ZZ fusion protein is expressed at high levels, as shown in FIG. 7A.

Example 1-3

Purification of Annexin-A5-ZZ Fusion Protein

The CSE was filtered over 0.22 µm filters and applied in 5 mL fractions to a Superdex 75 exclusion column (Amersham BioSciences) pre-equilibrated with a buffer containing 20 mM Tris, pH8, 0.02% $NaN_3$ (buffer A). Elution of the proteins was performed with buffer A. The Annexin-A5-ZZ fusion protein elutes at ~55 mL, as shown by SDS-PAGE (FIG. 7B).

The fractions containing Annexin-A5-ZZ were pooled and applied to a MonoQ HR5/5 anion-exchange column (Amersham BioSciences) pre-equilibrated with buffer A. Elution was performed with a 0 to 0.5 M NaCl gradient in buffer A. The Annexin-A5-ZZ fusion protein elutes as a pure protein at ~270 mM NaCl (SDS-PAGE analysis shown in FIG. 7C).

The mass of the purified protein was estimated by MALDI-TOF mass spectrometry analysis at 50077 Da, the theoretical mass without the initial methionine being 50074 Da.

An amount of ~40 mg pure Annexin-A5-ZZ protein is produced starting from 175 mg protein total protein in CSE from 400 mL cell culture (yield ~23%). The proteins stable for a period longer than one year when stored at 4° C.

The ability of Annexin-A5-ZZ complexes to form stable 2D self-assemblies and to bind IgGs is demonstrated by QCM-D (FIGS. 10,11,12).

Example 2

Production of the Fusion Complex Between Annexin-A5 [T163C: C314S] and a Second Protein by Covalent Chemical Linkage, Wherein said Second Protein Consists of Protein G from *Streptococcus* sp The formation of fusion complexes between recombinant protein G (Pierce Biotechnology, USA) from *Streptococcus* sp. and Annexin-A5 (T163C; C314S) is performed using the hetero-bi-functional reagent N-Succinimidyl.3-[2-pyridyldithio]-propionate (SPDP) (Pierce Biotechnology) in two steps: i) protein G is coupled to SPDP; ii) covalent complexes are formed between Annexin-A5 (T163C; C314S) which presents a single accessible sulfhydryl group and (2-pyridyl-disulfide-activated protein G).

In order to obtain protein G derivatized with a small number of SPDP molecules per protein G molecule, protein G and SPDP are mixed in equimolar ratio. SPDP, dissolved in DMSO at 1 mg/mL, is mixed with an appropriate amount of protein G at 1 mg/mL in 160 mM borate buffer, pH 79. The reaction was performed by incubation for 2 hr at ambient temperature.

As Annexin-A5 (T163C; C314S) has a natural tendency to oxidize into disulfide-linked dimers, freshly reduced Annexin-A5 is prepared by reducing the disulfide-linked dimers of Annexin-A5 with DTT just before coupling with protein G-SPDP. 1 ml of a solution containing 1 mg Annexin-A5 dimer in 20 mM Tris, 300 mM NaCl, 0.01% $NaN_3$, pH 8 is mixed with 100 μl of 100 mM DTT in 10 mM HEPES, pH 6.4. After 30 min incubation at ambient temperature, the excess DTT is eliminated by gel filtration on a HiTrap desalting column (5 mL) eluted with 10 mM HEPES, 150 mM NaCl, pH 7.4.

Cross-linking between Annexin-A5 and (protein G-SPDP) is performed at a molar ratio (Annexin-A5/proteinG) equal to 2/1, as follows: the appropriate volumes of Annexin-A5 (~0.4 mg/mL) in 10 mM HEPES, 150 mM NaCl, pH 7.4 and of (protein G-SPDP) (~0.2 mg/mL) in 160 mM borate buffer, pH 7.9 were mixed and incubated for more than 16 hr at ambient temperature.

The characterization of the cross-linked products is performed by SDS-PAGE. Proteins migrating at positions expected for (Annexin-A5-proteinG) hetero-dimers and (Annexin-A5)$_2$-proteinG hetero-trimers are observed (FIG. 9 A).

The covalent cross-linked complexes between Annexin-A5 and protein G are purified by gel filtration on Superdex 75 (Amersham BioSciences) eluted in buffer A, followed by anion exchange chromatography on Mono-Q eluted with a 0-0.5 M NaCl gradient In buffer 5A. The fractions are analyzed by SDS-PAGE. Peaks corresponding to the AnnexinA5-proteinG hetero-dimers and (Annexin-A5)$_2$-proteinG hetero-trimers are separated (FIG. 9B).

50 μg of proteinG—Annexin-A5 complexes are obtained, starting from 1 mg Annexin-A5 dimer and 0.4 mg protein G, corresponding to ~6% yield for protein G.

The ability of proteinG—Annexin-A5 complexes to form stable 2D self-assemblies and to bind rat IgGs is demonstrated by QCM-D (FIG. 13).

Example 3

Production of the Anchoring Complex Made of a Dimer of Annexin-A5 [T163C: C314S]

The formation of anchoring complexes between two Annexin-A5 (T163C; C314S) molecules associated via a disulfide bond is performed by means of the reagent 4,4'-dithiodipyridine (DTDP).

The reduced form of Annexin-A5 (T163C; C314S) is obtained as described in Example 2.

The following protocol is recommended to oxydize reduced Annexin-A5 (T163C; C314S) with DTDP: reduced Annexin-A5 is mixed with DTDP at a molar ratio [Annexin-A5/DTDP] of 2.5, 50 mM sodium phosphate, pH 7.4, for 30 min. at ~20° C. The yield In disulfide-linked Annexin-A5 dimer is close to 75%. The disulfide-linked Annexin-A5 dimer is purified by anion exchange chromatography with a MonoQ HR5/5 column (Amersham BioSciences) pre-equilibrated with buffer A. The Annexin-A5 dimer elutes at ~280 mM NaCl. The mass of the purified protein is verified by MALDI-TOF.

Alternatively, the formation of (Annexin-A5-S-S-Annexin-A5) is obtained by spontaneous oxydation of the reduced Annexin-A5 (T163C; C314S) molecules.

Example 4

Production of an Anchoring Complex Between Annexin-A5 [T163C; C314S] and a RGD-Containing Peptide by Covalent Chemical Linkage and Application for Anchoring Target Cells Example 4-1

Production of an Anchoring Complex Between Annexin-A5 [T163C: C314S] and a RGD-Containing Peptide by Covalent Chemical Linkage The formation of anchoring complexes between Annexin-A5 (T163C; C314S) and a peptide containing the Arg-Gly-Asp (RGD) amino-acid sequence is performed by means of the reagent 4,4'-dithiodipyridine (DTDP).

The peptide sequence is GCRGYGRGDSPG (VandeVondele et al., 2003), which contains both the cell-adhesion motif RGD and a cysteine residue that is used to form a disulfide bond with (Annexin-A5 (T163C; C314S).

The reduced form of Annexin-A5 (T163C; C314S) is obtained as described in Example 2.

The following protocol is recommended: reduced Annexin-A5 is mixed with the GCRGYGRGDSPG and with DTDP at a molar ratio [Annexin-A5/RGD-peptide/DTDP] equal to 1/4/1 in 50 mM sodium phosphate, pH 7.4, for 30 min. at ~20° C. The yield in anchoring complex Annexin-A5-RGD peptide is close to 60%.

Alternatively, the formation of Annexin-A5-RGD peptide is obtained by spontaneous oxydation between the reduced Annexin-A5 (T163C; C314S) and the RGD-peptide.

The mass of the Annexin-A5-RGD peptide is verified by MALDI-TOF.

Example 4-2

Application of 2D Matrices of Annexin-A5-RGD Peptide on Lipid Bi-Layers Coating a Solid Substrate for Anchoring Target Cells The adhesion of human vascular endothelial cells to 2D matrices of Annexin-A5-RGD peptide on lipid bi-layers coating a glass substrate has been achieved. The adhesion of cells on the 2D matrices of Annexin-A5-RGD peptide is equivalent to the standard protocols used in the art for cell adhesion. As a control experiment, no adhesion is observed when 2D matrices of Annexin-A5 (lacking the RGD peptide) on lipid bilayers coating a glass substrate are used.

Example 5

Manufacture of a Detection Device According to the Invention

Example 5-1

Formation of a Stable 2D Self-Assembled Layer of Annexin-A5-ZZ Fusion Complex on a Supported Phospholipid Bi-Layer and Subsequent Binding of a Mouse Monoclonal Antibody by QCM-D The results are shown in FIG. 10.

This figure represents a typical example of an experiment in which a target molecule—here a mouse monoclonal antibody (IgG)—is detected by specific binding to a 2D self-assembled matrix of the fusion complex Annexin-A5-ZZ formed on a solid-supported phospholipid bi-layer (SLB).

I—Methods:

I-1) QCM-D

QCM-D measurements (Rodahl et al., 1995) were performed with the Q-SENSE D300 system equipped with an Axial Flow Chamber (QAFC 302) (Q-SENSE AB, Gothenburg, Sweden). as described in Richter et al. (2003). Briefly, upon adsorption of analytes to the surface of a silica-coated quartz crystal, changes in the resonance frequency, $\Delta F$, related to attached mass, and in the dissipation, $\Delta D$, related to frictional losses in the adlayer, are measured in real time.

In FIGS. 10-13, the abscissa represents the time, expressed in minutes. The left ordinate ($\Delta F$, blue) is expressed in Hz units and represents the variation of the normalized resonance frequency of the crystal at the 15 MHz harmonics. According to the Sauerbrey equation, the mass of adsorbed material is linearly related to $\Delta F$, ($m=-C \times \Delta F$, with $C=17.7$ ng·cm$^{-2}$·Hz$^{-1}$) (Sauerbrey, 1959). The right ordinate ($\Delta D$, orange) represents the variation in Dissipation.

I-2) Preparation of Lipid Vesicles 1,2-dioleoyl-sn-glycero-3-phosphocholine (DOPC) and 1,2-dioleoyl-sn-glycero-3-phospatidylserine (DOPS) (Avanti Polar Lipids (Alabama, USA) are dissolved in chloroform, mixed in desired amounts, dried first under a stream of nitrogen and subsequently in a vacuum desiccator overnight. Lipids are resuspended at ~1 mg/mL final concentration in a buffer containing 150 mM NaCl, 2 mM NaN$_3$ and 10 mM HEPES, pH 7.4 (buffer B), prepared in ultrapure water. Lipid suspensions are homogenized by 5 cycles of freeze-thawing and vortexing. Small unilamellar vesicles (SUVs) are obtained by sonication with a tip-sonicator (Misonix, N.Y., USA) operated in a pulsed mode at 30% duty cycle for 30 min with refrigeration, followed by centrifugation at 16,000 g for 10 min to remove titanium particles. SUV suspensions are stored at 4° C. under nitrogen until use.

II—Experiment:

At position 1 in FIG. 10, a solution of 100 µg/mL DOPC:DOPS (4:1; w:w) SUVs in buffer C (buffer B supplemented with 2 mM CaCl$_2$) was flushed on top of a silica-coated quartz crystal through the QCM-D chamber. The changes of $\Delta F$ and $\Delta D$, exhibiting a characteristic two-phase behavior, together with the $\Delta F$ and $\Delta D$ values obtained at the plateau, namely $\Delta F \sim -25$ HZ and $\Delta D \sim 0$, are characteristic of the formation of a homogeneous, defect-free, SLB on the silica-coated quartz crystal. For general methods disclosing the formation of lipid bilayers by deposition of lipid vesicles on solid substrates, the one skilled in the art may notably refer to the following articles (Keller and Kasemo, 1991; Richter et al., 2003; Richter and Brisson, 2003; Richter et al., 2005).

In 2, the QCM-D chamber is flushed with buffer C to remove the to excess of SUVs.

In 3, a solution of 20 µg/mL Annexin-A5-ZZ fusion protein in buffer C is injected. The specific binding of the fusion complex to the SLB results in a decrease of the frequency, $\Delta F \sim -31$ Hz, and a slight increase in dissipation, $\Delta D \sim 1.5 \times 10^6$. As reference, a 2D matrix of Annexin-A5 covering entirely a SLB gives rise to values of $\Delta F \sim -17$ Hz and $\Delta D \sim 0.2 \times 10^{-6}$. In 4, several rinses with buffer C are performed (blue arrows), which does not induce any release of bound material. These results indicate that the Annexin-A5-ZZ fusion complex forms a stably bound, 2D self-assembled matrix over the SLB.

In 5, a solution of 20 µg/mL of IgG in buffer C is added, resulting in a rapid decrease of the frequency, $\Delta F$ stabilizing at ~-53 Hz. The change in dissipation, $\Delta D_{final} \sim 3 \times 10^{-6}$, is characteristic of the presence of a flexible layer of adsorbed molecules on the sensor crystal. The IgG molecules are immobilized on the Annexin-A5-ZZ layer, as extensive rinsing with buffer C (R in FIG. 9) does not induce any release of bound material.

Control experiments were performed, which indicated that the IgG molecules do not bind non specifically to the SLB, nor to an Annexin-A5 matrix.

In 6, a solution of buffer C supplemented with 2 mM EDTA, a calcium-chelator, is flushed through the QCM-D chamber, resulting in the instantaneous displacement of the Annexin-A5-ZZ/IgG complexes bound to the SLB.

Example 5-2

Formation of a Stable 2D Self-Assembled Matrix of (Annexin-A5/Annexin-A5-ZZ) on a Supported Phospholipid Bilayer and Subsequent Binding of a Mouse Monoclonal Antibody, by QCM-D The results are shown in FIG. 11.

The principle of this experiment is similar to the one presented in FIG. 9, except that a mixture of (Annexin-A5/Annexin-A5-ZZ) (4:1; w:w) is used to form the 2D self-assembled matrix onto which the IgG molecules are subsequently immobilized.

In 1, injection of 100 µg/mL DOPC:DOPS (4:1; w:w) SUVs in buffer C The QCM-D chamber is then flushed with buffer C to remove the excess of SUVs (R in FIG. 11).

In 2, a solution containing a mixture of (Annexin-A5/Annexin-A5-ZZ) (4:1; w:w) at a total concentration of 20 µg/mL, in buffer C, is injected. At the plateau, binding of the (Annexin-A5/Annexin-A5-ZZ) mixture gives rise to $\Delta F \sim -20$ Hz. Taking into account that maximal $\Delta F$ values of $-17$ Hz and $-31$ Hz are obtained for pure Annexin-A5 (not shown) and pure Annexin-A5-ZZ (FIG. 9), respectively, and that the content of Annexin-A5-ZZ in the investigated mixture (Annexin-A5/Annexin-A5-ZZ) is 20%, the observed $\Delta F$ value found here, namely $-20$ Hz, is in agreement with what is expected from an ideal mixing of Annexin-A5 and Annexin-A5-ZZ.

In 3, the injection of 20 µg/mL of IgG in buffer C results in the rapid decrease of the frequency, $\Delta F$ stabilizing at ~-15 Hz. This value, obtained with 20% Annexin-A5-ZZ, is In agreement with the value of $-53$ Hz obtained with a 2D matrix of pure (100%) Annexin-A5-ZZ (as described above in Example 5-1), as it is likely that in the latter case the IgGs will not saturate all Annexin-A5-ZZ binding sites due to steric hindrance effect, the size of an IgG molecule being significantly larger (~150 kDa) than the size of an Annexin-A5-ZZ fusion complex (~50 kDa).

Example 5-3

Detection of the Binding of Complexes of (Annexin-A5-ZZ/IgG) Pre-Formed In Solution on a [PC:PS (4:1)]SLB, by QCM-D The results are shown in FIG. 12.

In this experiment, non-covalent complexes between Annexin-A5-ZZ molecules and mouse monoclonal IgG molecules were formed in solution, by mixing in 1.5 mL buffer C, for 15 minutes at ambient temperature, 40 µg Annexin-A5-ZZ and 120 µg IgG, which corresponds to an equimolar ratio of both species.

In 2, this mixture was injected over a DOPC:DOPS (4:1; w:w) SLB, formed in (1). Binding of the (Annexin-A5-ZZ/IgG) complexes results in a decrease of $\Delta F$ of −85 Hz. This value is almost identical to that obtained when the IgGs are added to a pre-formed Annexin-A5-ZZ layer (described in Example 5-1 and FIG. 10). This experiment indicates that complexes can be formed first in solution before being immobilized, via the specific interaction of the Annexin-A5 moiety on PS-containing lipid surfaces. The bound material is stable upon rinsing (R in FIG. 12).

Example 5-4

Detection of the Binding of a Rat Monoclonal Antibody (IgG) to a 2D Self-Assembled Matrix of a Chemically Cross-Linked Fusion Complex Between Annexin-A5 (T163C; C314S) and Protein G from *Streptococcus* sp. on a [PC:PS (4:1)] SLB, by QCM-D The results are shown in FIG. 13.

In this experiment, a chemically cross-linked complex made of Annexin-A5 and protein G was prepared, as described in Example 2 and FIGS. 9A,B), and was used for immobilizing rat monoclonal IgG molecules. Rat monoclonal antibodies react with protein G, but do not react with protein A.

In 1, injection of 100 µg/mL DOPC:DOPS (4:1; w:w) SUVs in buffer C. The QCM-D chamber is then flushed with buffer C to remove the excess of SUVs (R in FIG. 13).

In 2, a solution containing chemically cross-linked complex of (Annexin-A5-protein G) at a total concentration of 10 µg/mL in buffer C is injected. At the plateau, binding of the complex corresponds to $\Delta F$~−35 Hz. This value is expected for a 2D matrix of (Annexin-A5-protein G) covering entirely the SLB surface.

In 3, the injection of 20 µg/mL of rat monoclonal antibodies in buffer C results in the rapid decrease of the frequency, $\Delta F$ stabilizing at ~−25 Hz.

Example 6

Application of 2D Matrices of the (Annexin-A5-S-S-Annexin-A5) Fusion Complex Bound to Lipid Beavers Coating a Solid Substrate for Anchoring Target Liposomes The property of 2D matrices of the (Annexin-A5-S-S-Annexin-A5) fusion complex bound to lipid bi-layers coating a solid substrate to anchor target liposomes is described in Example 6 and illustrated in FIG. 14.

In 1, injection of 100 µg/mL DOPC:DOPS (4:1; w:w) SUVs in buffer C, which results in the formation of a supported lipid bi-layer.

In 2, a solution containing 40 µg/mL (Annexin-A5-S-S-Annexin-A5) dimer in buffer C is injected. At the plateau, binding of the (Annexin-A5-S-S-Annexin-A5) gives rise to $\Delta F$~−38 Hz. This value indicates that the (Annexin-A5-S-S-Annexin-A5) dimer is bound to the lipid bi-layer via one Annexin-A5 moiety, while the second moiety is exposed to the aqueous solution, as illustrated in FIG. 14.

In 3, injection of 100 µg/mL DOPC:DOPS (4:1; w:w) SUVs in buffer C, which results in the rapid binding of liposomes. Control experiments with pure DOPC liposomes and with DOPC:DOPS (4:1; w:w) SUVs in the absence of calcium ions, in which no adsorption of liposomes is observed, indicate that the binding of SUVs observed in (3) is specific.

This experiment demonstrates that 2D matrices of the (Annexin-A5-S-S-Annexin-A5) fusion complex bound to lipid bi-layers coating a solid substrate are able to anchor target liposomes, and by extension cell membranes containing negatively charged phospholipids.

Example 7

Formation of a 2D Crystalline Matrix of the Fusion Complex Annexin-A5-ZZ on a Lipid Mono-Layer at the Air-Water Interface In this experiment, a lipid mono-layer is formed at the air-water interface by applying 0.6 µl of a lipid mixture containing 150 µM DOPS −450 µM DOPC dissolved in chloroform:hexane (1:1, v:v) over a 17 µl droplet of 0.1 mg/ml Annexin-A5-ZZ in a buffer containing 2 mM $CaCl_2$, 150 mM NaCl, 10 mM HEPES, 3 mM $NaN_3$, pH 7.4, following standard procedures described in Brisson et al. (1999a,b). After incubation times ranging from 30 minutes to 16 hr, the interfacial film is transferred to an electron microscopy (EM) coated with a perforated carbon film and negatively stained with 1% uranyl acetate.

EM observations are performed with a Philips CM120 electron microscope operating at 120 kV, equipped with a 2k×2k Gatan-794 slow-scan CCD camera. Electron micrographs are recorded under low-dose conditions at a magnification of 45,000× and underfocus values close to 300 nm. The images are analyzed by Fourier transformation.

Annexin-A5-ZZ form 2D crystals with p6 symmetry structurally homologous to Annexin-A5.

TABLE 1

| SEQUENCES OF THE INVENTION | | |
|---|---|---|
| SEQ ID N° | Type | Description |
| 1 | Protein | Rat Annexin-A5 |
| 2 | Protein | Mouse Annexin A5 |
| 3 | Protein | Human Annexin A5 |
| 4 | Protein | Bovine Annexin A5 |
| 5 | Protein | Chicken Annexin A5 |
| 6 | Protein | Rat Annexin A5[T 163C; C 314S] -ZZ fusion protein |
| 7 | Protein | Human Annexin-1 |
| 8 | Protein | Human Annexin-2 |
| 9 | Protein | Human Annexin-6 |
| 10 | Protein | Human Annexin-4 |
| 11 | Protein | Human Annexin-8 |
| 12 | Protein | Human Annexin-7 |

TABLE 1-continued

SEQUENCES OF THE INVENTION

| SEQ ID N° | Type | Description |
|---|---|---|
| 13 | Protein | Hydat Annexin-C |
| 14 | Protein | Human Annexin-D |
| 15 | Protein | Human Annexin-B |
| 16 | Protein | Human Annexin-3 |
| 17 | Protein | Human Annexin-A |
| 18 | Protein | Human Annexin-9 |
| 19-22 | DNA | Primers |

REFERENCES

Al-Kurdi R., Gulino-Debrac D., Martel L., Legrand J. F., Renault A., Hewat E., Venien-Bryan C. A soluble VE-cadherin fragment forms 2D arrays of dimers upon binding to a lipid monolayer. J. Mol. Biol. 2004, 337:881-892.

Ausubel, et al., Current Protocol in Molecular Biology, Green Publishing Associates and WILEY Interscience, N.Y, 1989. Blackwood R. A., Ernst J. D. Characterization of $Ca^{2+}$-dependent phospholipid binding vesicle aggregation and membrane fusion by Annexins. Biochemistry J. 1990, 266:195-200.

Brisson A., Lambert O., Bergsma-Schutter W. Two-dimensional crystallization of soluble proteins on planar lipid films: a practical approach. In Crystallization of Nucleic Acids and Proteins: A practical Approach (Ducruix, A. & Giegd, R., eds) Oxford Univ Press, 1999a; pp. 341-363.

Brisson A., Bersgma-Schutter W., Oling F., Lambert O., Reviakine I. 2-D Crystallization of proteins on lipid monolayers at the air-water interface and transfer to an electron microscopy grid. J. Crystal Growth 1999b, 196:456-470.

Concha N. O., Head J. F., Kaetzel M. A. et al. Rat Annexin V crystal structure: $Ca^{2+}$-induced conformational changes. Science 1993, 261:1321-1324.

Darst S. A., Ahlers M., Meller P. H., Kubalek E. W., Blankenburg R., Ribi H. O., Ringsdorf H., Kornberg R. D. Two-dimensional crystals of streptavidin on biotinylated lipid layers and their interactions with biotinylated macromolecules. Biophys J. 1991, 59(2):387-96.

Eliasson M., Andersson R., Olsson A., Wigzell H., Uhlen M. Chimeric IgG-binding receptors engineered from staphylococcal protein A and streptococcal protein G. J. Biol. Chem. 1988, 263:4323-4327.

Ellis M. J., Hebert H. Structure analysis of soluble proteins using electron crystallography. Micron. 2001, 32:541-550.

Farah S. J., Wang S. W., Chang W. H., Robertson C. R., Gast A. P. Point Mutagenesis and Cocrystallization of Wild-Type and Mutant Proteins: A Study of Solid-Phase Coexistence in Two-Dimensional Protein Arrays. Langmuir 2001, 17:5731-5735.

Govorukhina N., Bergsma-Schutter W., Mazères-Dubut C., Mazères S., Drakopoulou E., Bystrykh L., Oling F., Mukhopadhyay A., Reviakine I., Lai Kee Him J., Brisson A. Self-assembly of Annexin-A5 on lipid membranes, in "Annexins: Biological importance and Annexin-related pathologies". Landes Bioscience, Georgetown USA, (Ed. J. Bandorowicz-Pikula), 2002, pp. 40-58.

Huber R, Romisch J, Paques EP. The crystal and molecular structure of human Annexin V, an anticoagulant protein that binds to calcium and membranes. EMBO J. 1990, 9:3867-3874.

Kaetzel M. A., Mealy T. R., Mo Y. D., Campos B., Bergsma-Schutter W., Brisson A., Dedman J. R., Seaton B. A. Structure-function analysis of a site-directed mutant that mimics phosphorylation in Annexin IV. Biochemistry 2001, 40:4192-4199.

Keller C. A., Kasemo B. Surface specific kinetics of lipid vesicle adsorption measured with a quartz crystal microbalance. Biophys J. 1998, 75:1397-1402.

Kubalek E. W., Le Grice S. F., Brown P. O. Two-dimensional crystallization of histidine-tagged, HIV-1 reverse transcriptase promoted by a novel nickel-chelating lipid. J Struct Biol. 1994, 113:117-123.

Kunkel T. A. Proc. Natl. Acad. Sci. USA 1985, 82:488-492

Langen R., Isas J. M., Luecke H., Haigler, H. T., Hubbell, W. L. Membrane-mediated assembly of Annexins studied by site-directed spin labeling. J. Biol. Chem. 1998, 273: 22453-22457.

Loewenadler B. et al. (Gene 1987, 58:87.

Ludwig D. S., Ribi H. O., Schoolnik G. K., Kornberg R. D. Two-dimensional crystals of cholera toxin B-subunit-receptor complexes: projected structure at 17-A resolution. Proc Natl Acad Sci USA. 1986, 83(22):8585-8.

Meers P. Annexin Binding to Lipid Assemblies. In Annexins: Molecular Structure to Cellular Function. (Seaton BA, editor) R. G. Landes Company., 1996, pp 97-119.

Moll D., Huber C., Schlegel B., Pum D., Sleytr U. B., Sara M. S-layer-streptavidin fusion proteins as template for nano-patterned molecular arrays. Proc Natl Acad Sci USA. 2002, 99:14646-51.

Mornet S., Lambert M., Duguet E., Brisson A. The formation of supported lipid bilayers on silica nanoparticles revealed by cryo-electron microscopy. NanoLetters 2005, 5:281-285.

Mosser G., Ravanat C., Freyssinet J. M., Brisson A. Sub-domain structure of lipid-bound Annexin-V resolved by Electron image analysis. J. Mol. Biol. 1991, 217:241-245.

Mosser G., Mallouh V., Brisson A. A 9 A two-dimensional projected structure of cholera toxin B-subunit-GM1 complexes determined by electron crystallography. J. Mol. Biol. 1992, 226:23-28.

Nilsson B. et al. Protein Engineering 1987, 1:107

Oling, F., Bergsma-Schutter W. Brisson A. Trimers, dimers of trimers, and trimers of trimers are common building blocks of Annexin-A5 two-dimensional crystals. J. Struct. Biol. 2001, 133:55-63.

Pepinsky et al., J. Biol. Chem. 1988, 263:10799-10811

Pigault C., Follenius-Wund A., Schmutz M., Freyssinet J.-M., Brisson A. Formation of Two-dimensional Arrays of Annexin V on Phosphatidylserine-containing Liposomes. J. Mol. Biol. 1994, 236:199-208.

Ratanabanangkoon P., Gast A. P. Effect of Ionic Strength on Two-Dimensional Streptavidin Crystallization. Langmuir 2003, 19:1794-1801.

Reviakine I, Bergsma-Schutter W., Brisson A. Growth of protein 2-D crystals on supported planar lipid bilayers imaged in situ by AFM. J. Struct. Biol. 1998, 121:356-61.

Reviakine I., Bergsma-Schutter W., Mazères-Dubut C., Govorukhina N. Brisson A. Surface topography of the p3 and p6 Annexin V crystal forms determined by atomic force microscopy. J. Struct. Biol. 2000, 131:234-239.

Reviakine, I., Brisson, A. Streptavidin 2D crystals on supported phospholipid bilayers: towards constructing anchored phospholipid bilayers. Langmuir 2001, 17:8293-8299.

Richter, R. and Brisson, A., Characterization of lipid bilayers and protein assemblies supported on rough surfaces by atomic force microscopy. Langmuir 2003, 19: 1632-1640 Richter R., Mukhopadhyay A., Brisson A. On the influence of electrostatic interaction on the formation of lipid bilayers on silica surfaces. Biophys. J. 2003, 85:3035-3047.

Richter R. P., Maury N., Brisson A. On the effect of the solid support on the inter-leaflet distribution of lipids in supported lipid bilayers. Langmuir 2005, 21:299-304.

Richter R. P., Lai Kee Him J., Tessier B., Tessier C., Brisson A. R. On the kinetics of adsorption and two-dimensional self-assembly of Annexin A5 on supported lipid bilayers (submitted).

Rodahl M., Höök F., Krozer A., Brzezinski P., Kasemo B. Quartz crystal microbalance setup for frequency and Q-factor measurements in gaseous and liquid environments. Rev. Sci. Instrum. 1995, 66:3924-3930.

Ruoslahti E., Pierschbacher M. D. New perspectives in cell adhesion:
RGD and integrins. Science 1987, 238:491-497.

Sackmann E., Tanaka M. Supported membranes on soft polymer cushions: fabrication, characterization and applications. Trends Biotechnol. 2000, 18:58-64.

Sambrook J., Fritsch E. F., Maniatis T. Molecular Cloning: A Laboratory Manual, 2ième ed., Cold Spring Harbor Laboratory, Cold Spring Harbor, NEW YORK, 1989.

Sauerbrey G. Verwendung von Schwingquartzen zur Wägung dünner Schichten und zur Mikrowäagung. Zeitschrift für Physik 1959, 155:206-222.

Schanstra J. P., Rink R., Pries F., Janssen D. B. Protein Expr. Purif. 1993, 4:479-489.

Schuster B., Sleytr U. B. S-layer-supported lipid membranes. J. Biotechnol. 2000, 74:233-254.

Tait J. F., Gibson D., Fujikawa K. Phospholipid binding properties of human placental anticoagulant protein-I a member of the lipocortin family. J. Biol. Chem. 1989, 264:7944-7949.

Uhlen et al., Methods in Enzymology, 1990, vol./185:129-143.

VandeVondele S., Voros J., Hubbell J. A. RGD-grafted poly-L-lysine-graft-(polyethlene glycol) copolymers block non-specific protein adsorption while promoting cell adhesion. Biotech. Bioeng. 2003, 82:784-790.

Voges D., Berendes R., Burger A., Demange P., Baumeister W., Huber R. Three-dimensional structure of membrane-bound Annexin V—a correlative electron microscopy-X-ray crystallography study. J. Mol. Biol. 1994, 238:199-213.

Venien-Bryan C., Balavoine F., Toussaint B., Mioskowski C., Hewat E. A., Helme B., Vignais P. M. Structural study of the response regulator HupR from *Rhodobacter capsulatus*. Electron microscopy of two-dimensional crystals on a nickel-chelating lipid. J. Mol. Biol. 1997, 274(5):687-92

Wong, S. S., Chemistry of protein conjugation and cross-linking, CRC Press, Inc. 1991, pp. 1-340.

The invention claimed is:

1. A device for binding a target entity onto a bait entity that is immobilized on said device, comprising:
   a) a lipid layer which comprises one or more lipids, said lipid layer having a negative net charge in an aqueous solution at a neutral pH;
   b) a two-dimensional matrix of anchoring complexes that are bound to said lipid layer, wherein each of said anchoring complexes comprises:
      (i) a fusion complex comprising an Annexin protein fused to a partner molecule, wherein:
      said Annexin protein is bound to said lipid layer, and said partner molecule consists of an organic or a mineral compound;
      (ii) a bait entity selected from the group consisting of:
      said partner molecule that is fused to said Annexin protein;
      a molecule that is covalently or non-covalently bound to said partner molecule;
      a molecule that is indirectly bound to said partner molecule through one or more intermediate molecules that are covalently or non-covalently bound to said partner molecule.

2. The device of claim 1, wherein said lipid layer is selected from the group consisting of a lipid bilayer, a lipid monolayer or the external lipid layer of a liposome.

3. The device of claim 1, wherein said lipid layer comprises a combination of (i) one or more lipids with (ii) one or more phospholipids, said one or more phospholipids having a negative net charge in an aqueous solution at a neutral pH.

4. The device of claim 1, wherein said lipid layer comprises a combination of (i) one or more lipids with (ii) one or more phospholipids, said one or more phospholipids having a negative net charge in an aqueous solution at a neutral pH and said lipid layer has a content in said one or more phospholipids with a negative net charge from 2% to 100% by weight, based % on the total weight of said phospholipids bi-layer.

5. The device of claim 1, wherein the lipids (i) are selected from the group consisting of lecithin, DMPC, DOPC, POPC, egg-lecithin, DOPS, POPS, DOPA, DOPG, cardiolipin, DOTAP.

6. The device of claim 1, wherein the one or more phospholipids (ii) are selected from the group consisting of fatty acid esters of glycerophosphoserine, glycerophosphocholine, glycerophosphoglycerol and glycerophosphoethanolamine.

7. The device of claim 1, wherein the one or more phospholipids (ii) are selected from the group consisting of DMPS, DOPS, POPS, DOPA, DOPG cardiolipin, brain lipid extracts, and a mixture of them.

8. The device of claim 1, wherein the Annexin moiety of the fusion complex is selected from the group of Annexin proteins consisting of the amino acid sequences SEQ ID Nos 1-5 and 7-18 and functional derivatives thereof.

9. The device of claim 1, wherein, in the fusion complex between the Annexin protein and a partner protein, said partner protein consists of a protein having affinity for the Fc moiety of an antibody.

10. The device of claim 1, wherein, in the fusion complex between the Annexin protein and a partner protein, said partner protein consists of the ZZ domain of the A protein from *Staphylococcus aureus*.

11. The device of claim 1, wherein, in the fusion complex between the Annexin protein and a partner protein, said partner protein consists of the G protein from *Streptococcus*.

12. The device of claim 1, wherein, in the fusion complex between the Annexin protein and a partner protein, said partner protein consists of an antibody fragment comprising the CDRs of an antibody.

13. The device of claim 1, wherein, in the fusion complex between the Annexin protein and a partner protein, said partner protein consists of an antibody fragment consisting of Fab or scFv.

14. The device of claim 1, wherein, in the fusion complex between the Annexin protein and a partner protein, said partner protein consists of said bait molecule.

15. The device of claim 1, wherein said anchoring complex consists of:
(i) a fusion complex between an Annexin protein and an antibody fragment comprising the CDR domains of a target-specific antibody.

16. The device of claim 1, wherein said anchoring complex consists of:
(i) a fusion complex between an Annexin protein and an antibody fragment comprising the CDR domains of a bait-specific antibody; and
(ii) the bait molecule which is non covalently bound to the bait-specific antibody fragment of said fusion complex.

17. The device of claim 1, wherein said anchoring complex consists of:
(i) a fusion complex between an Annexin protein and a protein having affinity for the Fc portion of an antibody; and
(ii) an antibody which is non-covalently bound by its Fc portion onto said fusion complex, said antibody being said bait protein.

18. The device of claim 1, wherein said anchoring complex consists of:
(i) a fusion complex between an Annexin protein and a protein having affinity for the Fc portion of an antibody;
(ii) a bait-specific antibody which is non-covalently bound by its Fc portion onto said fusion complex; and
(iii) the bait protein which is non-covalently bound onto said bait-specific antibody.

19. The device of claim 1, wherein said bait molecule is selected from the group consisting of growth factor receptors, hormone receptors, neurotransmitter receptors, catecholamine receptors, amino acid derivative receptors, cytokine receptors, extracellular matrix receptors, lectins, cytokines, serpins, proteases, kinases, phosphatases, ras-like GTPases, hydrolases, steroid hormone receptors, transcription factors, heat-shock transcription factors, DNA-binding proteins, zinc-finger proteins, leucine-zipper proteins, homeodomain proteins, intracellular signal transduction modulators and effectors, apoptosis-related factors, DNA synthesis factors, DNA repair factors, DNA recombination factors, cell-surface antigens, hepatitis C virus (HCV) proteases or HIV proteases and antibodies, oligonucleotides, oligosides, small molecules, polymers, inorganic molecules and their aggregates.

20. The device of claim 1, wherein, in said fusion complex, the Annexin protein and the partner protein are covalently linked together through a normal peptide bond.

21. The device of claim 1, wherein said fusion complex consists of a recombinant fusion protein produced by recombinant DNA technology methods.

22. The device of claim 1, wherein, in said fusion complex, the Annexin protein and the partner protein are covalently linked together by a chemical bond other than a normal peptide bound.

23. The device of claim 1, wherein, in said fusion complex, the Annexin protein and the partner protein are covalently linked together through a chemical bond between a cysteine residue of the Annexin protein and a cysteine-reactive group of the partner protein.

24. The device of claim 1, wherein said device also comprises a substrate and wherein said lipid layer is coated on said substrate.

25. The device of claim 24, wherein said substrate consists of a solid substrate.

26. The device of claim 25, wherein said solid substrate is selected from the group consisting of mica, silicon, mineral glass and gold.

27. The device of claim 24, wherein said substrate consists of the air-liquid interface of a liquid medium.

28. A system for detecting the binding of a target molecule onto a bait molecule, wherein said system comprises a plurality of detection devices according to claim 1.

29. The system of claim 28, wherein each detection device of said plurality of detection devices comprises a unique bait protein.

30. The system of claim 28, wherein two distinct detection devices that are included therein comprise distinct bait molecules.

31. A method for detecting the binding of a target molecule onto a bait molecule, wherein said method comprises the steps of:
   a) providing a sample to be tested;
   b) bringing the sample to be tested into contact with a detection device according claim 1; and
   c) detecting the complexes eventually formed between (1) the bait molecule(s) contained in said detection device and (ii) the target molecule(s) eventually present within said tested sample.

32. A method for assaying for the presence of a target molecule in a sample comprising the steps of:
   a) providing a fusion complex between an Annexin protein and a bait molecule which binds to said target molecule;
   b) mixing the sample with said fusion complex, whereby complexes between the bait moiety of said fusion complex and the target molecule are allowed to be formed;
   c) immobilizing the fusion complexes obtained at step b), eventually under the form of complexes with said target molecule, at the surface of a lipid bi-layer coating a solid substrate, said lipid bi-layer comprising a combination of (i) one or more lipids with (ii) one or more phospholipids, said one or more phospholipids having a negative net charge in an aqueous solution at a neutral pH;
   c) detecting the complexes that are formed between the bait moiety of said fusion complex and the target molecule when said target molecule is present in said sample.

33. The method of claim 32, wherein the fusion complex comprises a bait molecule consisting of a protein having affinity with the Fc moiety of an antibody.

34. The method of claim 32, wherein the fusion complex comprises a bait molecule consisting of the ZZ domain of the protein A from *Staphylococcus aureus*.

35. The method of claim 32, wherein the fusion complex comprises a bait molecule consisting of a fragment of protein G from *Streptococcus* sp.

36. The method of claim 32, wherein the fusion complex comprises a bait molecule consisting of an antibody fragment comprising the CDR domains of a target-specific antibody.

37. The method of claim 32, wherein the fusion complex comprises a bait molecule selected from the group consisting of growth factor receptors, hormone receptors, neurotransmitter receptors, catecholamine receptors, amino acid derivative receptors, cytokine receptors, extracellular matrix receptors, lectins, cytokines, serpins, proteases, kinases, phosphatases, ras-like GTPases, hydrolases, steroid hormone receptors, transcription factors, heat-shock transcription factors, DNA-binding proteins, zinc-finger proteins, leucine-zipper proteins, homeodomain proteins, intracellular signal transduction modulators and effectors, apoptosis-related factors, DNA synthesis factors, DNA repair factors, DNA recombination factors, cell-surface antigens, hepatitis C virus (HCV) proteases or HIV proteases and antibodies, oligonucleotides, oligosides, small molecules, polymers, inorganic molecules and their aggregates.

38. A vector for targeting therapeutical molecules comprising a device, wherein said device comprises lipid vesicles having:
   a) an outer lipid layer comprising one or more lipids, said lipid layer having a negative net charge in an aqueous solution at a neutral pH;
   b) a two-dimensional matrix of anchoring complexes that are bound to said lipid layer, wherein each of said anchoring complexes comprises:
   (i) a fusion complex comprising an Annexin protein fused to a partner molecule, wherein:
      said Annexin protein is bound to said phopholipid layer, and
      said partner molecule consists of an organic or a mineral compound;
   (ii) a bait entity selected from the group consisting of:
      said partner molecule that is fused to said Annexin protein;
      a molecule that is covalently or non-covalently bound to said partner molecule;
      a molecule that is indirectly bound to said partner molecule through one or more intermediate molecules that are covalently or non-covalently bound to said partner molecule; and
   c) in the inner part of said lipid vesicles, a liquid medium comprising one or more pharmaceutically active molecules that are dissolved or that are suspended therein.

39. A method for detecting the binding of a target molecule onto a bait molecule, wherein said method comprises the steps of:
   a) providing a sample to be tested;
   b) bringing the sample to be tested into contact with a detection system according claim 28; and
   c) detecting the complexes eventually formed between (1) the bait molecule(s) contained in said detection system and (ii) the target molecule(s) eventually present within said tested sample.

* * * * *